(12) United States Patent
White et al.

(10) Patent No.: US 9,925,528 B2
(45) Date of Patent: Mar. 27, 2018

(54) CATALYST-CONTROLLED ALIPHATIC C—H OXIDATIONS

(71) Applicant: The Board of Trustees of the University of Illinois, Urbana, IL (US)

(72) Inventors: M. Christina White, Champaign, IL (US); Paul E. Gormisky, Watertown, MA (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 55 days.

(21) Appl. No.: 14/916,966

(22) PCT Filed: Sep. 9, 2014

(86) PCT No.: PCT/US2014/054835
§ 371 (c)(1),
(2) Date: Mar. 4, 2016

(87) PCT Pub. No.: WO2015/035412
PCT Pub. Date: Mar. 12, 2015

(65) Prior Publication Data
US 2016/0214097 A1 Jul. 28, 2016

Related U.S. Application Data

(60) Provisional application No. 61/875,536, filed on Sep. 9, 2013.

(51) Int. Cl.
| | |
|---|---|
| *C07F 15/00* | (2006.01) |
| *B01J 31/18* | (2006.01) |
| *C07B 33/00* | (2006.01) |
| *C07C 67/29* | (2006.01) |
| *C07D 307/93* | (2006.01) |
| *C07D 493/18* | (2006.01) |
| *C07F 15/02* | (2006.01) |
| *G06F 19/00* | (2018.01) |

(52) U.S. Cl.
CPC ......... *B01J 31/184* (2013.01); *B01J 31/1815* (2013.01); *C07B 33/00* (2013.01); *C07C 67/29* (2013.01); *C07D 307/93* (2013.01); *C07D 493/18* (2013.01); *C07F 15/025* (2013.01); *G06F 19/702* (2013.01); *B01J 2231/70* (2013.01); *B01J 2531/0258* (2013.01); *B01J 2531/842* (2013.01); *Y02P 20/582* (2015.11)

(58) Field of Classification Search
None
See application file for complete search history.

(56) References Cited

U.S. PATENT DOCUMENTS

| | | |
|---|---|---|
| 7,829,342 B2 | 11/2010 | White et al. |
| 2004/0087820 A1 | 5/2004 | Fuchs et al. |
| 2009/0093638 A1 | 4/2009 | Doyle et al. |
| 2009/0221083 A1 | 9/2009 | White et al. |
| 2011/0015397 A1* | 1/2011 | White .............. B01J 31/182 546/9 |
| 2012/0190635 A1 | 7/2012 | Li et al. |
| 2013/0184494 A1 | 7/2013 | Kurosawa et al. |

FOREIGN PATENT DOCUMENTS

| | | | |
|---|---|---|---|
| JP | 2006057014 A | * | 3/2006 |
| WO | 2007059015 A1 | | 5/2007 |
| WO | WO 2007059015 | * | 5/2007 |

OTHER PUBLICATIONS

Furstner, A. Alkene Metathesis in Organic Synthesis. Springer. 1998, p. 4.*
Gormisky, Paul E. et al., "Catalyst-Controlled Aliphatic C—H Oxidations With a Predictive Model for Site Selectivity," Journal of the American Chemical Society, 2013, 135, 14052-14055.
Gustafson, Jeffrey L. et al., "Linear Free Energy Relationship Analysis of a Catalytic Desymmetrization Reaction of a Diarylmethane-Bis(Phenol)," Original Letters, Jun. 18, 2010; 12(12); 2794-2797.
Harper, Kaid C. et al., "Three-Dimensional Correlation of Steric and Electronic Free Energy Relationships Guides Asymmetric Propargylation," Science, 333, 1875-1878 (2011).
International Search Report dated Dec. 4, 2014, Corresponding to related PCT Application No. PCT/US2014/054835.
International Written Opinion dated Dec. 4, 2014, Corresponding to related PCT Application No. PCT/US2014/054835.
Groves, J.T., et al., "Hydrocarbon Oxidations with Oxometalloporphinates. Isolation and Reactions of a (porphinato) Manganese(V) Complex," J. Am. Chem. Soc., 102(20):6375-6377, Sep. 1980.
Groves, J.T., et al., "Synthesis, Characterization, and Reactivity of Oxomanganese(IV) Porphyrin Complexes," J. Am. Chem. Soc., 110(26):8628-8638, Dec. 1988.

* cited by examiner

*Primary Examiner* — Andrew D Kosar
*Assistant Examiner* — Ben S Michelson
(74) *Attorney, Agent, or Firm* — Haukaas Fortius PLLC; Michael H. Haukaas

(57) ABSTRACT

The invention provides simple small molecule, non-heme iron catalyst systems with broad substrate scope that can predictably enhance or overturn a substrate's inherent reactivity preference for sp3-hybridized C—H bond oxidation. The invention also provides methods for selective aliphatic C—H bond oxidation. Furthermore, a structure-based catalyst reactivity model is disclosed that quantitatively correlates the innate physical properties of the substrate to the site-selectivities observed as a function of the catalyst. The catalyst systems can be used in combination with oxidants such as hydrogen peroxide to effect highly selective oxidations of unactivated sp3 C—H bonds over a broad range of substrates.

17 Claims, 11 Drawing Sheets

| entry (catalyst) | starting material %RSM | oxidation products % yield[a,b] | | site-selectivity[c] |
|---|---|---|---|---|
| | (+)-3[d,e] | (+)-4 | (+)-5 | 2°:3° |
| 1 (1) | 16 | 41 | 27 | 1:1 |
| 2 (2) | 8 | 51 | 11 | 4:1 |
| | 6[d,f] | 7 | 8 | 9 | 2°:3° |
| 3 (1) | 11 | 28 | 22 | 29 | 2:1 |
| 4 (2) | 15 | 44[g] | 26[h] | 7 | 10:1 |
| | 10[i] | 11 | 12 | 2°:3° |
| 5 (1) | 0 | 19 | 66 | 1:2 |
| 6 (2) | 9 | 51 | 28 | 2:1 |
| | (+)-13[e,i] | (+)-14 | (+)-15 | 2°:3°[k] |
| 7 (1) | 10 | 29 | 43 | 1:2 |
| 8 (2) | 8 | 56[j] | 15 | 4:1 |
| | (+)-16[e,i] | (+)-17 | (+)-18 | 2°:3°[k] |
| 9 (1) | 32 | 24 | 27 | 1:1 |
| 10 (2) | 8 | 51 | 6 | 9:1 |

*Figure 2*

| | A | B | C | D | E | F | G | H | I | J | K | L |
|---|---|---|---|---|---|---|---|---|---|---|---|---|
| 1 | FE(PDP)(1) | | | | | | | | | | | |
| 2 | | | | | | | | | | | | |
| 3 | SUBSTRATE | SITE | E | ATTACHED | THROUGH SPA | STEREOELECTRO | SUM A-VALUE | THROUGH SPA | STEREOELECTRO | A+TS-SE=S | E(NORM) | S(NORM) |
| 4 | 11DIMECY | 2,6 | 0.19905 | H,H,ET,TBU | X | | 8.59 | 0 | 0 | 8.59 | -0.1071687 | 0.27675277 |
| 5 | | 3,5 | 0.19845 | H,H,ET,ET | X | 1ME | 5.58 | 0 | 0.183 | 5.397 | -0.1506155 | -0.901476 |
| 6 | | 4 | 0.19818 | H,H,ET,ET | X | | 5.58 | 0 | 0 | 5.58 | -0.1701665 | -0.8339483 |
| 7 | CIS12DIMECY | 1,6 | 0.19046 | H,ME,ET,IPR | X | | 8.74 | 0 | 0 | 8.74 | -0.7291818 | 0.33210332 |
| 8 | | 2,5 | 0.19776 | H,H,ET,IPR | X | 1ME | 6 | 0 | 0.183 | 5.817 | -0.2005793 | -0.7464945 |
| 9 | | 3,4 | 0.19794 | H,H,ET,ET | X | 1ME | 5.58 | 0 | 0.183 | 5.397 | -0.1875453 | -0.901476 |
| 10 | TRANS12DIME | 1,6 | 0.18184 | H,ME,ET,IPR | 2AXH | | 8.74 | 1 | 0 | 9.74 | -1.3533671 | 0.70110701 |
| 11 | | 2,5 | 0.19749 | H,H,ET,IPR | X | | 6 | 0 | 0 | 6 | -0.2201303 | -0.6789668 |
| 12 | | 3,4 | 0.19767 | H,H,ET,ET | X | | 5.58 | 0 | 0 | 5.58 | -0.2070963 | -0.8339483 |
| 13 | TRANSOAC | 1 | 0.1942 | H,OAC,ET,ET | 2AXH | | 7.36 | 1 | 0 | 8.36 | -0.4583635 | 0.19188192 |
| 14 | | 2,6 | 0.21222 | H,H,ET,IPR | X | | 6 | 0 | 0 | 6 | 0.84648805 | -0.6789668 |
| 15 | | 3,5 | 0.20362 | H,H,ET,IPR | X | | 6 | 0 | 0 | 6 | 0.22375091 | -0.6789668 |
| 16 | | 4 | 0.18334 | H,ME,ET,ET | 2AXH | | 8.32 | 1 | 0 | 9.32 | -1.2447502 | 0.54612546 |
| 17 | HEX4MEESTER | 2 | 0.21821 | H,H,K,ET | X | | 5.04 | 0 | 0 | 5.04 | 1.28023172 | -1.0332103 |
| 18 | (+)-8 | 3 | 0.20922 | H,H,ET,IPR | X | | 6 | 0 | 0 | 6 | 0.62925416 | -0.6789668 |
| 19 | | 4 | 0.17801 | H,ME,ET,ET | X | | 8.32 | 0 | 0 | 8.32 | -1.6307024 | 0.17712177 |
| 20 | | 5 | 0.19178 | H,H,ME,IPR | X | | 5.95 | 0 | 0 | 5.95 | -0.6335988 | -0.697417 |
| 21 | HEX24MEESTE | 2 | 0.2143 | H,K,ME,ET | GAUCHE | | 7.78 | 0.9 | 0 | 8.68 | 0.99710355 | 0.3099631 |
| 22 | (+)-11 | 3 | 0.20345 | H,H,IPR,IPR | X | | 6.42 | 0 | 0 | 6.42 | 0.21144098 | -0.5239852 |
| 23 | | 4 | 0.18476 | H,ME,ET,ET | GAUCHE | | 8.32 | 0.9 | 0 | 9.22 | -1.1419261 | 0.50922509 |
| 24 | | 5 | 0.1891 | H,H,ME,IPR | X | | 5.95 | 0 | 0 | 5.95 | -0.8276611 | -0.697417 |

CATALYST-CONTROLLED ALIPHATIC C—H OXIDATIONS

RELATED APPLICATIONS

This application is a National Stage filing under 35 U.S.C. § 371 of International Application No. PCT/US2014/054835, filed Sep 9, 2014, which claims priority under 35 U.S.C. § 119(e) to U.S. Provisional Patent Application No. 61/875,536, filed Sep. 9, 2013, which applications are incorporated herein by reference.

BACKGROUND OF THE INVENTION

Intricate synthetic and natural organic bioactive molecules typically include a hydrocarbon skeleton containing a large number of aliphatic C—H bonds. The hydrocarbon skeleton is often decorated with oxidized functionalities, for example, carbons functionalized with oxygen and/or nitrogen containing groups. The identity and position of the oxidized functionalities strongly affect the biological activity of the molecule. Reactions that selectively introduce an oxidized functionality into an organic framework are therefore of particular significance in the synthesis of bioactive molecules.

Certain general reaction classes have emerged for introducing oxidized functionality into organic frameworks. These reaction classes include functional group interconversions, carbon-carbon bond forming reactions of pre-oxidized fragments, and olefin oxidations. Using these reactions, modern synthetic planning often focuses on the use and maintenance of oxidized functionalities once they have been introduced into the molecule.

In contrast, iron enzymes can perform catalytic, selective oxidations of isolated $sp^3$-hybridized C—H bonds in intricate molecules. Examples of these iron-containing enzymes include cytochrome P-450 and methane monooxygenase (MMO). The selective reactivity of such natural catalysts is dependent on elaborate protein binding pockets. Although binding pockets provide enzymes with good specificity and reactivity, they also limit the general applicability of the enzymes in the oxidation of a broad range of substrate molecules.

A major challenge in developing a useful oxidation reaction for intricate molecules is to develop a reaction system that is both highly reactive and predictably selective for oxidation of relatively inert and ubiquitous C—H bonds. Moreover, to be useful in intricate molecule synthesis, the reaction system would preferably have reactivity and selectivity that is general for a broad range of substrates. Such a reaction system could streamline complicated syntheses by providing methods to install oxidized functionalities at a late stage, thereby reducing unproductive chemical transformations associated with carrying the functionalities throughout a synthetic procedure. Furthermore, the reaction system would preferably rely on catalyst control as opposed to substrate control to broaden its synthetic applicability.

SUMMARY

Selective methods for aliphatic C—H bond oxidation can have a profound impact on chemical synthesis because these bonds exist across all classes of organic molecules. Central to realizing this goal is the development of catalysts with broad substrate scope (small molecule-like) that predictably enhance or overturn the substrate's inherent reactivity preference for oxidation (enzyme-like). The invention described herein provides a simple small molecule, non-heme iron catalyst that achieves predictable catalyst-controlled site-selectivity in preparative yields over a range of topologically diverse substrates. A structure-based catalyst reactivity model is described that quantitatively correlates the innate physical properties of the substrate to the site-selectivities observed as a function of the catalyst.

Accordingly, in one embodiment the invention provides a small molecule iron catalyst system that overrides substrate bias in aliphatic C—H oxidations with quantitatively predictable selectivity. For example, the invention provides a composition comprising a complex of Formula (I):

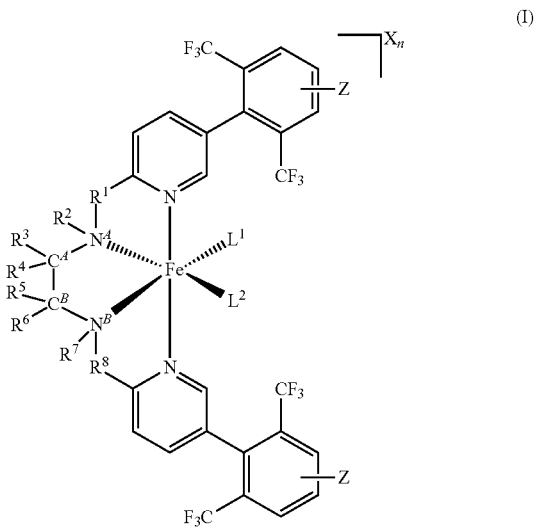

where X is a counterion; n is 2 or 3;
$L^1$ and $L^2$ are ancillary ligands;
each Z is independently H or $CF_3$;
$R^1$, $R^2$, $R^7$ and $R^8$ are each independently selected from the group consisting of an alkyl group, a heteroalkyl group, an aryl group, and a heteroaryl group, or they form part of an alkyl group, a heteroalkyl group, an aryl group, or a heteroaryl group;
$R^3$, $R^4$, $R^5$ and $R^6$ are each independently selected from the group consisting of hydrogen, halo, alkyl, heteroalkyl, aryl, and heteroaryl, or they form part of an alkyl group, a heteroalkyl group, an aryl group, and a heteroaryl group;
$C^A$ and $N^A$, in combination with at least one pair of groups selected from the group consisting of $R^1$ and $R^3$, $R^1$ and $R^4$, $R^2$ and $R^3$, and $R^2$ and $R^4$, form at least one ring; and
$C^B$ and $N^B$, in combination with at least one pair of groups selected from the group consisting of $R^8$ and $R^6$, $R^8$ and $R^5$, $R^7$ and $R^6$, and $R^7$ and $R^5$, can optionally form at least one ring.

Another aspect of the invention provides a composition comprising a complex of Formula (I) that is a complex of Formula (II) or Formula (IIB):

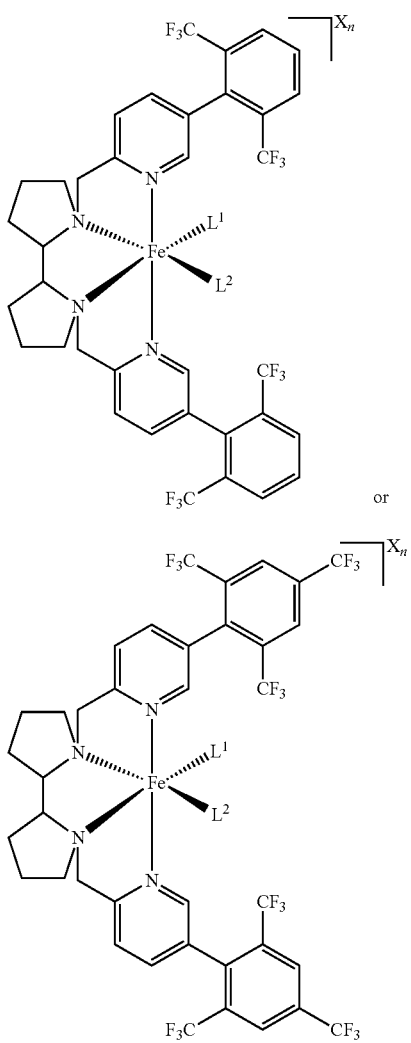

wherein X is a counterion; and n is 2 or 3. $L^1$ and $L^2$ are absent or are ancillary ligands; or $L^1$ and $L^2$ together are a carboxylate group. Useful counterions X include $Cl^-$, $Br^-$, $AcO^-$, $TfO^-$, $CF_3CO_2^-$, $BF_4^-$, $ClO_4^-$, $ReO_4^-$, $AsF_6^-$, and $SbF_6^-$, and the like. Useful ancillary ligands $L^1$ and $L^2$ include acetone, acetonitrile, a μ-oxo bridge or combinations thereof; or $L^1$ and $L^2$ together can be a carboxylate group. The complexes of Formula (I) or (II) can be the (S,S) enantiomer, (R,R) enantiomer, or combinations thereof. Reference to Formula (II) herein can include Formula (IIB).

Additionally, the invention provides ligands for complexing with metals, such as the ligand of Formula (I) or (II) (i.e., the compound resulting from the absence of the iron, ancillary ligands, and counterion(s)). Such ligands can be useful for oxidation reactions and catalysis with other transition metals, and as intermediates for the preparation of other useful ligands. For example, in one embodiment, the invention provides the compound 1,1'-bis((5-(2,6-bis(trifluoromethyl)phenyl)-pyridin-2-yl)methyl)-2,2'-bipyrrolidine ("Fe (CF3-PDP"). In another embodiment, the invention provides the compound 1,1'-bis((5-(2,4,6-tris(trifluoromethyl)phenyl)pyridin-2-yl)methyl)-2,2'-bipyrrolidine ("tri-CF3-PDP").

The invention also provides a method of oxidizing an organic substrate comprising contacting a substrate and an oxidant in a first reaction mixture, wherein the first reaction mixture comprises a composition of an iron complex described herein (e.g., a complex of Formula (I) or (II)), thereby oxidizing the organic substrate to provide an oxidized product. The organic substrate can by a cyclic or an acyclic compound having $sp^3$-hybridized C—H bonds, and the substrate can have one or more functional group substituents.

The invention further provides a method of selectively oxidizing an $sp^3$-hybridized C—H bond in a molecule comprising: contacting a substrate having an $sp^3$-hybridized C—H bond and an oxidant in a first reaction mixture in the presence of a composition of an iron complex described herein, thereby selectively oxidizing an $sp^3$-hybridized C—H bond in the molecule to provide an oxidized product.

The iron catalysts described herein were surprisingly found to be able to enhance, or alternatively overturn, a substrate's inherent oxidative reactivity, to provide oxidized substrates wherein an electronically disfavored 2° $sp^3$-hybridized C—H bond is oxidized selectively in preference to a 3° $sp^3$-hybridized C—H bond. Alternatively, an electronically disfavored 2° $sp^3$-hybridized C—H bond may be oxidized in preference to another, inherently favored 2° $sp^3$-hybridized C—H bond. Thus, the iron catalyst described herein provides catalyst controlled aliphatic C—H bond oxidation by restricting the trajectory of a substrates approach to the iron atom. The oxidation can be carried out in ambient conditions, for example, exposed to air and not under an inert atmosphere.

In some embodiments, the oxidation caused by the iron catalyst can provide an enantiomerically enriched product, for example, a product having an ee of at least about 30% or at least about 50%. Accordingly, the iron catalyst can be used to carry out enantioselective oxidations of achiral substrates. Use of an (S,S)-ligand containing iron catalyst can also provide increased yield and/or oxidative selectivity for certain chiral substrates compared to an (R,R)-ligand containing iron catalyst, and vice versa.

In yet another aspect, the invention provides a method of modeling the interaction of an enzyme, such as a cytochrome P-450 enzyme, with a substrate such as an organic molecule having $sp^3$-hybridized C—H bond, including reacting the substrate and an oxidant in a reaction mixture that includes a non-heme iron catalyst complex described herein; providing at least one oxidized product in the reaction mixture; and analyzing the at least one oxidized product to determine the location of the oxidation. In a further aspect, the invention provides a method to model oxidation reactivity of an $sp^3$-hybridized C—H bond in a molecule by calculating electronic parameters and steric parameters of available $sp^3$-hybridized C—H bonds, including calculated $\Delta\Delta G^{\ddagger}$ values, and comparing the parameters and values to determine the likeliest $sp^3$-hybridized C—H bond oxidation site of the molecule. This useful information can be used to design efficient synthetic routes that include oxidized products or intermediates.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIG. 2. Catalyst-Controlled Oxidation of Simple Cyclic and Acyclic Molecules. Legend: (a) Average of 3 runs. Standard deviations range from 1-4%. (b) Yields are of isolated material. (c) Crude ratio was determined by GC. (d) Method A: iterative addition of 5% Fe catalyst; AcOH (0.5 equiv), $H_2O_2$ (1.2 equiv), MeCN. (e) Starting material was recycled 1 time. (f) Yield determined by GC analysis. (g) Includes 6% 3β-hydroxy product. (h) Includes 5% 2α-hydroxy product. (i) Method B: ACOH (0.5 equiv) over 1 hour. (j) With 5% catalyst: 6% (+)-17, 2% (+)-18, 85% RSM. (k) Ratio determined by $^1$H NMR. Ns=4-nitrobenzenesulfonyl; Val=L-valine; Nva=L-norvaline.

DETAILED DESCRIPTION

Small molecule catalysis has achieved some predictable, substrate-controlled site-selective C—H oxidations with generality and operational ease. A non-heme iron hydroxylation catalyst Fe(PDP) (1) was recently described by Chen and White (Science 2007, 318, 783; Science 2010, 327, 566). The research showed that 3° (tertiary) and 2° (secondary) aliphatic C—H bonds can be preparatively differentiated based on electronic (favors electron rich sites), steric (favors unhindered sites), and stereoelectronic factors (favors sites where strain relief is possible) that distinguish C—H bonds from one another within a molecule. Catalyst 1 relies on the constructive combination of these inherent factors to favor a single site of oxidation within a molecule. While catalyst 1 provides good selectivity in many organic molecules because of the pervasiveness of these inherent reactivity differences among C—H bonds, the substrate ultimately dictates site-selectivity. As a result, site-selectivity suffers when individual factors diverge to favor distinct sites and modulating the magnitude of selectivity or achieving oxidation at alternate sites is not currently possible without chemically changing the substrate (e.g., incorporation of specific functionality that binds to the catalyst and directs oxidation).

Catalyst-controlled selectivity that enhances or overturns the substrate's inherent selectivity preference is still at the forefront in asymmetric catalysis and site-selective modification of reactive functionality. Aliphatic C—H oxidation presents the additional challenge of requiring a catalyst reactive enough to oxidize very inert bonds, yet that maintains the capacity for its control elements to differentiate the subtle features of bonds ubiquitous within organic molecules. Catalyst control is a hallmark of enzymatic aliphatic C—H oxidations. However, despite significant efforts to adopt the enzymatic strategies of utilizing shape and functional group recognition elements, efficient and general small molecule catalyst control in aliphatic C—H oxidations has not yet been achieved. The challenges associated with creating a discrete match between catalyst and substrate have led to extreme catalyst designs, such as the complete encapsulation of the catalyst active site to select on the basis of substrate topology, thereby limiting the scope to one or a few similar substrates. The invention provides a small molecule catalyst that utilizes a trajectory restriction strategy to achieve predictable, catalyst-controlled site-selectivity while maintaining substrate generality.

Figure 1:
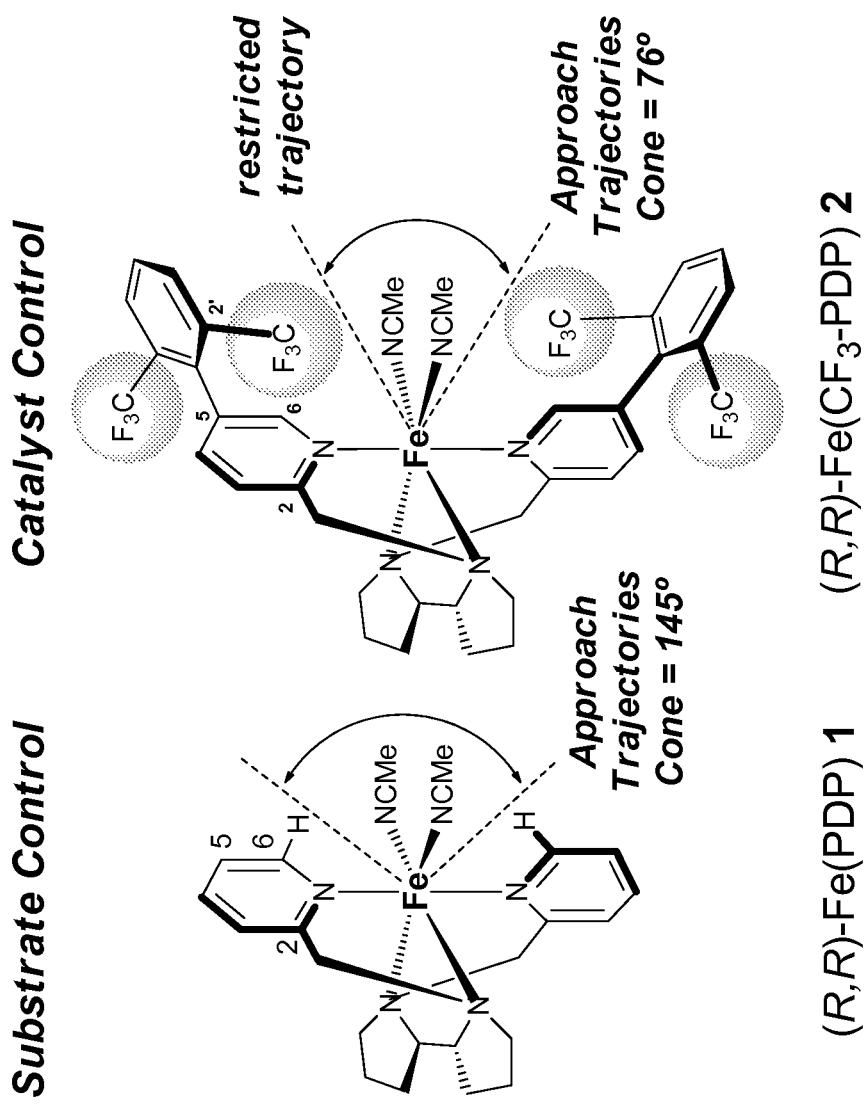
FIG. 1. Substrate control C—H Oxidation Catalyst 1 and Novel C—H Oxidation Catalyst 2, developed using a trajectory restriction strategy.

A small molecule catalyst was sought that would incorporate minimal steric blocking elements to restrict the trajectories of approach of certain C—H bonds to the iron oxo (FIG. 1). Such a catalyst could alter intrinsic substrate bias by rendering catalyst-substrate non-bonding interactions paramount, while maintaining structural flexibility such that substrates of diverse topologies are accommodated. The three-dimensional (3D) structure of (R,R)—Fe (PDP) (1) reveals a wide 145° cone of possible approach trajectories of a substrate to the putative Fe-oxo (cone defined by the innermost edges of the ligand—the pyridine C6 hydrogens—and the iron center as measured from the catalyst crystal structure) so that a combination of electronic and steric/stereoelectronic factors influence site-selectivity variably depending on the substrate.

Modifications at the pyridine 6-position of catalyst 1 were found to suppress reactivity, supporting reports that catalysts with steric hindrance near the oxo exhibit greatly diminished C—H oxidation reactivity (Suzuki, Oldenburg, and Que, Angew. Chem. Int. Ed. 2008, 47, 1887). A catalyst with pendent aryl rings at the 5-position having ortho $CF_3$ groups was then prepared. Ortho $CF_3$ di-substitution was found to be ideal because its electron-withdrawing properties deactivate the ligand towards oxidation and its steric bulk (estimated to be comparable to an isopropyl group, but rotationally symmetric) enforces a perpendicular biaryl alignment wherein the $CF_3$ groups extend toward the catalyst active site and narrow the cone of possible approach trajectories from 145° to 76°.

The ability of Fe($CF_3$-PDP) (2) to alter the intrinsic site-selectivities of oxidation with Fe(PDP) (1) was first examined over a topologically diverse selection of substrates (see Scheme A and FIG. 2). Oxidation of linear ester (+)-3 and trans-1,2-dimethylcyclohexane (6) previously provided poor to moderate selectivity for 2° versus 3° oxidation using (S,S)-1 (entries 1 and 3). Competing sterics (favoring 2° oxidation) and electronics (favoring 3° oxidation) within these substrates led to low site-selectivity based on substrate control.

Scheme A. Catalyst-Controlled Oxidation of Simple Cyclic and Acyclic Molecules.

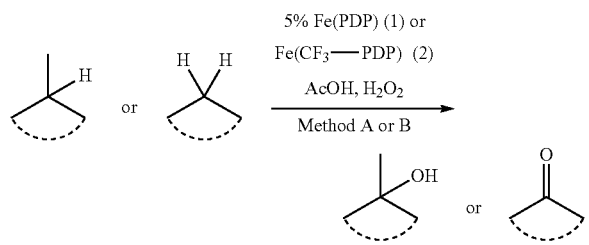

In contrast, catalyst (S,S)-2 diverts reactivity toward the electronically disfavored 2° sites by restricting access of the 3° sites by the active oxidant. The substantial improvement in site-selectivity with catalyst 2 (entries 2 and 4) affords useful levels of 2° oxidation products (51% yield, 70% yield).

In addition to enhancing selectivity in previously poorly selective reactions, an investigation was carried out to determine if catalyst 2 can also completely overturn the substrate's inherent selectivity to favor an alternate site. Oxidation of trans-4-methylcyclohexyl acetate (10) with (S,S)-1 provides selectivity for C4 oxidation based primarily on electronics to afford alcohol 12 in 66% yield (entry 5). Catalyst (S,S)-2 overturns this selectivity by exploiting a significant catalyst-substrate repulsive non-bonding interaction with the C4 axial 3° C—H bond and affords good yields (51%) of mono-oxidized product at the electronically deactivated C3 site (entry 6). Significantly the same effect is observed with a topologically distinct (acyclic) and functionally dense isoleucine substrate [(+)-13]. Oxidation with (R,R)-1 affords 43% of alcohol (+)-15 as the major product (1:2 2°:3°, entry 7); whereas, catalyst (R,R)-2 leads to a turnover of site-selectivity affording the methylene oxidation product, γ-ketone (+)-14, in a preparatively useful 56% yield (4:1 2°:3°, entry 8).

Catalyst-controlled reactivity can further be applied in a more complex dipeptide setting. While (R,R)-1 affords no selectivity for the oxidation of (+)-16 due to competing electronic and steric effects (1:1 2°:3°, entry 9), (R,R)-2 provides 51% yield of norvaline oxidation with excellent 9:1 2°:3° selectivity (entry 10). In contrast to catalyst 1 whose selectivities are dictated by the interplay of electronic and sterics/stereoelectronics within the substrate, catalyst 2 relies primarily on non-bonding interactions between the catalyst and the substrate to control site-selectivities. Significantly, catalyst 2 affects changes in site-selectivity relative 1 under a uniform set of operationally simple reaction conditions (room temperature, open to air, acetonitrile, 0.16 M) in preparatively useful yields (average 54% isolated yield of mono-oxidized product).

To broadly impact synthetic strategy, catalysts that exert control on site-selectivities of oxidation must do so in a predictable way on a diverse range of complex molecules. Structure-based catalyst reactivity models were therefore developed that enable the systematic identification of the most likely sites of oxidation on a molecule and then the quantitative description and prediction of the site-selectivity afforded by each catalyst. To simplify the analysis of complex molecules with many potential sites of oxidation, a site filter was developed that identifies likely sites of oxidation based on parameterization of electronic (E=natural partial atomic charges, NPA, B3LYP/6-311++G(d,p)) and steric/stereoelectronics (S, assigned based on Winstein-Holness values ("A values") (J. Am. Chem. Soc. 1955, 77, 5562), FIG. 3). Details including computational methods, assigning E and S parameters, creating the structure-based catalyst reactivity models as well as catalyst-controlled oxidation of several additional substrates are further described below in Examples 3-8. These values were systematically categorized across all substrates as highly reactive (red), moderately reactive (purple) and unreactive (blue): only sites with either two red or one red and one purple parameter are considered susceptible to oxidation under this filter.

Figure 4:
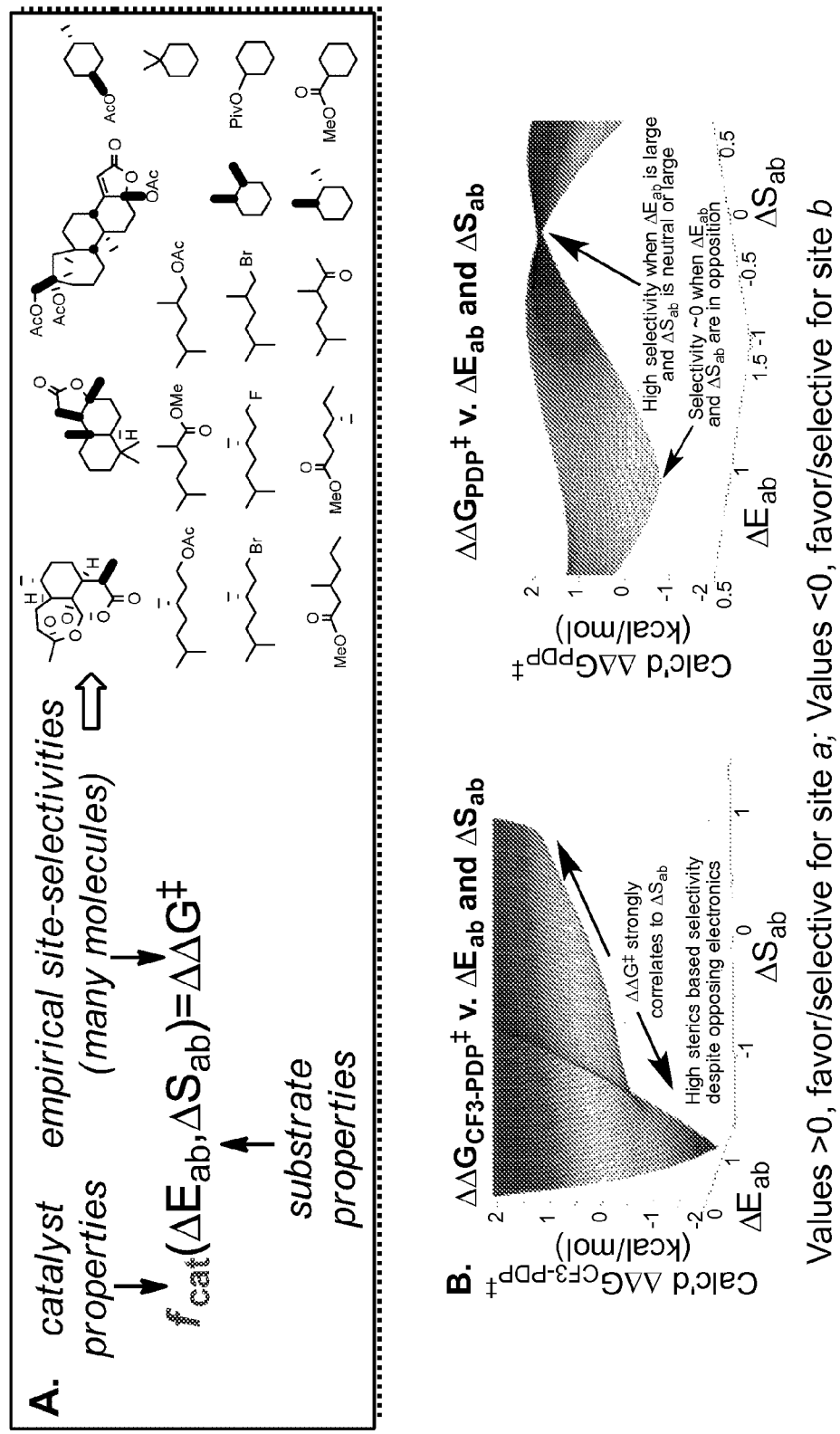
FIG. 4. Structure-Based Catalyst Reactivity Models. (a) Empirical site-selectivity equation; (b) predictive calculation-based reactivity plots; (c) comparison of observed vs. calculated data.
Figure 4:
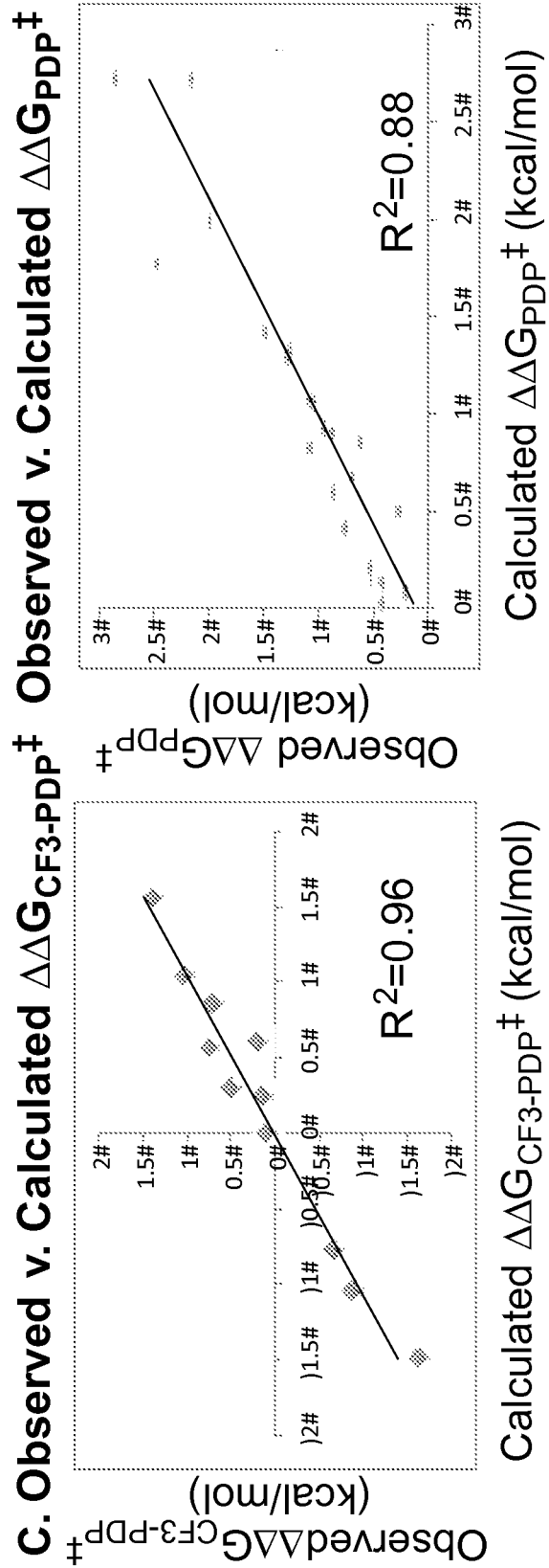

Development of a model was pursued that mathematically relates each catalyst's site-selectivities to the properties of the substrate. An evaluation was carried out to determine if the difference in electronics ($\Delta E_{ab}=E_b-E_a$) and sterics/stereoelectronics ($\Delta S_{ab}=S_b-S_a$), which describe the relative reactivity between the sites identified using the site filter (a and b), could be proportional to the experimentally determined site-selectivities (a:b) expressed as a difference in transition state energies ($\Delta\Delta G^{\ddagger} \approx 1.36 \log(a:b)$). These data were fit as a function of catalyst $f_{cat}(\Delta E_{ab}, \Delta S_{ab})=\Delta\Delta G^{\ddagger}$ to obtain a 3D free energy relationship (Harper and Sigman, Science 2011, 333, 1875) expressed by an equation for each catalyst (FIG. 4 A,B), as described in Example 3 below.

In examining the surface for Fe($CF_3$-PDP) (2) oxidations, site-selectivity (i.e. $\Delta\Delta G^{\ddagger}$, Z-axis) correlates strongly with the $\Delta S_{ab}$ parameter and is highest when there is a large difference in sterics/stereoelectronics between two sites ($\Delta S_{ab}$) in either direction: the difference in electronics ($\Delta E_{ab}$) can be negligible or even large in the opposite direction. The correlations expressed computationally are fully consistent with the empirical observation that Fe($CF_3$-PDP) (2) induces catalyst-controlled changes in $\Delta\Delta G^{\ddagger}$ as a result of non-bonding interactions between the catalyst and the substrate. In contrast the surface for Fe(PDP) (1) oxidations predicts that site-selectivity is highest when electronic and steric/stereoelectronic differences between two sites are large in the same direction. This mathematically expresses the empirical observation that Fe(PDP) (1) oxidations are controlled by the confluence of favorable steric/stereoelectronic and electronic properties within the substrate.

Comparing the calculated $\Delta\Delta G^{\ddagger}$ values with those experimentally derived for catalysts 2 and 1 for all substrates used to create the models provides a good linear fit (FIG. 4C). In addition to further validating the inventors' concept that the basic physical organic chemistry parameters of electronics and sterics/stereoelectronics of a substrate correlate to site-selectivities in C—H oxidation, this finding also demonstrates for the first time that this relationship can be expressed quantitatively and can be varied based on catalyst structure.

Figure 3:
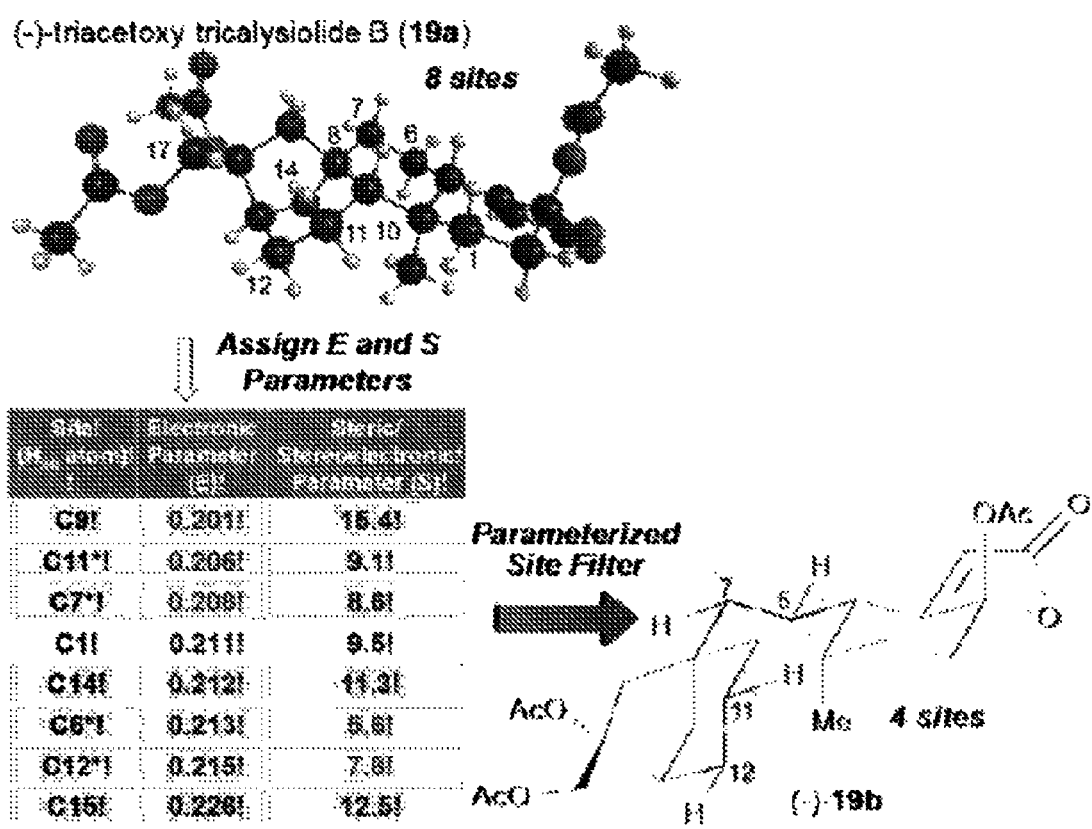
FIG. 3. Parameterized Site Filter for Complex Substrates. Electronic Parameter (E)=NPA partial atomic charge from DFT calculations. Steric/Stereoelectronic Parameter (S)=local+through space–stereoelectronic. Larger E=more positive charge, more electron poor. Larger S=more sterically hindered. Red=highly reactive (from lowest E up to a 5% increase; from lowest S up to a 40% increase); purple=moderately reactive (from the upper limit of the red region up to a 5% increase (E) or 40% increase (S)); blue=unreactive (anything above the upper limit of the purple region). Acetate substituted sites were excluded from analysis.
Figure 5:
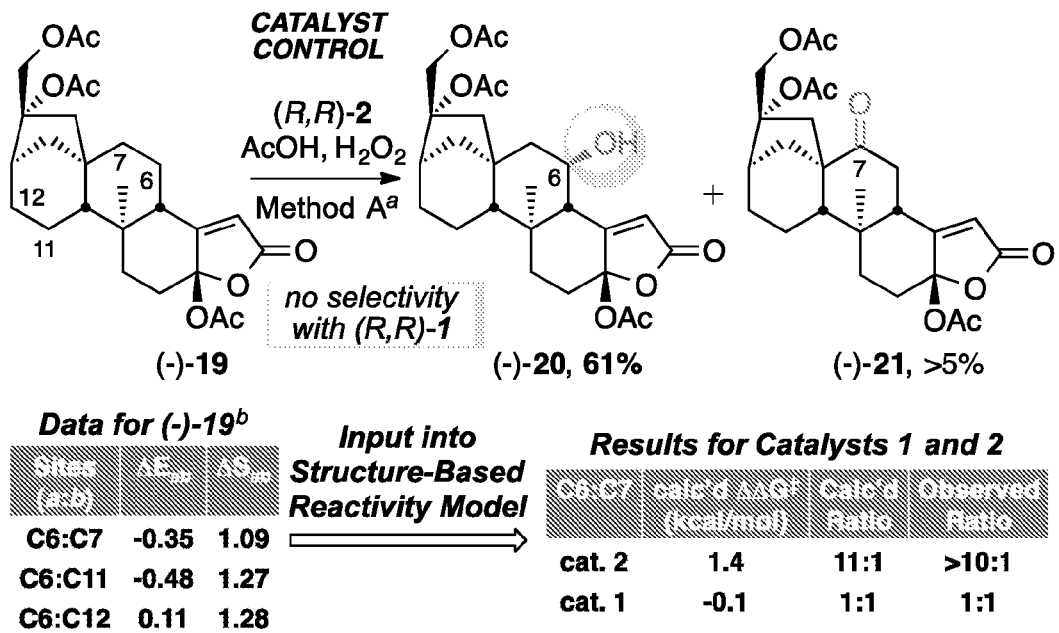
FIG. 5. Influencing Site-Selectivity in a Non-Selective C—H Oxidation. $^a$ Average of three runs, standard deviation=3%. Starting material was recycled 1 time. $^b$ Positive values indicate the parameter favors site a; negative values indicate the parameter favors site b.

The scope of Fe(CF$_3$-PDP) (2)'s ability to alter intrinsic site-selectivities in complex molecule settings as well as the capacity for the structure-based catalyst reactivity models to describe the resulting divergent selectivities was then evaluated. Applying the parameterized site filter to (−)-triacetoxy tricalysiolide B (19), a putative metabolite of the diterpene cafestol found in coffee having eight potential sites of oxidation, revealed four likely sites of oxidation: C6, C7, C11 and C12 (FIGS. 3 and 5). Evaluation of the electronic and steric difference parameters between these sites indicates that the selectivity factors are in opposition; there is a strong steric preference for C6 and an electronic preference for C7 and C11 (FIG. 5). Using C6 as the reference in catalyst 1's reactivity model, moderate site-selectivity ratios of 1:1.1 (C6:C7), 1:1.4 (C6:C11) and 4:1 (C6:C12) were calculated, due to these divergent electronic and steric/stereoelectronic factors within the substrate. These calculated values are fully consistent the experimental findings that oxidation of (−)-19 with (R,R)—Fe(PDP) (1) furnishes (−)-6β-hydroxy-triacetoxy tricalysiolide B (20) in 26% yield and (−)-7-oxo-triacetoxy tricalysiolide B (21) in 18% yield with no site-selectivity (1:1 C6:C7, FIG. 5) and poor mass balance suggesting unselective oxidation at other activated sites (10% recovered starting material).

In contrast, catalyst 2's reactivity model calculates an 11:1 C6:C7 ratio with higher mass balance due to catalyst 2's ability to respond to large steric/stereoelectronic difference parameters ($\Delta S_{6,7}$=1.09, $\Delta S_{6,11}$=1.28, $\Delta S_{6,12}$=1.28). Experimentally, oxidation of (−)-19 with (R,R)-2 affords (−)-20 in a 61% isolated yield with a significant catalyst-dependent increase in site-selectivity of C6:C7 oxidation from 1:1 to >10:1 (FIG. 5). It is significant to note that excellent enhancement of site-selectivity for C6 oxidation with catalyst 2 is observed despite the opposing electronic difference parameter favoring C7. Additionally, steric hindrance in the substrate can retard overoxidation of 2° alcohols to ketones with catalyst 2, which effects are not found with catalyst 1.

Figure 6:
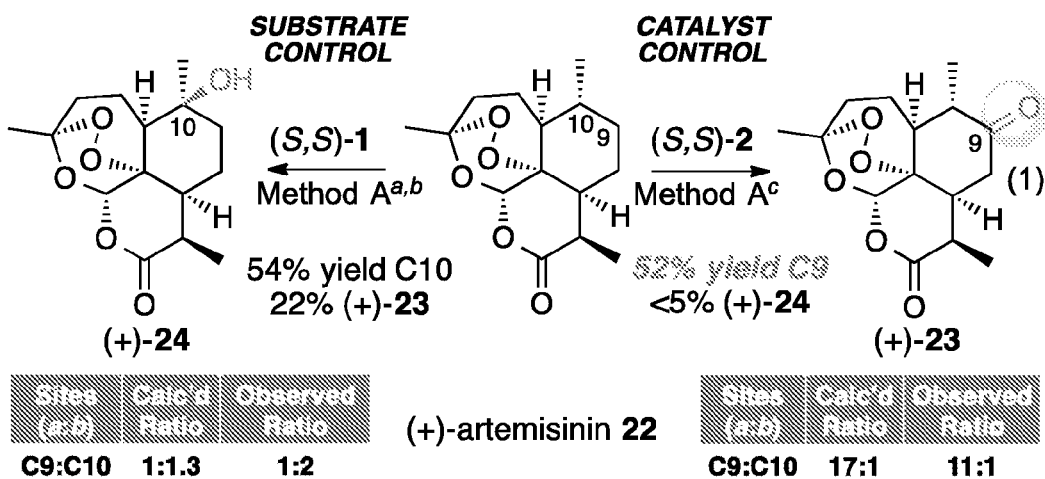
FIG. 6. Overriding Inherent Site-Selectivity of C—H Oxidation. $^a$ Average of three runs. $^b$ Starting material was recycled two times. Starting material was recycled four times. Standard deviation=2%.

The greatest challenge for catalyst control is to override the inherent site-selectivity of oxidation to favor an alternate site. Catalyst 2 achieved this in the oxidation of simple substrates 10 and (+)-13. The catalyst was next further challenged in a complex molecule setting. Applying the parameterized site filter to (+)-artemisinin (22), having nine potential sites of oxidation, eliminates all but C10 and C9 on the basis of very unfavorable electronics and/or sterics at alternate sites. Catalyst 1 is calculated to give a 1.3:1 C10:C9 ratio because it responds to the divergent biasing factors within the substrate: a strong electronic preference for 3° oxidation at C10 ($\Delta E_{10,9}$=1.48) and an opposing steric preference for 2° oxidation at C9 ($\Delta S_{10,9}$=−1.70), as further described in Example 6 below. Consistent with this, oxidation of (+)-22 with (S,S)-1 afforded 54% yield of (+)-10β-hydroxy-artemisinin (24) with 23% yield of (+)-9-oxo-artemisinin (23) in a useful 2:1 C10:C9 selectivity (FIG. 6).

Despite the substrate's strong electronic bias favoring C10 oxidation, the structure-based reactivity model for catalyst 2 calculates a 17:1 ratio favoring C9 oxidation based on the large steric difference parameter. This may be understood on the basis of catalyst 2's ability to exploit non-bonding interactions between its biaryl ligand and the substrate's rigid lactone ring system to restrict approach trajectories of the electron rich C10 C—H bond to the iron oxo. Gratifyingly, (S,S)-2 dramatically turns over the substrate controlled selectivity of (S,S)-1, oxidizing at the C9 site in an 11:1 C9:C10 ratio and furnishing 52% yield of (+)-23 and <5% (+)-24 (FIG. 6).

Catalyst 2's ability to override strong electronic substrate bias in oxidations by exploiting non-bonding catalyst-substrate interactions is analogous to what was observed with (−)-triacetoxy tricalysiolide B (19), but on a topologically distinct structure. See Example 5 below. Notably, previous to this work, only P-450 enzymes evolved in the laboratory specifically for the oxidation of (+)-22 have provided comparable levels of selectivity for C9 (Zhang et al., *J. Am. Chem. Soc.* 2012, 134, 18695), highlighting the power of catalyst 2 to access new sites of reactivity without the need for substrate specificity.

Models for catalysts 1 and 2 are strongly supported by the empirical data for substrates incorporated into the original data sets. The predictive power of these models was then tested using (+)-nectaryl derivative (25), a synthetic terpene-like molecule used in commercial fragrances that had not been included in the data sets for either catalyst. Applying the parameterized site filter, many likely sites of oxidation remained (C11, C10/12, C9/13, C8, C7 and C3): the conformational flexibility of (+)-25 and electronic similarity of its sites made selective oxidation with either catalyst a challenging prospect.

Aliphatic C—H oxidations of (+)-25 were predicted using the structure-based reactivity models to modestly favor the more electron rich, tertiary C11 site with catalyst 1 (1.5:1) and the least sterically encumbered C10/12 site (3:1) for catalyst 2 (FIG. 7), as further described in Example 7 below. Consistent with this calculation, oxidation of (+)-25 with (S,S)-1 affords 29% yield of C11 hydroxyl (+)-27 and 23% yield of the C10/12 ketones 26 with poor selectivity slightly favoring oxidation at the electronically activated C11 site (1.3:1). In contrast, catalyst (S,S)-2 is able to overcome the electronic substrate bias towards C11 to furnish C10/12 oxidation products 26 in a 52% yield with good selectivity (6:1). This set of experiments illustrates catalyst 2's capacity to affect predictable control on site-selectivity based on non-bonding interactions, even in complex substrates with high degrees of conformational flexibility. Moreover, the site-selectivity models for catalysts 1 and 2 are validated as predictive tools, particularly for substrates whose electronic, steric, and stereoelectronic features are well represented by the substrates incorporated into the original data sets.

These results show that catalyst control of site-selectivity in aliphatic C—H oxidations is possible—despite the significant challenges associated with controlling highly reactive intermediates—without necessitating a specific match between one catalyst and one substrate. The development of quantitative structure-based catalyst reactivity models can provide more targeted application of C—H oxidations at late stages of complex molecule synthesis and enable site-divergent diversification of bioactive molecules. Furthermore, the discovery that site-selectivities of oxidation can be mathematically correlated to substrate properties as a function of the catalyst can thus be used for catalyst design for site-selective intermolecular C—H oxidations.

Thus, the invention makes use of the discovery that site-selective sp$^3$ C—H bond oxidation can be predictably controlled in the presence of a sterically bulky and electrophilic complex, such as a complex that has a restricted approach trajectory with respect to the central iron atom. The novel class of complexes can use H$_2$O$_2$, an inexpensive and environmentally friendly oxidant, to effect highly selective oxidations of unactivated sp$^3$ C—H bonds over a broad range of substrates. The site of oxidation with the complexes can be predicted, based on the electronic and/or steric environment of the C—H bond. In addition, the oxidation reaction does not require the presence of directing groups in the substrate. Thus, the sp$^3$ C—H oxidation reaction can be used in a predictable fashion on intricate small molecule substrates to furnish oxidized products in preparatively useful yields.

A composition for selective sp$^3$ C—H bond oxidation can include a complex of iron and a tetradentate ligand (e.g., the ligand of Formula (I)). The tetradentate ligand binds to the metal through four separate atoms, each of which independently may be a heteroatom such as nitrogen. Preferably at least one of the binding atoms in the ligand is nitrogen, and more preferably all four binding atoms in the ligand are nitrogen atoms. The complex can include at least one ancillary ligand for the iron, and may include one or more counterions.

In one example, a composition for selective sp$^3$ C—H bond oxidation may include an iron complex, a tetradentate ligand, at least one ancillary ligand, and a counterion, where the tetradentate ligand includes a bis((5-(2,6-bis(trifluoromethyl)phenyl)pyridin-2-yl)methyl)-2,2'-bipyrrolidine tetradentate ligand, or a similar tetradentate ligand having two (2,6-bis(trifluoromethyl)phenyl)pyridin-2-yl groups. Each pyridyl group can be independently substituted with one or more substituent groups, one of which is a group linking the pyridyl ring (e.g., at the pyridyl 2-position) to an amine nitrogen (e.g., the nitrogen of a pyrrolidine group). At least one amine nitrogen in the group can be part of a heterocyclic group such as a pyrrolidine. If each amine nitrogen in the group is part of a heterocyclic group, then the group may be referred to as a N,N'-bis(heterocyclic)-N,N'-bis(pyridyl)-ethane-1,2-diamine group.

In another example, a composition for selective sp$^3$ C—H bond oxidation includes a complex of Formula (I) where $L^1$ and $L^2$ are ancillary ligands; X is a counterion; n is 2 or 3; $R^1$, $R^2$, $R^7$ and $R^8$ independently are an alkyl group, a heteroalkyl group, an aryl group or a heteroaryl group; and $R^3$, $R^4$, $R^5$ and $R^6$ independently are hydrogen (—H), a halide group, an alkyl group, a heteroalkyl group, an aryl group or a heteroaryl group. The superscripts "A" and "B" for $C^A$, $C^B$, $N^A$ and $N^B$ are used simply to identify which carbon and nitrogen atoms are included in a group within the structural formula. $C^A$ and $N^A$, in combination with $R^1$ and $R^3$, with $R^1$ and $R^4$, with $R^2$ and $R^3$, and/or with $R^2$ and $R^4$, can form at least one ring (i.e., a heteroalkyl group). Additionally or alternatively, $C^B$ and $N^B$, in combination with $R^8$ and $R^6$, with $R^8$ and $R^5$, with $R^7$ and $R^6$, and/or with $R^7$ and $R^5$, can form at least one ring (i.e., a heteroalkyl group).

The ancillary ligands $L^1$ and $L^2$ independently may be solvent molecules with a lone pair of electrons, for example, acetone, acetonitrile, or a μ-oxo bridge to another metal; or $L^1$ and $L^2$ together may be a single ligand, such as a carboxylate group, a diketone or a diamine. If one of $L^1$ and $L^2$ is a μ-oxo bridge to another metal, then the other of $L^1$ and $L^2$ preferably bridges the two metals also, either as another μ-oxo bridge, or as an organic bridge such as acetone, acetonitrile or a divalent ligand. Preferably $L^1$ and $L^2$ independently are acetonitrile or a μ-oxo bridge.

The counterion X may be any suitable anion. Examples of counterions include but are not limited to $Cl^-$, $Br^-$, $AcO^-$, $TfO^-$, $CF_3CO_2^-$, $BF_4^-$, $ClO_4^-$, $ReO_4^-$, $AsF_6^-$, and $SbF_6^-$. The complex may include two or three counterions. The complex may further include a counterion that is present as a salt with a cation, providing an in situ anion exchange reagent. Examples of cations that may be present in a salt include $Na^+$, $Li^+$, $K^+$, $Cs^+$ and $Ag^+$.

The groups $R^1$, $R^2$, $R^7$ and $R^8$ independently are an alkyl group, a heteroalkyl group, an aryl group or a heteroaryl group. If $R^1$, $R^2$, $R^7$ or $R^8$ is an alkyl group or a heteroalkyl group, the group preferably includes from 1 to 20 carbon atoms, and more preferably includes from 1 to 10 carbon atoms, from 1 to 5 carbon atoms, from 1 to 3 carbon atoms, or from 1 to 2 carbon atoms (e.g., a methylene or ethylene group). If $R^1$, $R^2$, $R^7$ or $R^8$ is an aryl group or a heteroaryl group, the group preferably includes from 5 to 20 carbon atoms, and more preferably includes from 5 to 12 carbon atoms, from 5 to 10 carbon atoms, from 5 to 9 carbon atoms, or from 5 to 6 carbon atoms.

$R^1$ may be —C($R^{1a}$)($R^{1b}$)—, where the $R^{1a}$ and $R^{1b}$ groups independently may be hydrogen, a halide group, an alkyl group, a heteroalkyl group, an aryl group or a heteroaryl group. At least one of $R^{1a}$ and $R^{1b}$ may be part of a ring. $R^2$ preferably is —$CH_3$, or is part of a ring.

$R^7$ preferably is —$CH_3$, or is part of a ring. $R^8$ may be —C($R^{8a}$)($R^{8b}$)—, where the $R^{8a}$ and $R^{8b}$ groups independently may be hydrogen, a halide group, an alkyl group, a heteroalkyl group, an aryl group or a heteroaryl group. At least one of $R^{8a}$ and $R^{8b}$ may be part of a ring.

The groups $R^3$, $R^4$, $R^5$ and $R^6$ independently are hydrogen, a halide group, an alkyl group, a heteroalkyl group, an aryl group or a heteroaryl group. If $R^3$, $R^4$, $R^5$ or $R^6$ is an alkyl group or a heteroalkyl group, the group preferably includes from 1 to 20 carbon atoms, and more preferably includes from 1 to 10 carbon atoms, from 1 to 5 carbon atoms, from 1 to 3 carbon atoms, or from 1 to 2 carbon atoms. If $R^3$, $R^4$, $R^5$ or $R^6$ is an aryl group or a heteroaryl group, the group preferably includes from 5 to 20 carbon atoms, and more preferably includes from 5 to 12 carbon atoms, from 5 to 10 carbon atoms, from 5 to 9 carbon atoms, or from 5 to 6 carbon atoms.

$R^3$ preferably is hydrogen or an alkyl group. More preferably, $R^3$ is an alkyl group that is part of a cycloalkyl ring or heterocycloalkyl ring, which is preferably a 5-membered ring. $R^4$ preferably is hydrogen or an alkyl group. More preferably, $R^4$ is an alkyl group that is part of a cycloalkyl ring or heterocycloalkyl ring, which is preferably a 5-membered ring. $R^5$ preferably is hydrogen or an alkyl group. More preferably, $R^5$ is an alkyl group that is part of a cycloalkyl ring or heterocycloalkyl ring, which is preferably a 5-membered ring. $R^6$ preferably is hydrogen or an alkyl group. More preferably, $R^6$ is an alkyl group that is part of a cycloalkyl ring or heterocycloalkyl ring, which is preferably a 5-membered ring.

As noted above, $C^A$ and $N^A$, in combination with $R^1$ and $R^3$, with $R^1$ and $R^4$, with $R^2$ and $R^3$, and/or with $R^2$ and $R^4$, form at least one ring. For example, $C^A$ and $N^A$ may form two rings, in which the $C^A$—$N^A$ bond is part of both rings. Likewise, $C^B$ and $N^B$, in combination with $R^8$ and $R^6$, with $R^8$ and $R^5$, with $R^7$ and $R^6$, and/or with $R^7$ and $R^5$, may form at least one ring. These rings independently may be heterocycloalkyl groups or heteroaryl groups, and may be substituted with one or more substituent groups. These rings independently may have from 4 to 20 ring atoms, preferably from 5 to 12 ring atoms, more preferably from 5 to 10 ring atoms, more preferably from 5 to 9 ring atoms, and more preferably from 5 to 6 ring atoms.

Similarly, $C^A$ and $C^B$, in combination with $R^3$ and $R^5$, with $R^4$ and $R^6$, with $R^4$ and $R^5$, and/or with $R^3$ and $R^6$, may form at least one ring. These rings independently may be cycloalkyl groups, heterocycloalkyl groups, aryl groups or heteroaryl groups, and may be substituted with one or more substituent groups. These rings independently may have from 4 to 20 ring atoms, preferably from 5 to 12 ring atoms, more preferably from 5 to 10 ring atoms, more preferably from 5 to 9 ring atoms, and more preferably from 5 to 6 ring atoms.

In one embodiment, the pyridyl rings of the tetradentate ligands are substituted with phenyl groups having two or three trifluoromethyl groups. The trifluoromethyl groups can be located ortho, meta, or para to the bond connecting the phenyl group to the pyridyl group. Preferably, at least one, or at least two, of the trifluoromethyl groups are ortho to the bond connecting the phenyl group to the pyridyl group. More preferably, the phenyl groups are bis-trifluoromethyl-phenyl groups, such as 2,6-bis(trifluoromethyl)phenyls.

The pyridyl groups to which the trifluoromethyl-substituted phenyl groups are bonded may independently be substituted with one or more other substituent groups, such as a halide group, a nitro group, an alkyl group, a heteroalkyl group, an aryl group, a heteroaryl group, or a combination thereof.

In another embodiment, the pyridyl rings of the tetradentate ligands are substituted with alkyl groups (and not phenyl groups), such as methyl, ethyl, propyl, or isopropyl groups (e.g., a "DMPDP" ligand).

The tetradentate ligand in Formula (I) can be an N-heterocyclic-N,N'-bis(pyridyl)-ethane-1,2-diamine ligand. The ring including $C^A$ and $N^A$ can be a heterocyclic ring such as a pyrrolidine ring. Thus, the pyridine ring substituted with substituent groups $R^1$ and the trifluoromethyl-substituted phenyl is one pyridyl group, and the pyridine ring substituted with substituent groups $R^8$ and the trifluoromethyl-substituted phenyl is another pyridyl group.

In one example of a complex of Formula (I), $N^A$, $C^A$, $R^2$ and $R^4$ form a 5-membered heterocycloalkyl ring; and $N^B$, $C^B$, $R^5$ and $R^7$ form a 5-membered heterocycloalkyl ring. Such a complex, for example, may be a complex of Formula (II). In one embodiment, $R^1$ and $R^8$ are —$CH_2$—; $R^3$, $R^6$, $R^9$ and $R^{10}$ are hydrogen; $N^A$, $C^A$, $R^2$ and $R^4$ form a 5-membered heterocycloalkyl ring; $N^B$, $C^B$, $R^5$ and $R^7$ form a 5-membered heterocycloalkyl ring; and $L^1$, $L^2$, X and n are as defined for Formula (I), to provide a complex of Formula (II):

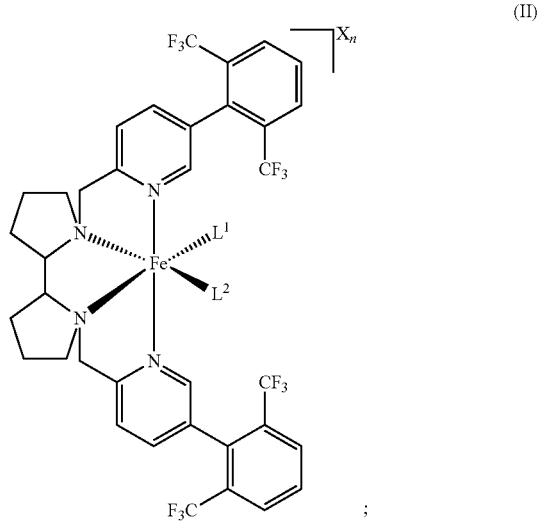

(II)

or the tri(trifluoro) variation thereof (Formula (IIB)). The tetradentate ligand in this complex is referred to as a (−)-2-((2-(1-(pyridin-2-ylmethyl)pyrrolidin-2-yl)pyrrolidin-1-yl)methyl)pyridine ligand, which may be abbreviated as Fe(CF$_3$-PDP); the tri(trifluoro) variation can be abbreviated Fe(tri-CF$_3$-PDP). In some embodiments, the ligand may be in the (S,S) enantiomeric form, it may be in the (R,R) enantiomeric form, or combinations of the enantiomers may be present.

In another example of a complex of Formula (I), $N^A$, $C^A$, $R^1$ and $R^3$ form a 5-membered heterocycloalkyl ring; and $N^B$, $C^B$, $R^6$ and $R^8$ form a 5-membered heterocycloalkyl ring. Such a complex, for example, may have structural Formula (III), in which $N^A$, $C^A$, $R^1$ and $R^3$ form a 5-membered heterocycloalkyl ring; $N^B$, $C^B$, $R^6$ and $R^8$ form a 5-membered heterocycloalkyl ring; $R^2$ and $R^7$ are —$CH_3$; $R^4$ and $R^5$ are hydrogen; each $R^X$ is 2,6-bis(trifluoromethyl)phenyl or 2,4,6-tris(trifluoromethyl)phenyl; and $L^1$, $L^2$, X and n are as defined for Formula (I):

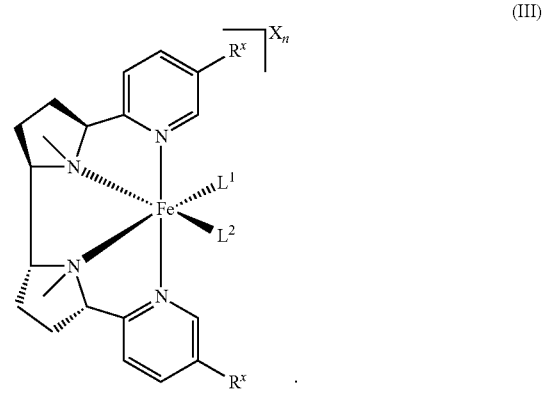

(III)

In another example of a complex of Formula (I), $N^A$, $C^A$, $R^2$ and $R^4$ form a 5-membered heterocycloalkyl ring; and $N^B$, $C^B$, $R^5$ and $R^8$ form a 5-membered heterocycloalkyl ring. Such a complex, for example, may have structural formula (W), in which $R^1$ is —$CH_2$—; $N^A$, $C^A$, $R^2$ and $R^4$ form a 5-membered heterocycloalkyl ring; $N^B$, $C^B$, $R^5$ and $R^8$ form a 5-membered heterocycloalkyl ring; $R^7$ is —$CH_3$; $R^3$ and $R^6$ are hydrogen; each $R^X$ is 2,6-bis(trifluoromethyl) phenyl; and $L^1$, $L^2$, X and n are as defined for structural Formula (I). The asterisks indicate stereogenic carbons.

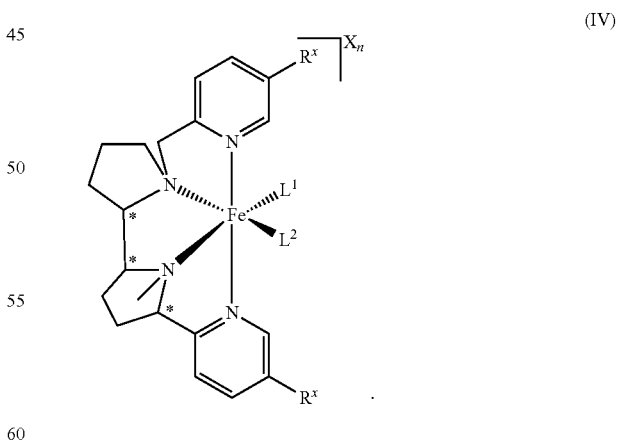

(IV)

In another example of a complex of Formula (I), $N^A$, $C^A$, $R^2$ and $R^4$ form a 5-membered heterocycloalkyl ring; $C^A$, $C^B$, $R^3$ and $R^5$ form a 5-membered cycloalkyl ring; and $N^B$, $C^B$, $R^5$ and $R^7$ form a 5-membered heterocycloalkyl ring. Such a complex, for example, may have structural Formula (V), in which $R^1$ and $R^8$ are —$CH_2$—; $N^A$, $C^A$, $R^2$ and $R^4$ form a 5-membered heterocycloalkyl ring; $C^A$, $C^B$, $R^3$ and $R^5$ form a 5-membered cycloalkyl ring; $N^B$, $C^B$, $R^5$ and $R^7$ form a 5-membered heterocycloalkyl ring; $R^6$ is hydrogen; each $R^X$ is 2,6-bis(trifluoromethyl)phenyl; and $L^1$, $L^2$, X and n are as defined for structural Formula (I).

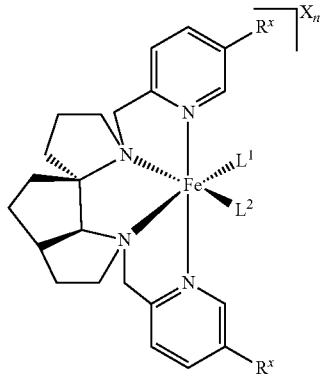

(V)

In another example of a complex of Formula (I), $N^A$, $C^A$, $R^2$ and $R^4$ form a 5-membered $C^B$, heterocycloalkyl ring; $C^A$, $C^B$, $R^4$ and $R^6$ form a 5-membered cycloalkyl ring; $C^A$, $C^B$, $R^3$ and $R^5$ form a 5-membered cycloalkyl ring; and $N^B$, $C^B$, $R^5$ and $R^7$ form a 5-membered heterocycloalkyl ring. Such a complex, for example, may have structural Formula (VI), in which $R^1$ and $R^8$ are —$CH_2$—; $N^A$, $C^A$, $R^2$ and $C^B$, $R^4$ form a 5-membered heterocycloalkyl ring; $C^A$, $C^B$, $R^4$ and $R^6$ form a 5-membered cycloalkyl ring; $C^A$, $C^B$, $R^3$ and $R^5$ form a 5-membered cycloalkyl ring; $N^B$, $C^B$, $R^5$ and $R^7$ form a 5-membered heterocycloalkyl ring; each $R^X$ is 2,6-bis(trifluoromethyl)phenyl; and $L^1$, $L^2$, X and n are as defined for structural Formula (I).

(VI)

In another example of a complex of Formula (I), $N^A$, $C^A$, $R^1$ and $R^4$ form a 5-membered heterocycloalkyl ring; $N^A$, $C^A$, $R^2$ and $R^3$ form a 5-membered heterocycloalkyl ring; $C^A$, $C^B$, $R^4$ and $R^6$ form a 5-membered cycloalkyl ring; $C^A$, $C^B$, $R^3$ and $R^5$ form a 5-membered cycloalkyl ring; $N^B$, $C^B$, $R^5$ and $R^8$ form a 5-membered heterocycloalkyl ring; and $N^B$, $C^B$, $R^6$ and $R^7$ form a 5-membered heterocycloalkyl ring. Such a complex, for example, may have structural Formula (VII), in which $N^A$, $C^A$, $R^1$ and $R^4$ form a 5-membered heterocycloalkyl ring; $N^A$, $C^A$, $R^2$ and $R^3$ form a 5-membered heterocycloalkyl ring; $C^A$, $C^B$, $R^4$ and $R^6$ form a 5-membered cycloalkyl ring; $C^A$, $C^B$, $R^3$ and $R^5$ form a 5-membered cycloalkyl ring; $N^B$, $C^B$, $R^5$ and $R^8$ form a 5-membered heterocycloalkyl ring; $N^B$, $C^B$, $R^6$ and $R^7$ form a 5-membered heterocycloalkyl ring; each $R^X$ is 2,6-bis(trifluoromethyl)phenyl; and $L^1$, $L^2$, X and n are as defined for structural Formula (I).

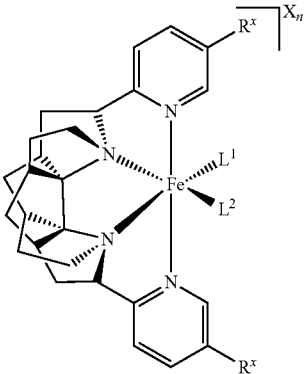

(VII)

In each of the above structural formulas, the complex may be in the form as shown, or the complex may be in an enantiomeric form, or in a combination thereof, or in a diastereomeric form. A composition for selective sp³ C—H bond oxidation may include a single enantiomer of a complex, or it may include a mixture of enantiomers and/or diastereomers of the complex. In one embodiment, the complex of Formula (I) is an (S,S) enantiomer, for example, with respect to the two chiral nitrogen atoms complexed with iron. In another embodiment, the complex of Formula (I) is an (R,R) enantiomer.

In one embodiment, $R^1$, $R^2$, $R^7$ and $R^8$ are each independently an alkyl group, and $R^3$, $R^4$, $R^5$ and $R^6$ are each independently hydrogen or alkyl. In some embodiments, $C^B$ and $N^B$, together with at least one pair of groups selected from the group consisting of $R^8$ and $R^6$, $R^8$ and $R^5$, $R^7$ and $R^6$, and $R^7$ and $R^5$, form at least one ring. In various embodiments, $C^A$ and $C^B$, together with at least one pair of groups selected from the group consisting of $R^3$ and $R^5$, $R^4$ and $R^6$, $R^4$ and $R^5$, and $R^3$ and $R^6$, form at least one ring. The compositions comprising a formula described herein can include an oxidant. In various embodiments, the oxidant is a suitable and effective oxidant such as hydrogen peroxide, ozone, a peracid, an alkyl hydroperoxide, or a periodinane.

In some specific embodiments, the composition includes a complex of Formula (I), where the complex of Formula (I) is a complex of Formula (II):

(II)

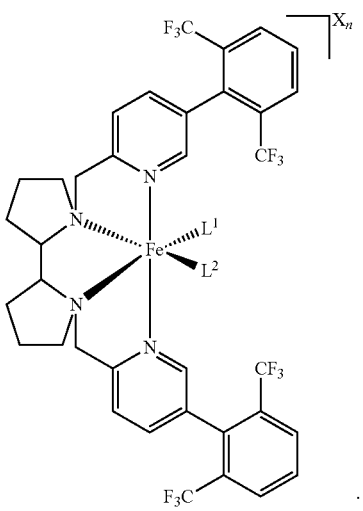

In other specific embodiments, the composition includes a complex of Formula (I), where the complex of Formula (I) is a complex of Formula (IIB):

(IIB)

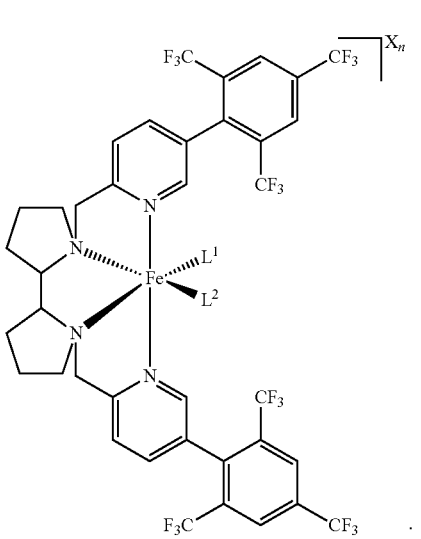

X can be $SbF_6^-$; n can be 2; and $L^1$ and $L^2$ can be ancillary ligands such as acetonitrile. The complex of Formulas (II) and/or (IIB) can be the (S,S) enantiomer, or alternatively, the (R,R) enantiomer.

A complex of Formula (I) can have a restricted approach trajectory, with respect to the central iron atom, thereby providing predictable, catalyst-controlled site-selectivity while maintaining substrate generality. For example, in one embodiment, the restricted approach trajectory to the iron atom can be less than about 135°. In another embodiment, the restricted approach trajectory can be less than about 130°, less than about 125°, less than about 120°, less than about 110°, less than about 100°, less than about 95°, less than about 85°, or less than about 80°, for example, as determined by examination of X-ray crystallographic data. In various embodiments, the restricted approach trajectory to the iron atom can be at least about 60°, at least about 65°, at least about 70°, or at least about 75°.

A composition for selective sp³ C—H bond oxidation may be used to introduce an oxidized functionality, such as a hydroxyl group or an oxo group, into a molecule. A method of oxidizing a substrate may include reacting a substrate and an oxidant in a first reaction mixture that includes a composition that includes a formula described herein, and providing an oxidized product in the first reaction mixture. The first reaction mixture may include a solvent and/or at least one additive. The oxidized product may include an oxidized functionality that was not present in the substrate. The method may optionally include collecting unoxidized substrate from the first reaction mixture, reacting the unoxidized substrate with an oxidant in a second reaction mixture that includes the composition, and providing the oxidized product in the second reaction mixture. The method optionally may include repeating, at least once, collecting unoxidized substrate, reacting the unoxidized substrate with the oxidant in a supplemental reaction mixture that includes the composition, and providing the oxidized product in the supplemental reaction mixture. The second reaction mixture and/or a supplemental reaction mixture independently may include a solvent and/or at least one additive.

The substrate may be any molecule that includes at least one sp³ C—H bond. The substrate may be free of directing groups conventionally required for selective oxidation. The site on the substrate at which oxidation will occur may be predicted, based on the electronic and/or steric environment of the C—H bond.

The oxidant may be, for example, hydrogen peroxide ($H_2O_2$), ozone ($O_3$), a peracid, an alkyl hydroperoxide, or a periodinane. Examples of peracids include peracetic acid, m-chloroperbenzoic acid (mCPBA), and potassium peroxymonosulfate. Examples of alkyl hydroperoxides include t-butyl hydroperoxide and cumene hydroperoxide. Examples of periodinanes include iodosylbenzene ($C_6H_5$—I=O) and iodosobenzene diacetate ($C_6H_5I(OOCCH_3)_2$). In one embodiment the oxidant is $H_2O_2$.

Examples of suitable organic solvents include toluene, acetonitrile, ethyl acetate, acetone and nitromethane. Preferably the solvent includes toluene or acetonitrile, either alone or as a mixture with ethyl acetate, acetone and/or nitromethane. Preferably the solvent is at least 50% by volume toluene or acetonitrile, and can be up to 100% toluene or acetonitrile, or the solvent can be toluene or acetonitrile.

Examples of optional additives include alkyl carboxylic acids, such as formic acid, acetic acid, propionic acid, butyric acid, valeric acid, capric acid, oxalic acid, malonic acid, succinic acid, and glutaric acid.

The reacting may include forming the first reaction mixture where the first reaction mixture can include the substrate, the oxidant and the iron catalyst described herein, and may include a solvent and/or at least one additive. In one example, the reacting includes combining ingredients to form the first reaction mixture. The ingredients can include the substrate, the oxidant and the iron catalyst, and may include a solvent and/or at least one additive. In another example, the reacting includes combining the substrate, the iron catalyst, the solvent and optionally an additive to form a first mixture, and then adding an oxidant mixture, including the oxidant and the solvent, to the first mixture to form the first reaction mixture. Preferably the oxidant mixture is added gradually, such as by a dropwise addition.

In one example, the reacting may further include adding a first supplemental composition mixture to the first reaction mixture, and then adding a first supplemental oxidant mixture to the first reaction mixture. The first supplemental composition mixture can include the iron catalyst, the solvent, and optionally an additive. The first supplemental oxidant mixture can include the oxidant and the solvent. Preferably the first supplemental oxidant mixture is added gradually, such as by a dropwise addition.

The reacting may further include adding a second supplemental composition mixture to the first reaction mixture, and then adding a second supplemental oxidant mixture to the first reaction mixture. The second supplemental composition mixture can include the iron catalyst, the solvent, and optionally an additive. The second supplemental oxidant mixture can include the oxidant and the solvent. Preferably the second supplemental oxidant mixture is added gradually, such as by a dropwise addition. Forming a first reaction mixture, followed by adding a first supplemental composition mixture and a first supplemental oxidant mixture, further followed by adding a second supplemental composition mixture and a second supplemental oxidant mixture, is referred to as a "three-fold reagent addition procedure".

The adding an oxidant mixture, adding a first supplemental oxidant mixture, and adding a second supplemental oxidant mixture independently may be performed gradually. Preferably the time elapsed during the addition of one or more of these mixtures is from about 10 seconds to about 10 minutes. More preferably the time elapsed during the addition of one or more of these mixtures is from 20 seconds to 5 minutes, more preferably from 30 seconds to 2 minutes, and more preferably from 45 to 75 seconds. Preferably the addition of the oxidant mixture and of the first and second supplemental oxidant mixtures includes a dropwise addition of the appropriate oxidant mixture.

The reaction time may be from 30 seconds to 2 hours per addition of reagents. Thus, the initial first reaction mixture may be maintained for 30 seconds to 2 hours before the first supplemental composition mixture and the first supplemental oxidant mixture are added, and then the first reaction mixture may be maintained for an additional 30 seconds to 2 hours before the second supplemental composition mixture and the second supplemental oxidant mixture are added. Preferably the reaction time is from 3 to 60 minutes per addition of reagents. For an oxidation that includes a three-fold reagent addition procedure, the total reaction time may be from 1.5 minutes to 6 hours, including from 9 minutes to 3 hours, from 15 minutes to 1 hour, and from 20 to 45 minutes.

The reacting may include maintaining the first reaction mixture at any suitable and effective temperature, for example, a temperature of from about −40 to about 36° C. Preferably the reaction temperature is from −10 to 35° C. More preferably the reaction temperature is from 5 to 30° C. The reaction temperature may be ambient temperature, e.g., about 20 to about 30° C., or about 22-25° C.

In an example of an oxidation method that includes a three-fold reagent addition procedure, a first mixture contains a substrate, the complex of Formula (I), a solvent and optionally an additive. The substrate can be present at a concentration of from 0.1 to 2 M, the complex can be present at a level of from about 0.1 to 15 mol % relative to the substrate, and the additive, when present, can be present at a level of from 0.1 to 1 equivalent relative to the substrate. An oxidant mixture can also include an oxidant and a solvent, at an oxidant concentration of from 0.05 to 0.5 M. The oxidant mixture can be added dropwise to the first mixture over a period of from 45 to 75 seconds, to form the reaction mixture. The amount of oxidant can be from 1 to 2 equivalents relative to the substrate. After the mixture has been stirred for 30 seconds to 2 hours, for example, at a temperature of from −20 to 36° C., a first supplemental composition mixture can be added, followed by the gradual addition of a first supplemental oxidant mixture. The first supplemental composition mixture can include from 1 to 15 mol % of the complex in the solvent (0.01 to 0.1 M), and from 0.1 to 1 equivalent of the additive. The first supplemental oxidant mixture can include from 1 to 2 equivalents of the oxidant in the solvent (0.05 to 0.5 M). After the mixture has been stirred for 30 seconds to 2 hours, a second supplemental composition mixture can be added, followed by the gradual addition of a second supplemental oxidant mixture. The second supplemental composition mixture and the second supplemental oxidant mixture can be as described for the first supplemental composition mixture and the first supplemental oxidant mixture, respectively.

In another example, the substrate can be reacted with an iron catalyst and an oxidant using a three-fold reagent addition procedure, and the resulting reaction mixture includes an oxidized product and unoxidized substrate. At least a portion of the unoxidized substrate can be collected from the reaction mixture. The collected unoxidized substrate can then be reacted with the composition and the oxidant through another three-fold reagent addition procedure. The collection and subsequent reaction of unoxidized substrate is referred to as "recycling" the substrate. An oxidation reaction that includes a three-fold reagent addition procedure is referred to as an oxidation "cycle". Recycling the substrate may be performed one or more times.

In another example of an oxidation method, the reacting includes combining the substrate, the solvent and optionally an additive to form a substrate mixture, and then gradually adding both an iron catalyst mixture and an oxidant mixture to the substrate mixture, to form the reaction mixture. The composition mixture can include the iron catalyst, the solvent, and optionally an additive. The oxidant mixture can include the oxidant and the solvent. The gradual addition of both an iron catalyst mixture and an oxidant mixture is referred to as a "continuous reagent addition procedure".

In this example, the reaction time may be the time required for the composition mixture and the oxidant mixture to be combined in the reaction mixture. Preferably the reaction time is from 1.5 minutes to 6 hours, including from 9 minutes to 5 hours, from 15 minutes to 2 hours, and from 30 minutes to 1 hour. The time elapsed between forming the first mixture and beginning the continuous additions may be from 1 second to 10 minutes.

In an example of an oxidation method that includes a continuous reagent addition procedure, a substrate mixture contains a substrate, a solvent and an additive. The substrate can be present at a concentration of from 0.1 to 2 M, and the additive can be present at a level of from 0.01 to 1 equivalent relative to the substrate. A composition mixture can contain the complex of Formula (I), the solvent, and the additive. The complex can be present at a level of about 0.1 to 30 mol % relative to the substrate (0.01 to 1.0 M), and the additive, when present, can be present at a level of from 0.1 to 1 equivalent relative to the substrate. An oxidant mixture can include an oxidant and the solvent, where the oxidant is present at a level of from 1 to 4 equivalents relative to the substrate (0.01 to 1.0 M). The composition mixture and the oxidant mixture can be in separate syringes, each of which is loaded into a separate syringe pump. The composition mixture can be gradually added to the substrate mixture, to form the reaction mixture, at a rate of from 0.01 to 0.1 mL/min. Once from 1 to 10 drops of the composition mixture has been added, the oxidant mixture can be gradually added to the reaction mixture, for example, at a rate of from 0.1 to 0.5 mL/min. The volumes, concentrations, and addition rates of the composition and oxidant mixtures may be set so that the addition of the oxidant mixture is completed from 0 to 10 minutes after the addition of the composition mixture is completed.

Providing an oxidized product can include providing an oxidized product that includes a single oxidized functionality that was not present in the substrate. An oxidized product that includes a single oxidized functionality that was not present in the substrate is referred to as a "mono-oxidized product". Preferably providing an oxidized product includes providing mono-oxidized product (with respect to the oxidation caused by the iron catalyst) with a yield of at least 20%, at least 30%, at least 40%, or at least 50%. More preferably, providing an oxidized product includes providing mono-oxidized product with a yield of at least 60%, more preferably of at least 70%, more preferably of at least 80%, and more preferably of at least 90%. These yields may be the yields after an oxidation involving a three-fold reagent addition procedure or a continuous reagent addition procedure.

An oxidation reaction also may yield one or more oxidized products that include two or more oxidized functionalities that were not present in the substrate. Preferably, only minimal amounts of these multi-oxidized products are formed. Preferably less than 30% of the substrate is converted into a multi-oxidized product. More preferably, less than 20% of the substrate is converted into a multi-oxidized product, more preferably less than 10%, more preferably less than 5%, and more preferably less than 1%. Preferably a substrate molecule is either converted into the mono-oxidized product or is unoxidized.

The selectivity of oxidation of a substrate with a composition for selective $sp^3$ C—H bond oxidation can be affected by three separate factors. One possible selectivity factor is the electronic environment of the $sp^3$ C—H bonds of the substrate. A second possible selectivity factor is the steric environment of the $sp^3$ C—H bonds of the substrate. A third possible selectivity factor is the presence or absence of directing groups in the substrate. One advantage of oxidation with a composition for selective $sp^3$ C—H bond oxidation is that high selectivities can be obtained without directing groups in the substrate. However, the ability to utilize directing groups may provide selectivities that are different or better than those provided by the electronic and/or steric environments alone. Each of these selectivity factors may be used as a handle for predicting the selectivity of a catalytic oxidation of a substrate.

A composition described herein for selective $sp^3$ C—H bond oxidation may be used as a model of enzyme activity, such as the cytochrome P450 enzyme, to study, predict, model, and/or design the biological metabolism of a substance. Cytochrome P-450 enzymes can be used to perform metabolic profiling of bioactive agents such as pharmaceuticals, additives to food and consumer products, and pollutants (Schmidt, B. et al. *Biochem. Soc. Trans.* 34(6), pp. 1241-1245 (2006)). Metabolic profiling typically includes contacting a substance with at least one cytochrome P-450 enzyme, and analyzing the reaction product(s). A reaction product may be analyzed, for example, for toxicity.

Cytochrome P-450 enzymes also have been used in the design of pro-drug molecules, which are molecules that are converted into an active pharmaceutical upon metabolization. Pro-drug design typically includes contacting a pro-drug candidate with at least one cytochrome P-450 enzyme, and analyzing the reaction product(s). A reaction product may be analyzed, for example, for therapeutic efficacy.

A method of modeling the interaction of a cytochrome P-450 enzyme with a substrate includes reacting a substrate and an oxidant in a reaction mixture that includes an iron catalyst, to provide at least one oxidized product, and analyzing the at least one oxidized product. The reaction mixture may include a solvent and/or at least one additive. The composition may be a composition for selective $sp^3$ C—H bond oxidation, such as an iron catalyst complex described herein. The oxidized product may include an oxidized functionality that was not present in the substrate. Preferably the oxidized product is a mono-oxidized product. The substrate may be, for example, a bioactive agent, a pro-drug, or a pollutant. Analyzing the at least one oxidized product may include, for example, determining the toxicity of the product or determining the therapeutic efficacy of the product.

Modeling the interaction of a cytochrome P-450 enzyme using a composition for selective $sp^3$ C—H bond oxidation may provide a number of advantages. Cytochrome P-450 enzyme studies typically require whole biological cells and enzyme cofactors. In contrast, oxidation with a selective composition can be performed with standard solvents and reagents. An individual cytochrome P-450 enzyme typically oxidizes only a narrow range of substrates. In contrast, a selective composition can predictably oxidize a broad range of substrates. Cytochrome P-450 enzyme studies typically require large reaction volumes, long reaction times on the order of days, and/or product yields below 50%. In contrast, oxidation with a selective composition can be performed in milliliter volumes, within 20 to 45 minutes, and with product yields often of 50% or more.

Unactivated $sp^3$ C—H bonds can be predictably oxidized by a small molecule metal complex without the benefit of elaborate catalyst binding pockets or substrate directing groups. A single complex can be used across a wide range of complex small molecules to provide selective C—H oxidation, which may be based solely on the electronic and steric properties of the substrate. This general C—H oxidation reaction can fundamentally alter the ways in which intricate molecules and drugs are synthesized in the laboratory.

Figure 8A:
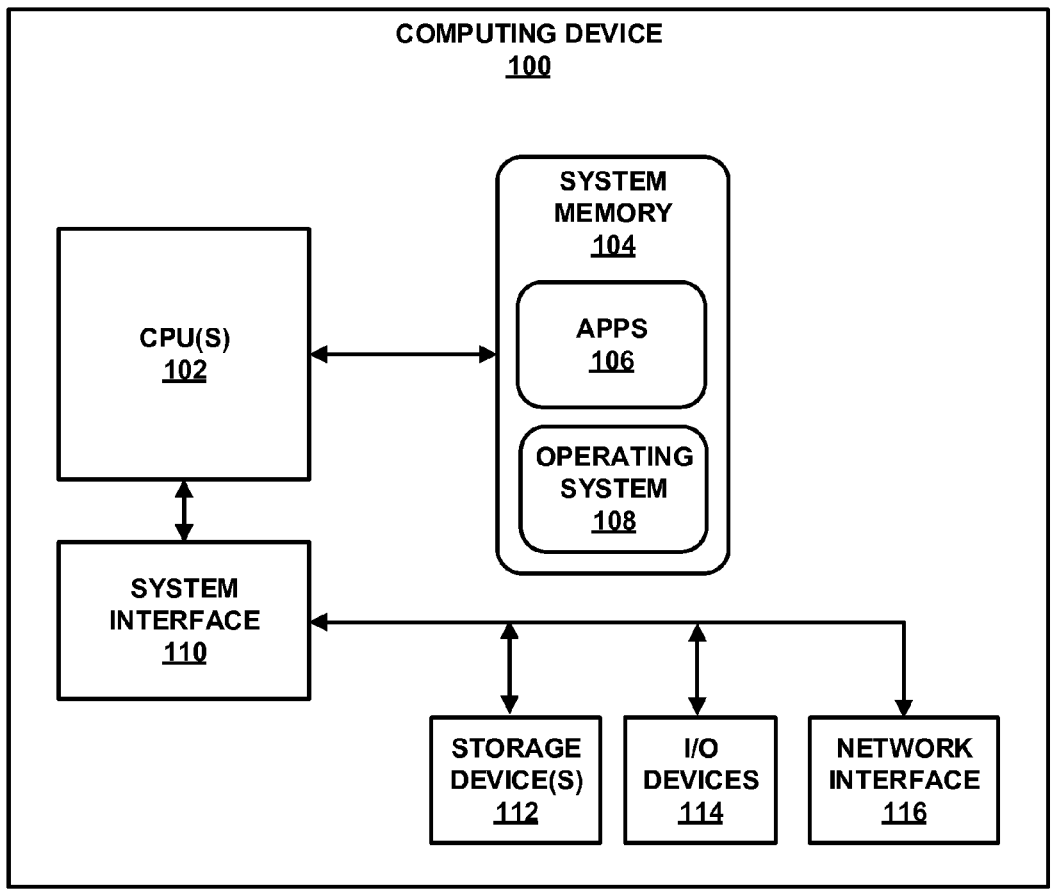
FIG. 8. A. A block diagram illustrating an example of a computing device that may implement one or more techniques of this disclosure. B. Normalized values prepared using an excel spreadsheet that contains all E and S values corresponding to each reactive site, as described in Expl. 3.

FIG. 8A is a block diagram illustrating an example of a computing device that may implement one or more techniques of this disclosure. Computing device 100 may include one or more processors and a plurality of internal and/or external storage devices. Examples of storage devices include file servers, FTP servers, network attached storage (NAS) devices, a local disk drive, removable memory devices, such as, for example, memory cards and USB memory devices, or any other type of device or storage medium capable of storing data. Storage medium may include Blu-ray discs, DVDs, CD-ROMs, flash memory, or any other suitable digital storage media. When the techniques described herein are implemented partially in software, a device may store instructions for the software in a suitable, non-transitory computer-readable medium and execute the instructions in hardware using one or more processors.

Computing device 100 is an example a computing device configured to model oxidation reactivity. Computing device 100 may be equipped for wired and/or wireless communications and may include devices, such as, for example, desktop or laptop computers, mobile devices, smartphones, cellular telephones, personal data assistants (PDA), tablet devices, set top boxes, personal gaming devices, and automotive infotainment systems. As illustrated in FIG. 8A, computing device 100 includes central processor unit(s)

102, system memory 104, system interface 110, storage device(s) 112, I/O device(s) 114, and network interface 116. As illustrated in FIG. 8A, system memory 104 includes applications 106 and operating system 108. It should be noted that although example computing device 100 is illustrated as having distinct functional blocks, such an illustration is for descriptive purposes and does not limit computing device 100 to a particular hardware or software architecture. Functions of computing device 100 may be realized using any combination of hardware, firmware and/or software implementations.

Central processing unit(s) 102 may be configured to implement functionality and/or process instructions for execution in computing device 100. Central processing unit (s) 102 may be capable of retrieving and processing instructions, code, and/or data structures for implementing one or more of the techniques described herein. Instructions may be stored on a computer readable medium, such as system memory 104 or storage devices 112. Central processing unit(s) 102 may include digital signal processors (DSPs), general purpose microprocessors, application specific integrated circuits (ASICs), field programmable logic arrays (FPGAs), or other equivalent integrated or discrete logic circuitry. Central processing unit(s) 102 may include one or more multi-core central processing units.

System memory 104 may be configured to store information that may be used by computing device 100 during operation. System memory 104 may be described as a non-transitory or tangible computer-readable storage medium. In some examples, system memory 104 may provide temporary memory and/or long-term storage. In some examples, system memory 104 or portions thereof may be described as non-volatile memory and in other examples portions of system memory may be described as volatile memory. Examples of volatile memories include random access memories (RAM), dynamic random access memories (DRAM), and static random access memories (SRAM). Examples of non-volatile memories include magnetic hard discs, optical discs, floppy discs, flash memories, or forms of electrically programmable memories (EPROM) or electrically erasable and programmable (EEPROM) memories. In one example, system memory may include an internal hard disk drive and/or an internal flash memory.

System interface 110 may be configured to enable communication between components of computing device 100. In one example, system interface 110 comprises structures that enable data to be transferred from one peer device to another peer device or to a storage medium. For example, system interface 110 may include a chipset supporting PCI bus, PCIe bus protocols, proprietary bus protocols, or any other form of structure that may be used to interconnect peer devices.

Storage device(s) 112 represents memory of computing device 100 that may be configured to store different amounts of information for different periods of time than system memory 104. Similar to system memory 104, storage device(s) 112 may also include one or more non-transitory or tangible computer-readable storage media. Storage device(s) 112 may be internal or external memory and in some examples may include non-volatile storage elements. Storage device(s) may include memory cards, external hard disk drives, and/or an external solid state drive.

I/O device(s) 114 may be configured to receive input and provide output for computing device 100. Input may be generated from an input device, such as, for example, touch-sensitive screen, track pad, track point, mouse, a keyboard, a microphone, video camera, or any other type of device configured to receive input. Output may be provided to output devices, such as, for example speakers or a display device. In some examples, I/O device(s) 114 may be external to computing device 100 and may be operatively coupled to computing device 100 using a standardized communication protocol, such as for example, Universal Serial Bus protocol (USB).

Network interface 116 may be configured to enable computing device 100 to communicate with external computing devices via one or more networks. Network interface 116 may be a network interface card, such as an Ethernet card, an optical transceiver, a radio frequency transceiver, or any other type of device that can send and receive information. Network interface 116 may be configured to operate according to one or more communication protocols such as, for example, a Global System Mobile Communications (GSM) standard, a code division multiple access (CDMA) standard, a 3rd Generation Partnership Project (3GPP) standard, an Internet Protocol (IP) standard, a Wireless Application Protocol (WAP) standard, and/or an IEEE standard, such as, one or more of the 802.11 standards, as well as various combinations thereof.

As illustrated in FIG. 8A, system memory 104 includes applications 106 and operating system 108. Applications 106 may be any applications implemented within or executed by computing device 100 and may be implemented or contained within, operable by, executed by, and/or be operatively/communicatively coupled to components of computing device 100. Applications 108 may include instructions that may cause central processing unit(s) 102 of computing device 100 to perform particular functions. Applications 106 may cause central processing unit(s) 102 to write data to or read data from a computer readable medium, such as for example, system memory 104 and/or storage device(s) 118. Applications 106 may include algorithms which are expressed in computer programming statements, such as, for loops, while-loops, if-statements, do-loops, etc. Applications 106 may be implemented using one or more programming languages. Examples of programming languages include Hypertext Markup Language (HTML), Dynamic HTML, Extensible Markup Language (XML), Extensible Stylesheet Language (XSL), Document Style Semantics and Specification Language (DSSSL), Cascading Style Sheets (CSS), Synchronized Multimedia Integration Language (SMIL), Wireless Markup Language (WML), Java™, Jini™, C, C++, Perl, Python, UNIX Shell, Visual Basic or Visual Basic Script, Virtual Reality Markup Language (VRML), ColdFusion™ and other compilers, assemblers, and interpreters.

As further illustrated in FIG. 8A, applications 106 may execute on top of operating systems 108. Operating systems 108 may be configured to facilitate the interaction of applications with central processing unit(s) 102, and other hardware components of computing device 100. Operating system 108 may be an operating system designed to be installed on laptops and desktops. For example, operating system 108 may be a Windows® operating system, Linux, or Mac OS. Operating system 108 may be an operating system designed to be installed on laptops, desktops, smartphones, and/or tablets computing devices. For example, operating system 108 may be a Windows®, Linux, Mac OS, Android, iOS, Windows Mobile®, or a Windows Phone® operating system. The techniques described herein are not limited to a particular operating system.

In one or more examples, the functions described may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. In addition, in some aspects, the functionality described herein may be provided within dedicated hardware and/or software modules. Also, the techniques could be fully implemented in one or more circuits or logic elements.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a codec hardware unit or provided by a collection of interoperative hardware units, including one or more processors as described above, in conjunction with suitable software and/or firmware.

Accordingly, the invention provides a method of modeling site-selectivity of oxidation in a molecule having aliphatic 3° (tertiary) and/or 2° (secondary) C—H bonds, the method comprising a) calculating an electronic difference value based on an electronic parameter associated with a first site of a molecule and an electronic parameter associated with a second site of a molecule; b) calculating a steric or stereoelectronic difference value based on a steric or stereoelectronic parameter associated with the first site and a steric or stereoelectronic parameter associated with the second site; and c) calculating a predictive $\Delta\Delta G^{\ddagger}$ value based on the calculated electronic difference value and the calculated steric or stereoelectronic difference value. An electronic parameter can be based on natural partial atomic charges of the molecule. A steric or stereoelectronic parameter can be based on a Winstein-Holness value. Calculating a predictive $\Delta\Delta G^{\ddagger}$ value using the calculated electronic difference value and the calculated steric difference value can include calculating the predictive $\Delta\Delta G^{\ddagger}$ based on observed $\Delta\Delta G^{\ddagger}$ data obtained from experimentally measured site-selectivity. Calculating the predictive $\Delta\Delta G^{\ddagger}$ based on observed $\Delta\Delta G^{\ddagger}$ data obtained from experimentally measured site-selectivity can include fitting observed $\Delta\Delta G^{\ddagger}$ to a curve and calculating the predictive $\Delta\Delta G^{\ddagger}$ based on a function associated with the curve.

The invention further provides a device for modeling site-selectivity of oxidation in a molecule having aliphatic 3° (tertiary) and/or 2° (secondary) C—H bonds, wherein the device comprises one or more processors configured to a) calculate an electronic difference value based on an electronic parameter associated with a first site of a molecule and an electronic parameter associated with a second site of a molecule; b) calculate a steric/stereoelectronic difference value based on a steric/stereoelectronic parameter associated with the first site and a steric/stereoelectronic parameter associated with the second site; and c) calculate a predictive $\Delta\Delta G^{\ddagger}$ value based on the calculated electronic difference value and the calculated steric/stereoelectronic difference value. An electronic parameter can be based on natural partial atomic charges of the molecule. A steric/stereoelectronic parameter can be based on a Winstein-Holness value. Calculating a predictive $\Delta\Delta G^{\ddagger}$ value using the calculated electronic difference value and the calculated steric difference value can include calculating the predictive $\Delta\Delta G^{\ddagger}$ based on observed $\Delta\Delta G^{\ddagger}$ data obtained from experimentally measured site-selectivity. Calculating the predictive $\Delta\Delta G^{\ddagger}$ based on observed $\Delta\Delta G^{\ddagger}$ date obtained from experimentally measured site-selectivity can also include fitting observed $\Delta\Delta G^{\ddagger}$ to a curve and calculating the predictive $\Delta\Delta G^{\ddagger}$ based on a function associated with the curve.

The invention further provides a non-transitory computer-readable storage medium comprising instructions stored thereon that upon execution cause one or more processors of a device to a) calculate an electronic difference value based on an electronic parameter associated with a first site of a molecule and an electronic parameter associated with a second site of a molecule; b) calculate a steric/stereoelectronic difference value based on a steric/stereoelectronic parameter associated with the first site and a steric/stereoelectronic parameter associated with the second site; and c) calculate a predictive $\Delta\Delta G^{\ddagger}$ value based on the calculated electronic difference value and the calculated steric/stereoelectronic difference value. An electronic parameter can be based on natural partial atomic charges of the molecule. A steric/stereoelectronic parameter can be based on a Winstein-Holness value. Calculating a predictive $\Delta\Delta G^{\ddagger}$ value using the calculated electronic difference value and the calculated steric difference value can include calculating the predictive $\Delta\Delta G^\ddagger$ based on observed $\Delta\Delta G^\ddagger$ data obtained from experimentally measured site-selectivity. Calculating the predictive $\Delta\Delta G^\ddagger$ based on observed $\Delta\Delta G^\ddagger$ date obtained from experimentally measured site-selectivity can also include fitting observed $\Delta\Delta G^\ddagger$ to a curve and calculating the predictive $\Delta\Delta G^\ddagger$ based on a function associated with the curve. As used herein, reference to a steric/stereoelectronic parameter includes a steric parameter, a stereoelectronic parameter, or a combination thereof.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14th Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrase "one or more" is readily understood by one of skill in the art, particularly when read in context of its usage. For example, one or more substituents on a phenyl ring refers to one to five, or one to four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment. The term about can also modify the end-points of a recited range as discuss above in this paragraph.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to bring about a recited effect, such as an amount necessary to form products in a reaction mixture. Determination of an effective amount is typically within the capacity of persons skilled in the art, especially in light of the detailed disclosure provided herein. The term "effective amount" is intended to include an amount of a compound or reagent described herein, or an amount of a combination of compounds or reagents described herein, e.g., that is effective to form products in a reaction mixture. Thus, an "effective amount" generally means an amount that provides the desired effect.

The term "complex" means a molecular entity including a central metal atom, to which is associated a surrounding array of other groups of atoms, referred to as "ligands."

The term "group" means a linked collection of atoms or a single atom within a molecular entity, where a molecular entity is any constitutionally or isotopically distinct atom, molecule, ion, ion pair, radical, radical ion, complex, conformer, etc., identifiable as a separately distinguishable entity. The description of a group as being "formed by" a particular chemical transformation does not imply that this chemical transformation is involved in making the molecular entity that includes the group.

The term "alkyl group" means a group formed by removing a hydrogen from a carbon of an alkane, where an alkane is an acyclic or cyclic compound consisting entirely of hydrogen atoms and saturated carbon atoms. An alkyl group may also be substituted with one or more substituent groups. Of course, when an alkyl group or a group described below is disubstituted, two hydrogen atoms are removed from an atom or two separate atoms of the group.

The term "heteroalkyl group" means a group formed by removing a hydrogen from a carbon of a heteroalkane, where a heteroalkane is an acyclic or cyclic compound consisting entirely of hydrogen atoms, saturated carbon atoms, and one or more heteroatoms. A heteroalkyl group may be substituted with one or more substituent groups.

The term "aryl group" means a group formed by removing a hydrogen from a ring carbon atom of an aromatic compound. An aryl group may be monocyclic or polycyclic and may include one or more heteroatoms in the ring and/or may be substituted with one or more substituent groups.

The term "aromatic compound" means a monocyclic or polycyclic aromatic hydrocarbon, optionally including one or more heteroatoms in the ring. An aromatic compound may be substituted with one or more substituent groups.

The term "heteroaryl group" means an aryl group that contains a heteroatom in the ring. A heteroaryl group may be monocyclic or polycyclic and may be substituted with one or more substituent groups.

The term "heterocyclic group" means a group formed by removing a hydrogen from a ring atom of a heterocyclic compound, where a heterocyclic compound is a cyclic compound having as ring members carbon and at least one other element. Heterocyclic groups include heterocycloalkyl groups, heteroaryl groups, and mixtures of these. A heterocyclic group may be monocyclic or polycyclic and may be substituted with one or more substituent groups.

The term "pyridyl group" means a group formed by removing a hydrogen from a ring atom of pyridine. A pyridyl group may be substituted with one or more substituent groups. Substituent groups of a pyridyl group may form a ring, in which case the pyridyl group is part of a polycylic heterocyclic group, such as a quinolinyl group.

The term "substituent group" means a group that replaces one or more hydrogen atoms in a molecular entity. Examples of substituent groups include halide groups, alkyl groups, heteroalkyl groups, aryl groups, heteroaryl groups, and nitro groups.

The term "halide group" or "halo" refers to —F, —Cl, —Br or —I.

The terms "oxidation" or "oxidize" refers to a chemical transformation of a substrate molecule, where the oxidized product molecule of the chemical transformation includes at least one more oxygen atom and/or at least one fewer hydrogen atom than the original substrate molecule. Oxidation of an $sp^3$-hybridized C—H bond can result in the formation of, for example, a hydroxyl group or a carbonyl group.

The term "oxidant" means a substance that provides at least one oxygen atom to, and/or accepts at least one hydrogen atom from, a substrate molecule in an oxidation reaction of the substrate.

The term "$sp^3$ C—H bond" means a C—H bond in which the carbon atom is bonded to three other atoms through individual single bonds. A 2° C—H bond is one where the carbon is attached to two other carbon atoms; a 3° C—H bond is one where the carbon is attached to three other carbon atoms The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

General Information: All C—H oxidations were run under air with no precautions taken to exclude moisture. All other reactions were run under an Ar or $N_2$ atmosphere with dry solvent in flame dried glassware unless otherwise noted. Dry solvents tetrahydrofuran (THF), methylene chloride ($CH_2Cl_2$), diethyl ether ($Et_2O$), dimethylformamide (DMF), acetonitrile (MeCN), toluene (PhMe) and benzene (PhH) were purified prior to use by passage through a bed of activated alumina (Glass Contour, Laguna Beach, Calif.). Triethylamine and pyridine were distilled from calcium hydride. Commercially available reagents that were used as received are noted in the individual reaction procedures. (S,S)— and (R,R)-2,2'-Bispyrrolidine tartrate were prepared according to the literature procedure (Denmark et al., *Org. Synth.* 2006, 83, 121). The ee of the diamine was checked by conversion to the dibenzoate and analysis by reverse phase HPLC; obtained either enantiomer in >99% ee (Chiralpak AD-RH, 35:60:5 MeCN:$H_2O$:i-PrOH, 0.3 mL/min., 30° C., $t_R$(S,S)=34.85 min, $t_R$(R,R)=41.68 min) (S,S)— and (R,R)—F e(PDP) (1) were prepared according to literature procedures (Chen and White, *Science* 2007, 318, 783). (−)-Triacetoxy tricalysiolide B (19) was prepared according to the literature procedure from coffee oil (Bigi et al., *Synlett* 2012, 23, 2768).

Solvents were removed by rotary evaporation at ~30° C. and ~40 torr unless otherwise noted. Thin-layer chromatography (TLC) was performed with E. Merck silica gel 60 F254 precoated plates (0.25 mm) and visualized with UV and/or potassium permanganate or ceric ammonium molybdate staining. Flash chromatography was performed as described by Still et al. (*J. Org. Chem.* 1978, 43, 2923) using EM reagent silica gel 60 (230-400 mesh). $CDCl_3$ was stored over 4 Å molecular sieves.

$^1$H lNMR spectra were recorded on a Varian Inova 500NB (500 MHz), Varian Untiy 500 (500 MHz) or Varian VXR 500 (500 MHz) spectrometer and are reported in ppm using solvent ($CDCl_3$ at 7.26 ppm) as an internal standard unless otherwise noted. Data reported as: s=singlet, d=doublet, t=triplet, q=quartet, p=pentet, m=multiplet, b=broad, app=apparent; coupling constant(s) in Hz; integration. Proton-decoupled $^{13}$C NMR spectra were recorded on Varian Untiy 500 (125 MHz) or Varian VXR 500 (125 MHz) and are reported in ppm using solvent ($CDCl_3$, 77.0 ppm) as an internal standard unless otherwise noted. $^{19}$F spectra were recorded on Varian Untiy 500 (470 MHz) or Varian VXR 500 (470 MHz) and are reported in ppm using $FCCl_3$ (0 ppm) as an external standard. IR spectra were recorded as thin films on NaCl plates on a Mattson Galaxy Series FTIR 5000 and are reported in frequency of absorption (cm$^{-1}$). High-resolution mass spectra were obtained at the University of Illinois Mass Spectrometry Laboratory. Achiral gas chromatographic (GC) analyses were performed on an Agilent Technologies 6890N Series instrument equipped with FID detectors using a HP-5 (5%-phenyl)-methylpolysiloxane column (30 m, 0.32 mm, 0.25 mm) Optical rotations were measured in a 1 mL cell with 50 mm path length or a 0.2 mL cell with a 10 mm path length on a Jasco P-1020 polarimeter. Optical rotations were obtained with a sodium lamp and are reported as follows: $[\alpha]_\lambda^{T° \, C}$. (c=g/100 mL, solvent). Medium pressure liquid chromatography (MPLC) separations were performed on a Teledyne Isco CombiFlashRf system using 12 or 24 g Redi Sep Rf Gold silica columns.

Example 1

Synthesis and Characterization of C—H Oxidation Catalyst Fe(CF$_3$-PDP) (3)

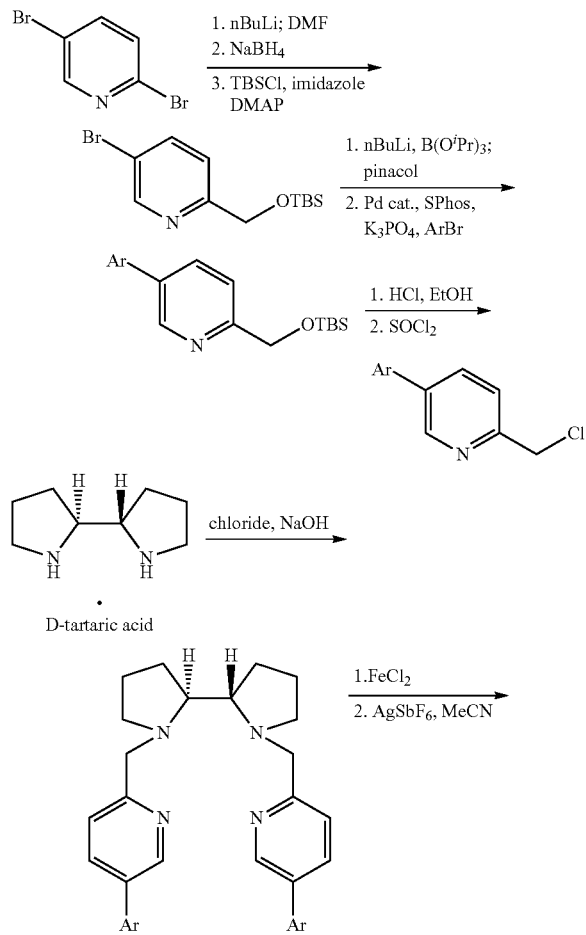

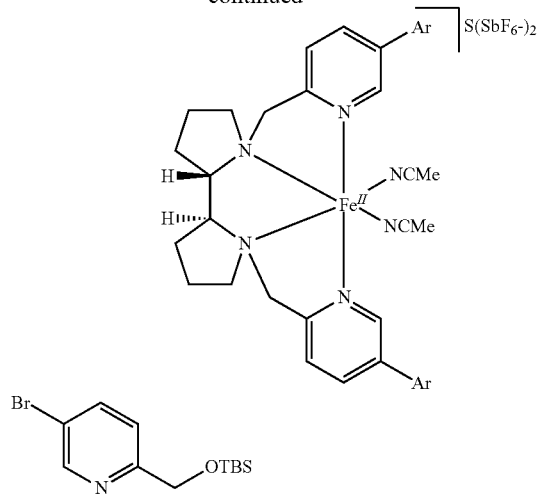

5-Bromo-2-(((tert-butyldimethylsilyl)oxy)methyl)pyridine. 2,5-Dibromopyridine (50.0 g, 211 mmol, 1.0 equiv, Oakwood Products) was suspended in PhMe (0.2 M) in a 2 L round bottomed flask. The suspension was cooled to −78° C. and n-BuLi (160 mL, 253 mmol, 1.2 equiv, 1.6 M in hexanes, Sigma-Aldrich) was added dropwise over 10 min. The reaction was stirred for 2 h at −78° C., at which time DMF (33 mL, 30.8 g, 422 mmol, 2.0 equiv) was added dropwise and stirring continued an additional 1 h. The dark solution was warmed to 0° C. and MeOH (211 mL) followed by NaBH$_4$ (8.0 g, 211 mmol, 1.0 equiv, Sigma-Aldrich) were added carefully. Stirring was continued for 1 h allowing the reaction to warm to room temperature. The reaction was quenched with H$_2$O (~100 mL). The resulting layers were separated and the aqueous layer was extracted with CH$_2$Cl$_2$ (3×100 mL). The combined organic layers were dried (Na$_2$SO$_4$), filtered and concentrated to give a crude oil. The crude was dissolved in CH$_2$Cl$_2$ (340 mL) in a 1 L round bottomed flask. TBSCl (30.8 g, 204 mmol, 1.2 equiv, TCI), imidazole (17.4 g, 255 mmol, 1.5 equiv, Sigma-Aldrich) and DMAP (2.1 g, 17 mmol, 0.1 equiv, Sigma-Aldrich) were added in one portion and the reaction was stirred for 12 h at room temperature. The reaction was quenched with H$_2$O (100 mL) and the resulting layers were separated. The aqueous layer was extracted with CH$_2$Cl$_2$ (3×50 mL) and the combined organic layers were dried (Na$_2$SO$_4$), filtered and concentrated. Purification by flash chromatography on silica (~600 mL) eluting with 10% EtOAc/hexanes afforded the title compound (50.8 g, 168 mmol, 80% yield) as a light yellow oil. $^1$H NMR (500 MHz, CDCl$_3$) δ 8.54 (d, J=2.4 Hz, 1H), 7.80 (dd, J=8.4, 2.3 Hz, 1H), 7.40 (dd, J=8.3, 1.0 Hz, 1H), 4.76 (s, 2H), 0.93 (s, 9H), 0.10 (s, 6H); $^{13}$C NMR (125 MHz, CDCl$_3$) δ 160.0, 149.6, 139.1, 121.4, 118.4, 65.5, 25.8, 18.3, −5.4; IR (film): 2954, 2929, 2887, 2858, 1577, 1560, 1470, 1377, 1362, 1257, 1103, 1007, 939, 841, 779 cm$^{-1}$; HRMS (ESI) m/z calc'd for C$_{12}$H$_{21}$NOSiBr [M+H]$^+$: 302.0576, found 302.0566.

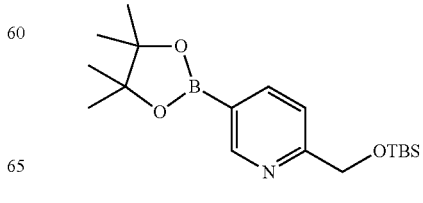

2-(((tert-Butyldimethylsilyl)oxy)methyl)-5-(4,4,5,5-tetramethyl-1,3,2-dioxaborolan-2-yl)pyridine. 5-Bromo-2-(((tert-butyldimethylsilyl)oxy)methyl)pyridine (20.6 g, 68 mmol, 1.0 equiv) and triisopropyl borate (18.9 mL, 15.4 g, 81.6 mmol, Sigma-Aldrich) were dissolved in THF (136 mL) in a 500 mL round bottomed flask. The solution was cooled to −78° C. and nBuLi (51 mL, 81.6 mmol, 1.2 equiv, 1.6 M in hexanes) was added over 1 h via syringe pump. After the addition was complete, the reaction was stirred for an additional 2 h at −78° C., at which time it was allowed to warm to 0° C. The reaction was carefully quenched to pH=6 with 1 M $KH_2PO_4$. The layers were separated and the aqueous layer was extracted with $CH_2Cl_2$ (3×30 mL). The combined organic layers were dried ($Na_2SO_4$), filtered and concentrated to give a crude oil. The oil was dissolved in PhH (136 mL) in a 250 mL round bottomed flask, to which pinacol (9.6 g, 81.6 mmol, 1.2 equiv, Oakwood Products) was added. The flask was fitted with a dean-stark trap and the reaction was refluxed overnight. After cooling to room temperature, water (50 mL) was added and the layers were separated. The aqueous layer was extracted with EtOAc (3×30 mL) and the combined organic layers were dried ($Na_2SO_4$), filtered and concentrated. Purification by flash chromatography on silica (~600 mL) eluting with 20→30% EtOAc/hexanes afforded the title compound (15.1 g, 44.4 mmol, 65% yield) as a light yellow oil. $^1$H NMR (500 MHz, $CDCl_3$) δ 8.83 (s, 1H), 8.07 (d, J=5.0 Hz, 1H), 7.50 (d, J=10.0 Hz, 1H), 4.85 (s, 2H), 1.35 (s, 12H), 0.95 (s, 9H), 0.11 (s, 6H); $^{13}$C NMR (125 MHz, $CDCl_3$) δ 164.0, 154.5, 142.9, 119.1, 84.0, 66.2, 25.9, 24.8, 18.3, −5.4; IR (film): 2980, 2954, 2931, 2889, 2858, 1600, 1560, 1471, 1363, 1311, 1257, 1215, 1146, 1103, 1024, 1007, 962, 843, 777, 735, 667 cm$^{-1}$; HRMS (ESI) m/z calc'd for $C_{18}H_{33}NO_3BSi$ [M+H]$^+$: 350.2323, found 350.2320.

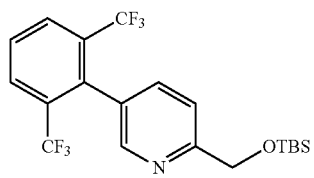 [SMILES: CC(C)(C)[Si](C)(C)OCc1ccc(-c2c(C(F)(F)F)cccc2C(F)(F)F)cn1]

5-(2,6-Bis(trifluoromethyl)phenyl)-2-(((tert-butyldimethylsilyl)oxy)methyl)pyridine. A 50 mL round bottomed flask fitted with a rubber septum was charged with a stir bar, Pd(OAc)$_2$ (74.8 mg, 0.33 mmol, 3 mol %, Johnson Matthey), SPhos (275.1 mg, 0.67 mmol, 6 mol %, Strem), 2-bromo-1,3-bis(trifluoromethyl)benzene (3.25 g, 11.1 mmol, 1.0 equiv, Synquest Laboratories) and $K_3PO_4$ (4.71 g, 22.2 mmol, 2.0 equiv, Strem). The flask was evacuated and backfilled with N$_2$ (×3). Toluene (20 mL) and degassed DI H$_2$O (2 mL) were added followed by 2-(((tert-butyldimethylsilyl)oxy)methyl)-5-(4,4,5,5-tetramethyl-1,3,2-dioxaborolan-2-yl)pyridine (5.82 g, 16.6 mmol, 1.5 equiv). The rubber septum was quickly replaced with a yellow polyethylene cap and secured with electrical tape. The reaction was heated at 100° C. in an oil bath for 16 h, at which time it was allowed to cool to room temperature and quenched with water (10 mL). The layers were separated and the aqueous layer was extracted with $CH_2Cl_2$ (3×10 mL). The combined organic layers were dried ($Na_2SO_4$), filtered and concentrated. Purification by flash chromatography on silica (~300 mL) eluting with 5% EtOAc/hexanes afforded the title compound in approximately 61% yield with some minor impurities resulting from protodeboronation of the pinacol borane. The product was taken on to subsequent synthetic steps during the course of which, the impurities were removed.

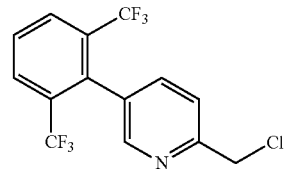 [SMILES: FC(F)(F)c1cccc(C(F)(F)F)c1-c1ccc(CCl)nc1]

5-(2,6-Bis(trifluoromethyl)phenyl)-2-(chloromethyl)pyridine. This reaction was preformed open to air. 5-(2,6-Bis(trifluoromethyl)phenyl)-2-(((tert-butyldimethylsilyl)oxy)methyl)pyridine (2.96 g, 6.8 mmol, 1.0 equiv) was dissolved in EtOH (7 mL) and 3N HCl (7 mL). The reaction was stirred vigorously for 3 h, quenched to neutral pH with saturated NaHCO$_3$, and diluted with $CH_2Cl_2$. The layers were separated and the aqueous layer was extracted with $CH_2Cl_2$ (×3). The combined organic layers were dried ($Na_2SO_4$), filtered and concentrated to give a crude solid. The solid was dissolved in $CH_2Cl_2$ (34 mL) and SOCl$_2$ (5 mL, 8.09 g, 68 mmol, 10.0 equiv, Sigma-Aldrich) was added dropwise. The reaction was stirred 12 h and quenched to neutral pH with saturated NaHCO$_3$. The layers were separated and the aqueous layer was extracted with $CH_2Cl_2$ (×3). The combined organic layers were dried ($Na_2SO_4$), filtered and concentrated. Purification by flash chromatography on silica (~250 mL) eluting with 5% EtOAc/hexanes afforded the title compound (1.08 g, 3.0 mmol, 76% yield) as a colorless powder. $^1$H NMR (500 MHz, $CDCl_3$) δ 8.46 (s, 1H), 8.00 (d, J=8.0 Hz, 2H), 7.70 (t, J=8.0 Hz, 1H), 7.64 (d, J=8.5 Hz, 1H), 7.56 (d, J=8.5 Hz, 1H), 4.76 (s, 2H); $^{13}$C NMR (125 MHz, $CDCl_3$) δ 156.6, 149.4, 138.3, 136.0, 131.7 (q, J=30.3 Hz), 129.4, 129.4 (q, 4.9 Hz), 128.9, 123.0 (q, 274.4 Hz), 120.9, 46.3; $^{19}$F NMR (470 MHz, $CDCl_3$) δ −57.9; IR (film): 1599, 1587, 1564, 1375, 1340, 1296, 1209, 1182, 1132, 1103, 1066, 1002, 822, 762, 677 cm$^{-1}$; HRMS (ESI) m/z calc'd for $C_{14}H_9NClF_6$ [M+H]$^+$: 340.0328, found 340.0318.

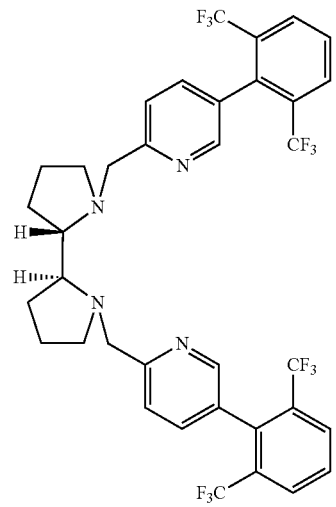 [SMILES: FC(F)(F)c1cccc(C(F)(F)F)c1-c1ccc(CN2CCC[C@H]2[C@@H]2CCCN2Cc2ccc(-c3c(C(F)(F)F)cccc3C(F)(F)F)cn2)nc1]

(2S,2'S)-1,1'-Bis((5-(2,6-bis(trifluoromethyl)phenyl)pyridin-2-yl)methyl)-2,2'-bipyrrolidine [(S,S)—Fe(CF$_3$-PDP)]. This reaction was performed open to air. According to the procedure of White (*Science* 2007, 318, 783), a round bottomed flask was charged with a stir bar, 5-(2,6-bis(trifluoromethyl)phenyl)-2-(chloromethyl)pyridine (1.87 g, 5.5 mmol, 2.2 equiv), (S,S)-2,2'-bispyrrolidine/D-tartaric acid (725.8 mg, 2.5 mmol, 1.0 equiv), NaOH (640 mg, 16 mmol, 6.4 equiv) and 1:1 $CH_2Cl_2:H_2O$ (10 mL) and the reaction was stirred vigorously at room temperature for 12 h. The reaction was diluted with 1M NaOH and $CH_2Cl_2$. The layers were separated and the aqueous layer was extracted with $CH_2Cl_2$ (×5). The combined organic layers were dried ($K_2CO_3$), filtered and concentrated. Purification by flash chromatography on silica (~125 mL) eluting with 5% MeOH/$CH_2Cl_2$ with 1% $NH_4OH$ afforded the crude ligand, which was partitioned between $CH_2Cl_2$ and 1 M NaOH. The layers were separated and the aqueous layer was extracted with $CH_2Cl_2$ (×5). This extraction removes traces of water and $NH_4OH$ from the column conditions. The combined organic layers were dried ($K_2CO_3$), filtered and concentrated to afford the title compound (1.19 g, 1.6 mmol, 64% yield) as a colorless powder. $^1H$ NMR (500 MHz, $CDCl_3$) δ 8.40 (s, 2H), 7.97 (d, J=7.5 Hz, 4H), 7.65 (t, J=8.0 Hz, 2H), 7.53 (d, J=7.5 Hz, 2H), 7.48 (d, J=8.5 Hz, 2H), 3.91 (ABq, J=14.5 Hz, Δv=274.5 Hz, 4H), 3.08-3.00 (m, 2H), 2.75 (app t, J=6.0 Hz, 2H), 2.29 (q, J=8.5 Hz, 2H), 1.86-1.66 (m, 8H); $^{13}C$ NMR (125 MHz, $CDCl_3$) δ 160.8 (2C), 148.8 (2C), 137.6 (2C), 136.9 (2C), 131.8 (q, J=29.5 Hz, 2C), 129.3 (q, J=5.5 Hz, 2C), 128.5 (2C), 128.0 (2C), 123.1 (q, J=275.3, 2C), 121.1 (2C), 65.5 (2C), 61.2 (2C), 55.6 (2C), 25.9 (2C), 23.6 (2C); $^{19}F$ NMR (470 MHz, $CDCl_3$) δ −57.8; IR (film): 3043, 2987, 2954, 2935, 2897, 2846, 1763, 1741, 1441, 1371, 1290, 1255, 1221, 1182, 1101, 1072, 952 $cm^{-1}$; HRMS (ESI) m/z calc'd for $C_{36}H_{31}N_4F_{12}$ [M+H]$^+$: 747.2357, found 747.2352; $[α]_D^{25}$=−14.4° (c=1.0, $CHCl_3$).

(R,R)—Fe($CF_3$-PDP) was also prepared. $[α]_D^{24}$=+16.2° (c=1.1, $CHCl_3$).

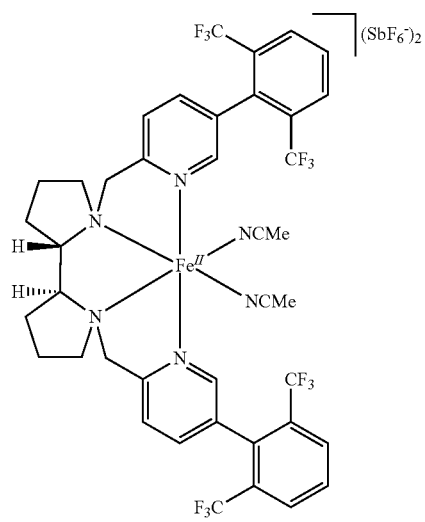

[(S,S)—Fe(Fe($CF_3$-PDP)(MeCN)$_2$](SbF$_6$)$_2$ (2). According to the procedure of White (*Science* 2007, 318, 783), a 50 mL round bottomed flask was charged with a stir bar, (S,S)—Fe($CF_3$-PDP) (1.19 g, 1.6 mmol, 1.0 equiv) and MeCN (9.4 mL). FeCl$_2$·4H$_2$O (318.1 mg, 1.6 mmol, 1.0 equiv, Strem) was added and the reaction was stirred 24 h at room temperature Immediately after adding the iron salt, an orange precipitate was observed. The precipitation was completed at the end of the reaction by addition of Et$_2$O. Solvent was decanted out of the flask via pipette. The resulting solid was washed thoroughly with Et$_2$O until the washes are colorless and dried under a stream of N$_2$ for 4 h to yield (S,S)—Fe($CF_3$-PDP)Cl$_2$ (1.26 g, 1.4 mmol, 90% yield) as a bright orange powder. HRMS (ESI) m/z calc'd for $C_{36}H_{30}ClF_{12}FeN_4$ [M−Cl]$^+$: 1037.0571, found 1037.0577.

A 50 mL round bottomed flask (the flask should be free of trace metal impurities and not have been cleaned with harsh acidic or basic conditions such as nitric acid or base bath) was charged with a stir bar, (S,S)—Fe($CF_3$-PDP)Cl$_2$ (1.27 g, 1.4 mmol, 1.0 equiv) and MeCN (17.5 mL). AgSbF$_6$ (962.3 mg, 2.8 mmol, 2.0 equiv, Strem, stored and weighed out in the glove box with precautions taken to exclude light, air and moisture) was added in 1 portion resulting in immediate precipitation of AgCl and a color change to dark red/purple. The reaction flask was wrapped in foil to exclude light and stirred vigorously for 24 h. The reaction was filtered through Celite® and concentrated nearly to dryness. The catalyst was redissolved in MeCN, filtered through a 0.2 μm Acrodisc® LC PVDF (HPLC certified) and concentrated nearly to dryness. The filtration procedure was repeated (×2) to ensure complete removal of silver salts. The resulting solid was dried under a stream of N$_2$ for 5 h to yield the title compound (1.81 g, 1.3 mmol, 96% yield) as a light red powder. HRMS (ESI) m/z calc'd for $C_{36}H_{30}N_4F_{18}FeSb$ [M—(MeCN)$_2$(SbF$_6$)]$^+$: 265.1804, found 265.1804. Anal. calc'd for $C_{40}H_{36}F_{24}FeN_6Sb_2$ (MW=1356.08 g/mol): C, 35.43; H, 2.68; N, 6.20; Fe 4.12; found: C, 35.16; H, 2.39; N, 6.52; Fe 4.20. $^1H$ NMR (500 MHz, CD$_3$CN) δ 32.34 (br s), 20.81 (br s), 18.67 (br s), 16.66 (br s), 13.36-12.87 (m), 12.14-11.29 (m), 8.36 (s), 7.47 (s), 6.22 (s).

X-ray quality crystals were obtained by dissolving 30 mg of the complex in a ½ dram vial with minimal MeCN and 1 drop PhH. This vial was loosely capped and put into a 20 mL scintillation vial filled with ~7 mL Et$_2$O. The larger vial was capped tightly. After ~3 days, dark red crystals formed after slow diffusion of the Et$_2$O into the smaller vial.

Example 2

Catalyst-Controlled Oxidation of Simple Linear and Cyclic Molecules

Method A: Iterative Addition Protocol. These reactions were performed open to air with no precautions taken to exclude moisture. A 40 mL vial was charged with substrate (0.5 mmol, 1.0 equiv), MeCN (0.75 mL, 0.66 M), AcOH (14.3 μL, 15.0 mg, 0.25 mmol, 0.5 equiv, Fisher Scientific), catalyst (0.025 mmol, 5 mol %) and a stir bar. A separate solution of H$_2$O$_2$ (34.6 μL, 0.6 mmol, 1.2 equiv, 50% wt. in H$_2$O, Sigma-Aldrich) in MeCN (4.5 mL, 0.13 M) was added dropwise to the stirring reaction over ~60 s. The first drop of peroxide solution instantly changes the reaction mixture from light red (when using Fe($CF_3$-PDP)) to a light amber. Subsequent drops of peroxide appear transiently as green in the reaction until a dark amber color is reached and maintained. When no further color changes were observed, the addition rate of the peroxide was increased to complete the addition in ~60 s. Significant decreases in yield were noted when the peroxide solution was added rapidly.

After 10 minutes, a solution of the catalyst (0.025 mmol, 5 mol %) and AcOH (14.3 μL, 15.0 mg, 0.25 mmol, 0.5 equiv) in MeCN (0.5 mL) was added to the stirring reaction, immediately followed by dropwise addition of a second solution of H$_2$O$_2$ (34.6 μL, 0.6 mmol, 1.2 equiv, 50% wt. in H$_2$O) in MeCN (4.5 mL, 0.13 M) as described above. After an additional 10 min., a third addition of catalyst and AcOH followed by dropwise $H_2O_2$ solution addition was repeated as above and allowed to stir 10 min., for a total reaction time of ~33 minutes. See Chen and White, *Science* 2007, 318, 783.

If a crude NMR was desired, the reaction was concentrated via rotary evaporation to a minimal volume, diluted with EtOAc and filtered through a plug of silica (~50 mL) to remove the residual paramagnetic iron catalyst. After rotary evaporation, analysis of the crude by $^1H$ NMR could be performed. Otherwise, the reaction was concentrated to a minimal volume and loaded directly onto silica gel and purified by flash chromatography. Generally, visualization was accomplished using CAM (ceric ammonium molybdate) staining.

Method B: Slow Addition Protocol. These reactions were performed open to air with no precautions take, to exclude moisture. A 20 mL scintillation vial was charged with substrate (0.3 mmol, 1.0 equiv), MeCN (0.6 mL, 0.5 M), AcOH (8.6 μL, 9.0 mg, 0.15 mmol, 0.5 equiv) and a stair bar. A 1.0 mL syringe was filled with a solution of the catalyst (0.075 mmol, 25 mol %) in MeCN (0.375 mL, 0.2 M). A few drops of this solution were added to the reaction. A 10 mL syringe was filled with a solution of $H_2O_2$ (86.5 μL, 1.5 mmol, 5.0 equiv, 50% wt. in $H_2O$) in MeCN (3.75 mL). Both syringes were fitted with 25 G needles and loaded into a syringe pump set at an addition rate of 4 mL/h resulting in a slow simultaneous addition of catalyst and oxidant over 1 h to the stirring reaction mixture (see Vermeulen et al., *Tetrahedron* 2009, 65, 3078). Workup as in general procedure A.

"Cycle" refers to the standard iterative or slow addition procedure as described above. "Recycle" refers to collecting starting material from the previous cycle and subjecting it to another oxidation cycle to obtain product. "RSM" is recovered starting material.

Certain data from specific reactions described below are also summarized in FIG. 2.

Reaction 1. Oxidation of (2S,4S)-Methyl 2,4-dimethylhexanoate

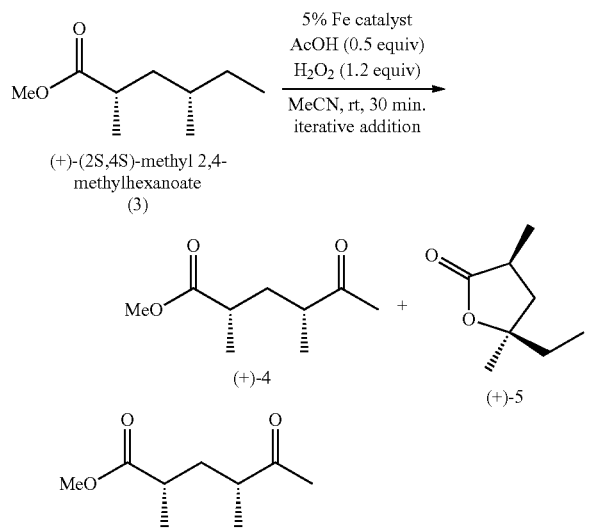

(+)-(2S,4R)-methyl 2,4-dimethyl-5-oxohexanoate (4). (+)-(2S,4S)-methyl 2,4-dimethylhexanoate (3) (158.2 mg, 1.0 mmol, 1.0 equiv) was reacted with (S,S)—Fe(CF$_3$-PDP) (2) according to Method A. Purification by flash chromatography on silica (~125 mL) eluting with 20% Et$_2$O/pet ether. Run 1: recycled one time for a total of 51% (+)-4, 12% (+)-5, 10% RSM, 4.0:1 crude 2°:3° by GC; cycle 1 (+)-4 (74.4 mg, 0.43 mmol, 43%), (+)-5 (14.4 mg, 0.1 mmol, 10%), RSM (44.5 mg, 0.28 mmol, 28%); cycle 2 (+)-4 (18.3 mg, 0.11 mmol, 38%), (+)-5 (4.1 mg, 0.029 mmol, 10%), RSM (11.3 mg, 0.071 mmol, 26%). Run 2: recycled one time for a total of 54% (+)-4, 13% (+)-5, 7% RSM, 4.0:1 crude 2°:3° by GC; cycle 1 (+)-4 (67.6 mg, 0.39 mmol, 39%), (+)-5 (13.0 mg, 0.091 mmol, 9%), RSM (47.5 mg, 0.3 mmol, 30%); cycle 2 (+)-4 (21.2 mg, 0.12 mmol, 41%), (+)-5 (4.7 mg, 0.03 mmol, 11%), RSM (16.1 mg, 0.1 mmol, 34%). Run 3: recycled one time for a total of 49% (+)-4, 9% (+)-5, 7% RSM, 3.9:1 crude 2°:3° by GC; cycle 1 (+)-4 (64.4 mg, 0.37 mmol, 37%), (+)-5 (7.4 mg, 0.05 mmol, 5%), RSM (49.4 mg, 0.31 mmol, 31%); cycle 2 (+)-4 (21.5 mg, 0.12 mmol, 40%), (+)-5 (5.5 mg, 0.039 mmol, 12%), RSM (11.3 mg, 0.071 mmol, 23%). Average overall yield (+)-4: 51±2%, Average overall yield (+)-5: 11±2%, Average overall RSM: 8±2%, Average 2°:3°: 4.0±0.1:1. $^1H$ NMR (500 MHz, CDCl$_3$) δ 3.70 (s, 3H), 2.60-2.48 (m, 2H), 2.17 (s, 3H), 2.12-2.06 (m, 1H), 1.40-1.34 (m, 1H), 1.19 (d, J=7.0 Hz, 3H), 1.12 (d, J=7.0 Hz, 3H); HRMS (ESI) m/z calc'd for C$_9$H$_{16}$O$_3$Na [M+Na]$^+$: 195.0997, found 195.1006; [α]$_D^{25}$=+11.0° (c=1.0, CHCl$_3$). These spectral data match those reported in the literature (Chen and White, *Science* 2007, 318, 783).

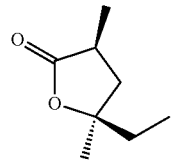

(+)-(3S,5R)-5-ethyl-3,5-dimethyldihydrofuran-2(3H)-one (5). $^1H$ NMR (500 MHz, CDCl$_3$) δ 2.87-2.78 (m, 1H), 2.20 (dd, J=12.5, 9.0 Hz, 1H), 1.76-1.67 (m, 3H), 1.34 (s, 3H), 1.27 (d, J=7.0 Hz, 3H), 0.96 (t, J=7.5 Hz, 3H); HRMS (ESI) m/z calc'd for C$_8$H$_{15}$O$_3$ [M+H]$^+$: 143.1072, found 143.1075; [α]$_D^{25}$=+3.3° (c=0.8, CHCl$_3$). These spectral data match those reported in the literature (Chen and White, *Science* 2007, 318, 783).

TABLE 2.1

Catalyst Comp. for the Oxidation of (+)-(2S,4S)-methyl 2,4-dimethylhexanoate (3).

| Catalyst | % isolated yield (+)-4 | % isolated yield (+)-5 | % isolated yield RSM | 2°:3°[b] |
|---|---|---|---|---|
| (S,S)—Fe(PDP) (1)* | 41 | 27 | 16 | 1.5:1 |
| (S,S)—Fe(CF$_3$-PDP) (2)[c] | 51 | 11 | 8 | 4:1 |

*Methods for preparing complex 1 are described in U.S. Pat. No. 7,829,342 (White et al.).
[a]Average of 3 runs at 1.0 mmol.
[b]Crude ratio determined by GC.
[c]Starting material was recycled 1 time.

Reaction 2. Oxidation of trans-1,2-Dimethylcyclohexane

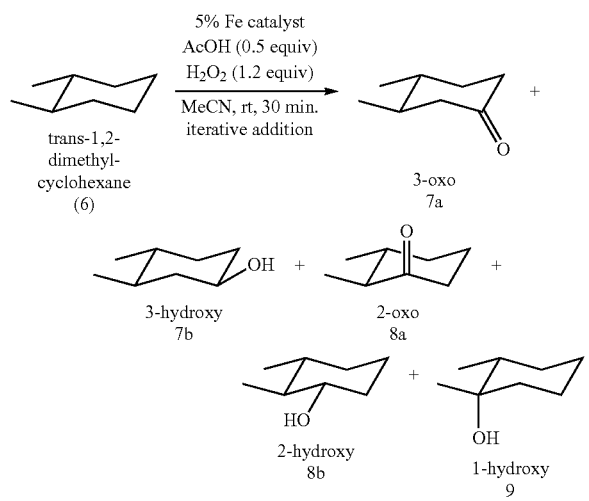

GC Yield Data. Run 1: 16% RSM, 39% 7a, 6% 7b, 22% 8a, 5% 8b, 7% 9, 9.1:1 2°:3°. Run 2: 17% RSM, 38% 7a, 8% 7b, 22% 8a, 6% 18b, 9% 9, 8.7:1 2°:3°. Run 3: 12% RSM, 36% 7a, 5% 7b, 20% 8a, 4% 8b, 6% 9, 10.9:1 2°:3°. Average RSM: 15±3%. Average 7a: 38±1%. Average 7b: 6±2%. Average 8a: 21±1%. Average 8b: 5±1%. Average 9: 7±1%. Average 2°:3°: 9.9±1:1.

Data for (S,S)—Fe(PDP) (1) have been previously reported (Chen and White, *Science* 2010, 327, 566).

trans-3,4-dimethylcyclohexanone (7a). trans-1,2-dimethylcyclohexane (6) (33.7 mg, 0.3 mmol, 1.0 equiv, Sigma-Aldrich) was reacted with (S,S)—Fe(CF$_3$-PDP) (2) according to general procedure A with nitrobenzene (60 mol %) added as an internal standard. Yields were determined by GC analysis of the crude reaction mixture after reaction completion. All product yields are calibrated for response factors relative to starting material, rounded to the nearest whole number and the average of three runs. $^1$H NMR (500 MHz, CDCl$_3$) δ 2.36-2.31 (m, 3H), 2.05 (dd, J=11.0, 9.5 Hz, 1H), 2.00-1.96 (m, 1H), 1.54-1.34 (m, 3H), 1.01 (d, J=6.0 Hz, 3H), 0.91 (d, J=6.0 Hz, 3H).

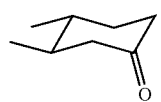

trans-3,4-dimethylcyclohexan-1-ol (7b). $^1$H NMR (500 MHz, CDCl$_3$) δ 3.59 (tt, J=11.0, 4.0 Hz, 1H), 1.98-1.87 (m, 2H), 1.68 (dq, J=13.0, 3.0 Hz, 1H), 1.35 (br s, 1H), 1.26-1.08 (m, 2H), 1.10-0.96 (m, 4H), 0.94-0.84 (m, 6H). These spectral data are in agreement with those previously reported in the literature (Kamata et al., *Nature Chem.* 2010, 2, 478).

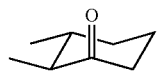

trans-2,3-dimethylcyclohexanone (8a). $^1$H NMR (500 MHz, CDCl$_3$) δ 2.38-2.28 (m, 3H), 2.06-1.98 (m, 1H), 1.88-1.83 (m, 1H), 1.48-1.30 (m, 3H), 1.06 (d, J=6.0 Hz, 3H), 1.03 (d, J=6.5 Hz, 3H).

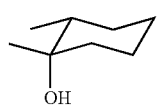

trans-2,3-dimethylcyclohexan-1-ol (8b). $^1$H NMR (500 MHz, CDCl$_3$) δ 3.14 (td, J=10.0, 4.0 Hz, 1H), 1.99-1.93 (m, 1H), 1.76-1.67 (m, 2H), 1.61-1.54 (m, 1H), 1.44-1.16 (m, 4H), 1.25 (s, 1H), 1.03 (d, J=6.5 Hz, 3H), 0.93 (d, J=6.0 Hz, 3H). These spectral data are in agreement with those previously reported in the literature (Kamata et al., *Nature Chem.* 2010, 2, 478).

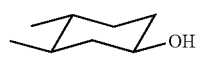

trans-1,2-dimethylcyclohexan-1-ol (9). $^1$H NMR (500 MHz, CDCl$_3$) δ 1.68-1.62 (m, 2H), 1.54-1.48 (m, 2H), 1.46-1.20 (m, 5H), 1.18 (s, 3H), 0.90 (s, J=6.5 Hz, 3H).

Reaction 3. Oxidation of trans-4-Methylcyclohexyl acetate

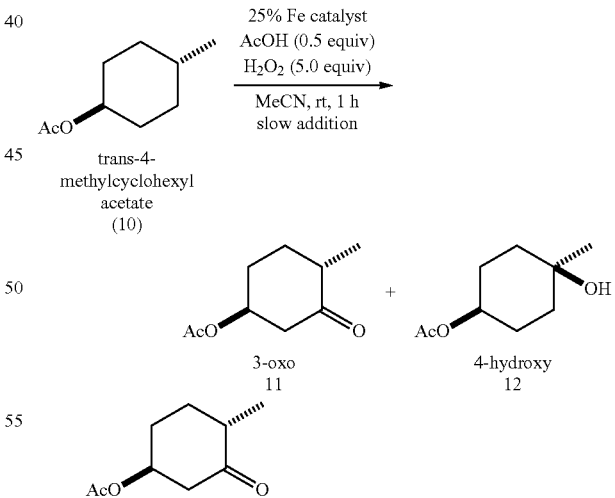

trans-4-methyl-3- and 5-oxocyclohexyl acetate (11). Trans-4-methylcyclohexyl acetate (10) (46.9 mg, 0.3 mmol, 1.0 equiv) in MeCN (0.5 mL) was reacted with (S,S)—Fe(CF$_3$-PDP) (2) according to Method B. Purification by flash chromatography on silica (~75 mL) eluting with gradient 10→30% acetone/hexane. Run 1: 11 (25.2 mg, 0.15 mmol, 49%), 12 (15.5 mg, 0.09 mmol, 30%), RSM (3.4 mg, 0.022 mmol, 7%), 2.0:1 crude 2°:3° by GC. Run 2: 11 (26.1 mg, 0.15 mmol, 51%), 12 (14.3 mg, 0.083 mmol, 28%), RSM (2.7 mg, 0.027 mmol, 9%), 2.4:1 crude 2°:3° by GC. Run 3: 11 (27.3 mg, 0.16 mmol, 53%), 12 (12.9 mg, 0.076 mmol, 25%), RSM (5.5 mg, 0.035 mmol, 12%), 2.2:1 crude 2°:3° by GC. Average isolated 11: 51±2%. Average isolated 12: 28±3%. Average isolated RSM: 9±3%. Average crude 2°:3° by GC: 2.2±0.2:1. $^1$H NMR (500 MHz, CDCl$_3$) δ 4.94 (app septet, J=5.0 Hz, 1H), 2.77 (ddd, J=13.5, 5.0, 2.0 Hz, 1H), 2.44-2.38 (m, 1H), 2.36-2.31 (m, 1H), 2.23-2.18 (m, 1H), 2.09-2.02 (m, 1H), 2.04 (s, 3H), 1.79-1.71 (m, 1H), 1.38-1.28 (m, 1H), 1.05 (d, J=6.5 Hz, 3H); $^{13}$C NMR (125 MHz, CDCl$_3$) δ 208.8, 170.0, 71.6, 46.8, 44.1, 30.2, 29.1, 21.1, 14.2; IR (film): 2937, 2872, 1738, 1718, 1454, 1431, 1379, 1362, 1240, 1215, 1053, 1032 cm$^{-1}$; HRMS (ESI) m/z calc'd for C$_9$H$_{14}$O$_3$Na [M+Na]$^+$: 193.0841, found 193.0841.

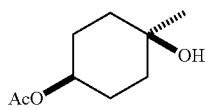

trans-4-hydroxy-4-methylcyclohexyl acetate (12). $^1$H NMR (500 MHz, CDCl$_3$) δ 4.69 (app p, J=6.5 Hz, 1H), 2.03 (s, 3H), 1.77-1.66 (m, 6H), 1.51-1.44 (m, 2H), 1.23 (s, 3H); $^{13}$C NMR (125 MHz, CDCl$_3$) δ 170.7, 72.0, 68.5, 36.5, 30.0, 27.1, 21.4; IR (film): 3454, 2939, 2872, 1730, 1446, 1365, 1250, 1169, 1138, 1036, 955, 916 cm$^{-1}$; HRMS (ESI) m/z calc'd for C$_9$H$_{15}$O$_3$Na [M+Na]$^+$: 195.0997, found 195.0997.

TABLE 2.2

Catalyst Comparison for the Oxidation of trans-4-Methylcyclohexanol acetate (10)

| Catalyst | % isolated yield 11 | % isolated yield 12 | % isolated yield RSM | 2°:3°[b] |
|---|---|---|---|---|
| (S,S)—Fe(PDP) (1) | 19 | 66 | 0 | 1:2.2 |
| (S,S)—Fe(CF$_3$-PDP) (2) | 51 | 28 | 9 | 2.2:1 |

[a]Average of 3 runs at 0.3 mmol.
[b]Crude ratio determined by GC.

Oxidation with (S,S)—Fe(PDP) (1) according to Method B. Run 1: 11 (9.4 mg, 0.055 mmol, 18%), 12 (35.4 mg, 0.21 mmol, 69%), 1:2.2 crude 2°:3° by GC. Run 2: 11 (9.3 mg, 0.055 mmol, 18%), 12 (33.2 mg, 0.19 mmol, 64%), 1:2.1 crude 2°:3° by GC. Run 3: 11 (10.5 mg, 0.062 mmol, 21%), 12 (33.8 mg, 0.2 mmol, 65%), 1:2.2 crude 2°:3° by GC. Average isolated 11: 19±2%. Average isolated 12: 66±2%. Average crude 2°:3° by GC: 1:2.2±0.1.

Reaction 4. Oxidation of L-N-nosyl-isoleucine methyl ester (4-(((2S,3S)-1-methoxy-3-methyl-1-oxopentan-2-yl)amino)-3-nitrobenzenesulfonic acid)

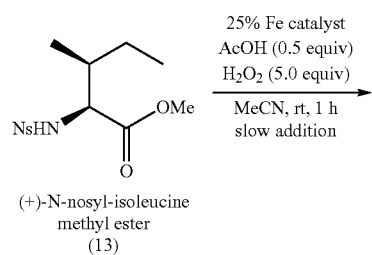

(+)-N-nosyl-isoleucine methyl ester (13)

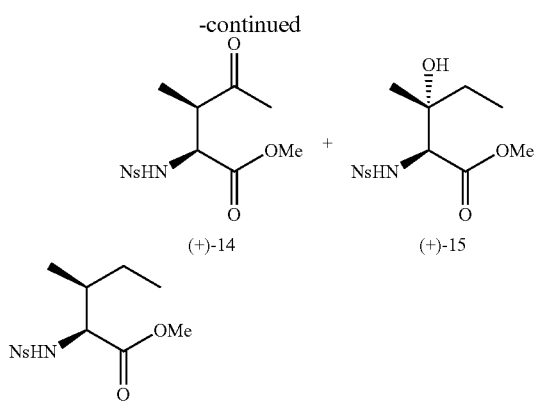

(+)-4-(((2S,3S)-1-methoxy-3-methyl-1-oxopentan-2-yl) amino)-3-nitrobenzenesulfonic acid (13). $^1$H NMR (500 MHz, CDCl$_3$) δ 8.34 (d, J=9.0 Hz, 2H), 8.02 (d, J=9.0 Hz, 2H), 5.27 (d, J=9.5 Hz, 1H), 3.88 (dd, J=10.0, 5.5 Hz, 1H), 3.50 (s, 3H), 1.86-1.80 (m, 1H), 1.41-1.35 (m, 1H), 1.18-1.12 (m, 1H), 0.92 (d, J=7.0 Hz, 3H), 0.88 (t, J=7.0 Hz, 3H); $^{13}$C NMR (125 MHz, CDCl$_3$) δ 171.4, 150.1, 145.6, 128.5, 124.2, 60.4, 52.4, 38.3, 24.5, 15.4, 11.3; IR (film): 1734, 1709, 1523, 1352, 1173, 1092 cm$^{-1}$; HRMS (ESI) m/z calc'd for C$_{13}$H$_{18}$N$_2$O$_6$NaS [M+Na]$^+$: 353.0783, found 353.0789; [α]$_D^{25}$=+45.8° (c=1.0, CHCl$_3$).

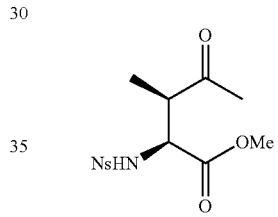

(+)-4-(((2S,3R)-1-methoxy-3-methyl-1,4-dioxopentan-2-yl)amino)-3-nitrobenzenesulfonic acid (14). (+)-L-N-nosyl-isoleucine methyl ester (13) (173.2 mg, 0.5 mmol, 1.0 equiv) in MeCN (0.75 mL) was reacted with (R,R)—Fe(CF$_3$-PDP) (2) according to Method B. Purification by flash chromatography on silica (~75 mL) eluting with gradient 5→10→20% EtOAc/CH$_2$Cl$_2$. Run 1: recycled 1 time for a total of 58% (+)-14, 14% (+)-15, 7% RSM, 4.1:1 isolated 2°:3°; cycle 1 (+)-14 (79.8 mg, 0.22 mmol, 44%), (+)-15 (19.9 mg, 0.05 mmol, 11%), RSM (51.9 mg, 0.15 mmol, 30%); cycle 2 (+)-14 (25.4 mg, 0.07 mmol, 47%), (+)-15 (8.2 mg, 0.02 mmol, 15%), RSM (11.4 mg, 0.03 mmol, 22%). Run 2: recycled 1 time for a total of 52% (+)-14, 17% (+)-15, 7% RSM, 3.1:1 isolated 2°:3°; cycle 1 (+)-14 (80.0 mg, 0.22 mmol, 46%), (+)-15 (24.6 mg, 0.07 mmol, 14%), RSM (37.1 mg, 0.1 mmol, 20%); cycle 2 (+)-14 (13.5 mg, 0.04 mmol, 33%), (+)-15 (5.3 mg, 0.01 mmol, 13%), RSM (12.5 mg, 0.04 mmol, 33%). Run 3: recycled 1 time for a total of 58% (+)-14, 14% (+)-15, 10% RSM, 4.1:1 isolated 2°:3°; cycle 1 (+)-14 (77.0 mg, 0.22 mmol, 45%), (+)-15 (18.0 mg, 0.052 mmol, 10%), RSM (54.7 mg, 0.17 mmol, 33%); cycle 2 (+)-14 (24.8 mg, 0.049 mmol, 42%), (+)-15 (6.5 mg, 0.019 mmol, 11%), RSM (16.3 mg, 0.049 mmol, 29%). Average overall yield (+)-14: 56±4%. Average overall yield (+)-15: 15±2%. Average overall RSM: 7±2%. Average 2°:3°: 3.8±0.6:1. $^1$H NMR (500 MHz, CDCl$_3$) δ 8.34 (d, J=8.5 Hz, 2H), 8.05 (d, J=9.0 Hz, 2H), 5.91 (d, J=10.0 Hz, 1H), 4.03 (dd, J=10.0, 3.5 Hz, 1H), 3.44 (s, 3H), 3.34 (qd, J=7.5, 4.0 Hz, 1H), 2.18 (s, 3H), 1.37 (d, J=7.5 Hz, 3H); $^{13}$C NMR (125 MHz, CDCl$_3$) δ 210.7, 170.3, 150.0, 146.3, 128.5, 124.0, 60.4, 57.9, 48.7, 28.0, 13.8; IR (film): 3525, 3284, 2974, 2951, 1738, 1531, 1435, 1352, 1313, 1211, 1169, 1092, 930, 856 cm$^{-1}$; HRMS (ESI) m/z calc'd for C$_{13}$H$_{16}$N$_2$O$_7$NaS [M+Na]$^+$: 367.0576, found 367.0581; $[α]_D^{25}$=+62.6° (c=1.0, CHCl$_3$).

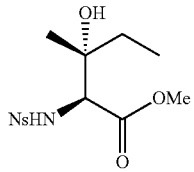

(+)-4-(((2S,3R)-3-hydroxy-1-methoxy-3-methyl-1-oxo-pentan-2-yl)amino)-3-nitrobenzenesulfonic acid (15). $^1$H NMR (500 MHz, CDCl$_3$) δ 8.33 (d, J=9.0 Hz, 2H), 8.03 (d, J=8.5 Hz, 2H), 6.04 (br s, 1H), 3.90 (br s, 1H), 3.45 (s, 3H), 2.37 (br s, 1H), 1.69-1.58 (m, 1H), 1.15 (s, 3H), 0.89 (t, J=7.5 Hz, 3H); $^{13}$C NMR (125 MHz, CDCl$_3$) δ 170.9, 150.1, 145.6, 128.5, 124.1, 74.1, 61.4, 52.3, 31.2, 23.3, 7.7; IR (film): 3438, 1741, 1707, 1639, 1531, 1352, 1311, 1167, 1093, 854 cm$^{-1}$; HRMS (ESI) m/z calc'd for C$_{13}$H$_{18}$N$_2$O$_7$NaS [M+Na]$^+$: 369.0732, found 369.0739; $[α]_D^{25}$=+28.0° (c=2.0, CHCl$_3$).

TABLE 2.3

Catalyst Comparison for the Oxidation of (+)-L-N-nosyl-isoleucine methyl ester (13).

| Catalyst | % isolated yield (+)-14 | % isolated yield (+)-15 | % isolated yield RSM | 2°:3°[a,b] |
|---|---|---|---|---|
| (R,R)—Fe(PDP) (1) | 29 | 43 | 10 | 1:2 |
| (R,R)—Fe(CF$_3$-PDP) (2) | 56 | 15 | 8 | 4:1 |

[a]Average of 3 runs at 0.5 mmol.
[b]Isolated ratio.

Oxidation with (R,R)—Fe(PDP) (1) according to Method B. Run 1: recycled 1 time for a total of 30% (+)-14, 43% (+)-15, 10% RSM, 1:1.5 isolated 2°:3°; cycle 1 (+)-14 (39.6 mg, 0.11 mmol, 22%), (+)-15 (58.9 mg, 0.16 mmol, 33%), RSM (60.8 mg, 0.18 mmol, 35%); cycle 2 (+)-14 (12.3 mg, 0.05 mmol, 19%), (+)-15 (18.3 mg, 0.05 mmol, 29%), RSM (16.8 mg, 0.05 mmol, 27%). Run 2: recycled 1 time for a total of 27% (+)-14, 41% (+)-15, 7% RSM, 1:1.6 isolated 2°:3°; cycle 1 (+)-14 (36.5 mg, 0.10 mmol, 20%), (+)-15 (57.5 mg, 0.16 mmol, 32%), RSM (51.9 mg, 0.15 mmol, 30%); cycle 2 (+)-14 (12.5 mg, 0.035 mmol, 23%), (+)-15 (18.5 mg, 0.051 mmol, 34%), RSM (12.2 mg, 0.035 mmol, 23%). Run 3: recycled 1 time for a total of 29% (+)-14, 46% (+)-15, 12% RSM, 1:1.6 isolated 2°:3°; cycle 1 (+)-14 (34.8 mg, 0.10 mmol, 20%), (+)-15 (57.5 mg, 0.166 mmol, 33%), RSM (62.9 mg, 0.19 mmol, 38%); cycle 2 (+)-14 (15.2 mg, 0.044 mmol, 23%), (+)-15 (22.0 mg, 0.064 mmol, 33%), RSM (21.6 mg, 0.65 mmol, 34%). Average overall yield (+)-14: 29±2%. Average overall yield (+)-15: 43±3%. Average overall RSM: 10±3%. Average 2°:3°: 1:1.5±0.1.

Reaction 5. Oxidation of MeO-Val-Nva-Ns

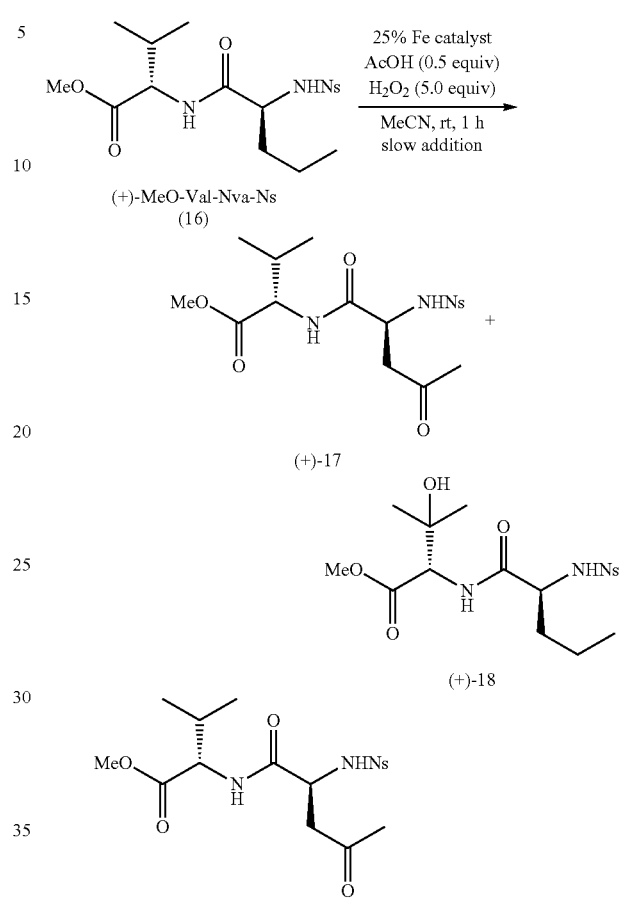

(+)-MeO-Val-(γ-oxo-Nva)-Ns (17). (+)-MeO-Val-Nva-Ns (16) (207.7 mg, 0.5 mmol, 1.0 equiv) in MeCN (0.75 mL) was reacted with (R,R)—Fe(CF$_3$—PDP) (2) according to Method B. Purification by flash chromatography on silica (~125 mL) eluting with 25% acetone/hexane. Run 1: recycled 1 time for a total of 48% (+)-17, 6% (+)-18, 8% RSM, 8.3:1 2°:3° by 1H NMR; cycle 1 (+)-17 (82.6 mg, 0.19 mmol, 38%), (+)-18 (9.9 mg, 0.023 mmol, 5%), RSM (54.6 mg, 0.13 mmol, 26%); cycle 2 (+)-17 (21.5 mg, 0.05 mmol, 31%%), (+)-18 (2.6 mg, 0.006 mmol, 4%), RSM (16.8 mg, 0.04 mmol, 31%). Run 2: recycled 1 time for a total of 51% (+)-17, 6% (+)-18, 6% RSM, 9.0:1 2°:3° by 1H NMR; cycle 1 (+)-17 (87.7 mg, 0.20 mmol, 41%), (+)-18 (9.7 mg, 0.022 mmol, 4%), RSM (60.0 mg, 0.14 mmol, 29%); cycle 2 (+)-17 (22.5 mg, 0.052 mmol, 37%), (+)-18 (2.2 mg, 0.005 mmol, 4%), RSM (11.6 mg, 0.028 mmol, 20%). Average overall (+)-17: 51±3%. Average overall (+)-18: 6±0.5%. Average overall RSM: 8±3%. Average overall 2°:3°: 8.9±0.6:1. $^1$H NMR (500 MHz, CDCl$_3$) δ 8.35 (d, J=9.0 Hz, 2H), 8.07 (d, J=8.5 Hz, 2H), 6.91 (d, J=9.0 Hz, 1H), 6.25 (br s, 1H), 4.27 (dd, J=9.0, 4.5 Hz, 1H), 4.21 (d, J=4.5 Hz, 1H), 3.67 (s, 3H), 3.23 (dd, J=18.5, 3.0 Hz, 1H), 2.81 (dd, J=18.5, 7.5 Hz, 1H), 2.20 (s, 3H), 2.11-2.06 (m, 1H), 0.80 (t, J=6.5 Hz, 3H); $^{13}$C NMR (125 MHz, CDCl$_3$) δ 208.4, 171.5, 169.3, 150.3, 145.3, 128.5, 124.5, 57.6, 52.2, 51.9, 46.5, 30.5, 30.2, 18.8, 17.3; IR (film): 3284, 3109, 2966, 2877, 1739, 1716, 1668, 1531, 1437, 1352, 1313, 1213, 1167, 1093, 1012, 918 cm$^{-1}$; HRMS (ESI) m/z calc'd for $C_{17}H_{24}N_3O_8S$ [M+H]$^+$: 430.1284, found 430.1279; $[\alpha]_D^{25}$=+74.2° (c=1.4, CHCl$_3$).

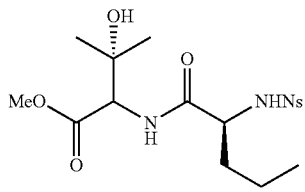

(+)-MeO-(β-hydroxy-Val)-Nva-Ns (18). Purification by MPLC on silica (24 g) eluting with 5→20% acetone/hexane. $^1$H NMR (500 MHz, CDCl$_3$) δ 8.33 (d, J=9.0 Hz, 2H), 8.07 (d, J=8.5 Hz, 2H), 6.82 (d, J=9.0 Hz, 1H), 5.99 (d, J=7.5 Hz, 1H), 4.35 (d, J=9.0 Hz, 1H), 3.91-3.84 (m, 1H), 3.75 (s, 3H), 2.71 (br s, 1H), 1.72-1.64 (m, 2H), 1.62-1.52 (m, 1H), 1.28-1.24 (m, 1H), 1.22 (s, 3H), 1.04 (s, 3H), 0.84 (t, J=7.0 Hz, 3H); $^{13}$C NMR (125 MHz, CDCl$_3$) δ 171.5, 171.0, 150.1, 145.7, 128.5, 124.3, 71.9, 59.6, 56.7, 52.5, 35.7, 26.8, 26.5, 18.4, 13.5; IR (film): 33.63, 3107, 2962, 2933, 2875, 1739, 1666, 1531, 1437, 1352, 1311, 1209, 1167, 1093 cm$^{-1}$; HRMS (ESI) m/z calc'd for $C_{17}H_{26}N_3O_8S$ [M+H]$^+$: 432.1441, found 432.1437; $[\alpha]_D^{25}$=+18.2° (c=1.0, CHCl$_3$).

TABLE 2.4

Catalyst Comparison for the Oxidation of (+)-MeO-Val-Nva-Ns (16).

| Catalyst | % isolated yield (+)-17 | % isolated yield (+)-18 | % isolated yield RSM | 2°:3°[a,b] |
|---|---|---|---|---|
| (R,R)—Fe(PDP) (1)[a] | 24 | 27 | 32 | 1:1 |
| (R,R)—Fe(CF$_3$-PDP) (2)[a] | 51 | 6 | 8 | 9:1 |

[a] Average of 3 runs at 0.5 mmol.
[b] Ratio determined by $^1$H NMR.

Oxidation with (R,R)—Fe(PDP) (1) according to Method B. Run 1: recycled 1 time for a total of 24% (+)-17, 24% (+)-18, 32% RSM, 1:1 2°: 3° by 1H NMR; cycle 1 (+)-17 (30.8 mg, 0.072 mmol, 14%), (+)-18 (30.9 mg, 0.072 mmol, 14%), RSM (130.5 mg, 0.31 mmol, 63%); cycle 2 (+)-17 (21.4 mg, 0.05 mmol, 16%), (+)-18 (21.5 mg, 0.05 mmol, 16%), RSM (65.6 mg, 0.16 mmol, 51%). Run 2: recycled 1 time for a total of 23% (+)-17, 27% (+)-18, 35% RSM, 1:1.2 2°: 3° by 1H NMR; cycle 1 (+)-17 (29.8 mg, 0.069 mmol, 14%), (+)-18 (35.8 mg, 0.083 mmol, 17%), RSM (129.0 mg, 0.31 mmol, 62%); cycle 2 (+)-17 (19.6 mg, 0.46 mmol, 15%), (+)-18 (23.5 mg, 0.054 mmol, 18%), RSM (73.7 mg, 0.18 mmol, 57%). Average overall (+)-17: 24±2%. Average overall (+)-18: 27±3%. Average overall RSM: 32±3%. Average overall 2°:3°: 1:1±0.1.

TABLE 2.5

Additional Examples of Catalyst-Controlled Oxidation of Simple Cyclic and Acyclic Molecules.

| entry (catalyst) | starting material % RSM | oxidation products % yield[a,b,c] | | | product ratio[d] |
|---|---|---|---|---|---|
| | S1[e] | S2 | S3 | S4 | distal:proximal |
| 1 (1) | 15 | 17 | 32 | 21 | 2:1 |
| 2 (2) | 21 | 14 | 47[f] | 11 | 6:1 |
| | (+)-S5 | (−)-S6 | | (+)-S7 | 2':3' |
| 3 (1) | 23 | 17 | | 48 | 1:3 |
| 4 (2) | 28 | 24 | | 31 | 1:1.4 |

TABLE 2.5-continued

Additional Examples of Catalyst-Controlled Oxidation of Simple Cyclic and Acyclic Molecules.

| entry (catalyst) | starting material % RSM | | oxidation products % yield[a,b,c] | | | product ratio[d] |
|---|---|---|---|---|---|---|
| | S8[e] | S9 | S10 | S11 | | 2':3' |
| 5 (1) | 12 | 6 | 9 | 55 | | 1:4 |
| 6 (2) | 13 | 20 | 12 | 33 | | 1:1.1 |

[a] Average of 3 runs.
[b] Yields are of isolated material unless otherwise noted.
[c] Method A: Iterative addition of 5% Fe catalyst, AcOH (0.5 equiv) and H$_2$O$_2$ (1.2 equiv).
[d] Crude ratio determined by GC analysis.
[e] Yield determined by GC analysis.
[f] Includes 18% 3β-hydroxy product.

Reaction 6. Oxidation of 1,1-Dimethylcyclohexane

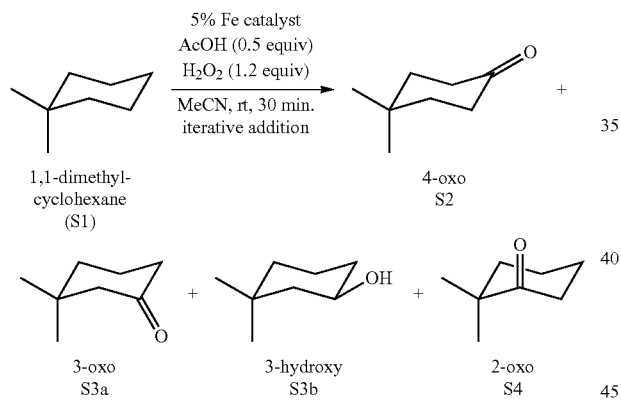

1,1-dimethyl-cyclohexane (S1)

4-oxo S2

3-oxo S3a 3-hydroxy S3b 2-oxo S4

GC Yield Data. Run 1: 16% RSM, 16% S2, 35% S3a, 17% S3b, 13% S4, 5.3:1 distal:proximal. Run 2: 24% RSM, 14% S2, 28% S3a, 20% S3b, 11% S4, 5.8:1 distal:proximal. Run 3: 23% RSM, 13% S2, 26% S3a, 18% S3b, 10% S4, 5.6:1 distal:proximal. Average RSM: 21±4%. Average S2: 14±2%. Average S3a: 29±5%. Average S3b: 18±2%. Average S4: 11±2%. Average distal:proximal: 5.6±0.3:1. Data for (S,S)—Fe(PDP) (1) have been previously reported (Chen and White, *Science* 2010, 327, 566).

4,4-dimethylcyclohexanone (S2). 1,1-dimethylcyclohexane (S1) (33.7 mg, 0.3 mmol, 1.0 equiv, Sigma-Aldrich) was reacted with (S,S)—Fe(CF$_3$-PDP) (2) according to Method A with nitrobenzene (60 mol %) added as an internal standard. Yields were determined by GC analysis of the crude reaction mixture after reaction completion. All product yields are calibrated for response factors relative to starting material, rounded to the nearest whole number and the average of three runs. $^1$H NMR (400 MHz, CDCl$_3$) δ 2.34 (t, J=6.8 Hz, 4H), 1.67 (app t, J=7.2 Hz, 4H), 1.09 (s, 6H).

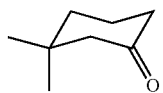

3,3-dimethylcyclohexanone (S3a). $^1$H NMR (400 MHz, CDCl$_3$) δ 2.26 (app t, J=6.8 Hz, 2H), 2.15 (s, 2H), 1.91-1.84 (m, 2H), 1.59-1.57 (m, 2H), 0.97 (s, 6H).

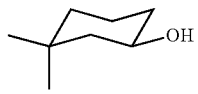

3,3-dimethylcyclohexanol (S3b). $^1$H NMR (500 MHz, CDCl$_3$) δ 3.78-3.68 (m, 1H), 1.98-1.91 (m, 1H), 1.71-1.57 (m, 2H), 1.49-1.37 (m, 1H), 1.32-1.24 (m, 2H), 1.13-1.01 (m, 2H), 0.95 (s, 3H), 0.89 (s, 3H). These spectral data match those reported in the literature (Kamata et al., *Nature Chem.* 2010, 2, 478).

2,2-dimethylcyclohexanone (S4). $^1$H NMR (400 MHz, CDCl$_3$) δ 2.39 (app t, J=6.8 Hz, 2H), 1.86-1.80 (m, 2H), 1.77-1.70 (m, 2H), 1.68-1.64 (m, 2H), 1.11 (s, 6H).

Reaction 7. Oxidation of (S)-Methyl 4-methylhexanoate

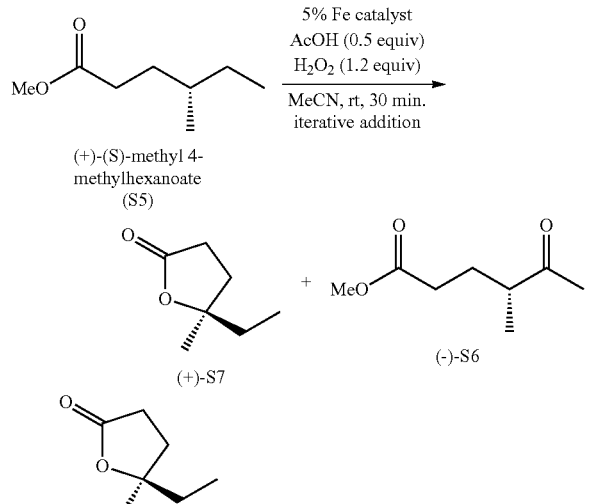

(+)-(R)-5-ethyl-5-methyldihydrofuran-2(3H)-one (S7). (+)-(S)-methyl 4-methylhexanoate (S5) (72.1 mg, 0.5 mmol, 1.0 equiv) was reacted with (S,S)—Fe(CF$_3$-PDP) (2) according to Method A. Purification by flash chromatography on silica (~75 mL) eluting with 30% Et$_2$O/pet ether. Run 1: 30% (+)-S7 (19.7 mg, 0.15 mmol, 30%), (−)-S6 (19.8 mg, 0.13 mmol, 25%), RSM (23.4 mg, 0.16 mmol, 32%), 1.5:1 crude 3°:2° by GC. Run 2: (+)-S7 (21.5 mg, 0.17 mmol, 34%), (−)-S6 (17.7 mg, 0.11 mmol, 22%), RSM (19.2 mg, 0.13 mmol, 27%), 1.4:1 crude 3°:2° by GC. Run 3: (+)-S7 (18.6 mg, 0.15 mmol, 29%), (−)-S6 (19.0 mg, 0.12 mmol, 24%), RSM (18.1 mg, 013 mmol, 25%), 1.2:1 crude 3°:2° by GC. Average (+)-S7: 31±3%. Average (−)-S7 24±2%. Average RSM: 28±4%. Average crude 3°:2°: 1.4±0.2:1. $^1$H NMR (500 MHz, CDCl$_3$) δ 2.67-2.54 (m, 2H), 2.12-2.05 (m, 1H), 1.99-1.93 (m, 1H), 1.77-1.64 (m, 2H), 1.38 (s, 3H), 0.97 (t, J=8.0 Hz, 3H); HRMS (ESI) m/z calc'd for C$_7$H$_{13}$O$_2$ [M+H]$^+$: 129.0916, found 129.0913; [α]$_D^{25}$=+9.0° (c=1.0, CHCl$_3$). These spectral data match those reported in the literature (Chen and White, *Science* 2007, 318, 783).

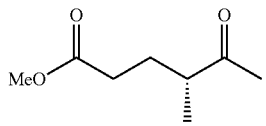

(−)-(R)-methyl 4-methyl-5-oxohexanoate (S6). $^1$H NMR (500 MHz, CDCl$_3$) δ 3.66 (s, 3H), 2.65-2.53 (m, 1H), 2.35-2.25 (m, 2H), 2.15 (s, 3H), 2.05-1.95 (m, 1H), 1.60-1.72 (m, 1H), 1.10 (d, J=7.0 Hz, 3H); HRMS (ESI) m/z calc'd for C$_8$H$_{15}$O$_3$ [M+H]$^+$: 159.1021, found 159.1026; [α]$_D^{24}$=−1.2° (c=1.2, CHCl$_3$). These spectral data match those reported in the literature (Chen and White, *Science* 2007, 318, 783).

TABLE 2.6

Catalyst Comparison for the Oxidation of (+)-(S)-methyl 4-methylhexanoate (S5).

| Catalyst | % isolated yield (+)-S7[a] | % isolated yield (−)-S6 | % isolated yield RSM | 3°:2°[b] |
|---|---|---|---|---|
| (S,S)—Fe(PDP) (1) | 48 | 17 | 23 | 3:1 |
| (S,S)—Fe(CF$_3$-PDP) (2) | 31 | 24 | 28 | 1.4:1 |

[a]Average of 3 runs at 0.5 mmol.
[b]Crude ratio determined by GC.

Reaction 8. Oxidation of cis-1,2-Dimethylcyclohexane

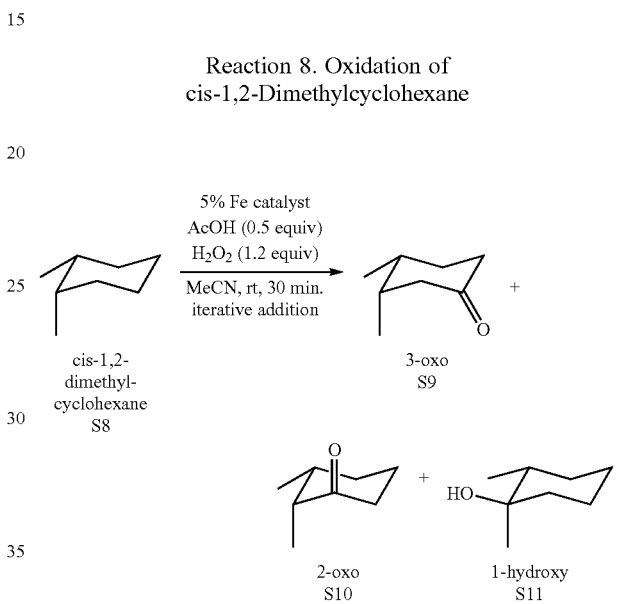

GC Yield Data. Run 1: 16% RSM, 20% S9, 17% S10, 35% S11, 1:1.2 2°:3°. Run 2: 16% RSM, 20% S9, 10% S10, 34% S11, 1:1.2 2°:3°. Run 3: 9% RSM, 19% S9, 10% S10, 30% S11, 1:1 2°:3°. Average RSM: 13±4%. Average S9: 20±1%. Average S10: 12±1%. Average S11: 33±3%. Average 2°:3°: 1:1.1±0.1.

Data for (S,S)—Fe(PDP) (1) have been previously reported (Chen and White, *Science* 2010, 327, 566).

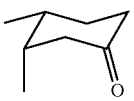

cis-3,4-dimethylcyclohexanone (S9). cis-1,2-dimethylcyclohexane (S8) (33.7 mg, 0.3 mmol, 1.0 equiv, Sigma-Aldrich) was reacted with (S,S)—Fe(CF$_3$-PDP) (2) according to Method A with nitrobenzene (60 mol %) added as an internal standard. Yields were determined by GC analysis of the crude reaction mixture after reaction completion. All product yields are calibrated for response factors relative to material, rounded to the nearest whole number and the average of three runs. $^1$H NMR (500 MHz, CDCl$_3$) δ 2.41-2.37 (m, 1H), 2.36-2.24 (m, 2H), 2.21-2.11 (m, 2H), 2.08-2.20 (m, 1H), 1.85-1.79 (m, 1H), 1.76-1.68 (m, 1H), 1.00 (d, J=7.0 Hz, 3H), 0.88 (d, J=7.0 Hz, 3H).

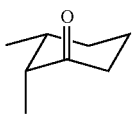

cis-2,3-dimethylcyclohexanone (S10). ¹H NMR (500 MHz, CDCl₃) δ 2.61-2.55 (m, 1H), 2.38-2.33 (m, 1H), 2.28-2.20 (m, 2H), 1.94-1.81 (m, 3H), 1.68-1.63 (m, 1H), 0.99 (d, J=7.0 Hz, 3H), 0.84 (d, J=7.0 Hz, 3H).

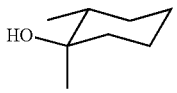

cis-1,2-dimethylcyclohexan-1-ol (S11). ¹H NMR (500 MHz, CDCl₃) δ 1.72 (m, 3H), 1.52-1.44 (m, 1H), 1.42 (s, 1H), 1.38-1.22 (m, 5H), 1.07 (s, 3H), 0.90 (d, J=7.0 Hz, 3H).

Example 3

Methods for Electronic, Steric and Stereoelectronic Analysis

The following description provides details for computational models developed to predict the site-selectivity of oxidation on complex molecules, for example, oxidation by the catalyst systems described herein, other electrophilic C—H oxidation catalysts, as well as enzymes. The computational models may also be useful as probes of metabolism oxidations.

Computational Details. The lowest energy conformations of each molecule were located using a stochastic search and MMFF94X force field in Molecular Operating Environment (MOE) version 11 (*Molecular Operating Environment (MOE)*, 2011.10, (Chemical Computing Group Inc., Montreal, QC, Canada, 2011)). Up to the five lowest energy conformers were submitted to further geometry optimization in Gaussian 09 (Frisch et al., *Gaussian 09, Revision B.01*, (Gaussian, Inc., Wallingford, C T, 2010)) using B3LYP/6-31G(d) to locate the global minimum.

A natural population analysis (NPA) was performed on the energy minimized structure (B3LYP/6-311++G(d,p)) to obtain natural partial atomic charges for all hydrogen atoms. Lower values indicate the site is more electron rich, i.e. smaller positive charge. The expanded basis set was necessary to obtain accurate partial charge data that provides good correlation with the experimental results described herein and reported by Chen and White (*Science* 2007, 318, 783; *Science* 2010, 327, 566) using Fe(PDP) (1) and Fe(CF₃-PDP) (2). The only exceptions are C—H bonds attached to heteroatoms.

For example, the C—H bond at C1 in trans-4-methylcyclohexyl acetate (10) has an NPA value of 0.194 compared to 0.203 and 0.183 at C3/5 and C4 respectively. Yet, no oxidation at C1 was observed with either catalyst 1 or 2. Similar discrepancies are obtained for other molecules. This discrepancy is likely the result of the σ→σ* hyperconjugation term included in NPA calculations. The effect of hyperconjugative activation of a C—H bond by a heteroatom towards oxidation is well known (for example the oxidation of ethereal positions); however, NPA calculations seem to be overestimating the magnitude of this activation for inductively withdrawing heteroatom containing groups (e.g. OAc, OPiv, etc.). Experimentally, universally no oxidation was observed at these sites indicating that the inductive withdrawing characteristics of these groups dominate. To this end, any site with an attached EWG was automatically excluded from consideration as an oxidizable site. Furthermore, 1° sites are uniformly not oxidized under our conditions are and excluded. Using the 6-31G(d) basis set provided NPA partial charge data inconsistent with experimental observation.

Other measures of electronics at a C—H bond were also surveyed, for example Mulliken partial charges using the 6-31G(d) and 6-311++G(d,p) basis sets. Although Mulliken charges using 6-31G(d) provided qualitatively excellent correlation with the observed reactivity in all compounds, NPA charges provided a better fit to the data in the structure-based catalyst reactivity models (vide infra). Mulliken charges using the larger basis set provided poor correlation with experimental data. Finally, ESP and CHelpG electrostatic charges were explored, but these also did not qualitatively agree with experimental results.

SCF energies, enthalpies at 298K and Gibbs free energies at 298 K for optimized structures of complex substrates.

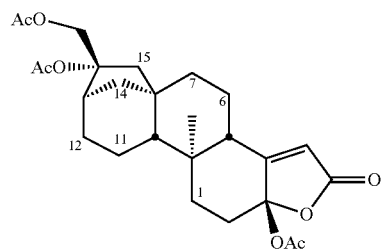

(−)-triacetoxy tricalysiolide B (19)

Total SCF energy: −1612.477147. Enthalpy at 298K: −1612.476203

Gibbs free energy at 298K: −1612.572465. Cartesian coordinates were also determined

TABLE 3.1

Calculated Partial Atomic Charges for (−)-Triacetoxy Tricalysiolide B (19).

| H Atom Number (NPA) | NPA Charge (B3LYP/6-311++G(d, p) | H Atom Number (Mulliken) | Mulliken Charge (B3LYP/6-31G(d)) |
|---|---|---|---|
| 11β | 0.195 | 9 | 0.115 |
| 6α | 0.196 | 7β | 0.134 |
| 7β | 0.197 | 7α | 0.136 |
| 12α | 0.200 | 13 | 0.137 |
| 9 | 0.201 | 11β | 0.139 |
| 11α | 0.206 | 5 | 0.140 |
| 1β | 0.207 | 12α | 0.140 |
| 7α | 0.208 | 6α | 0.142 |
| 1α | 0.211 | 15β | 0.142 |
| 14 | 0.212 | 11α | 0.143 |
| 6β | 0.213 | 14 | 0.144 |
| 15β | 0.213 | 1β | 0.146 |
| 12β | 0.215 | 1α | 0.146 |
| 2α | 0.216 | 6β | 0.153 |
| 5 | 0.220 | 12β | 0.153 |
| 13 | 0.223 | 2α | 0.162 |
| 2β | 0.229 | 2β | 0.167 |
| 15α | 0.240 | 15α | 0.182 |

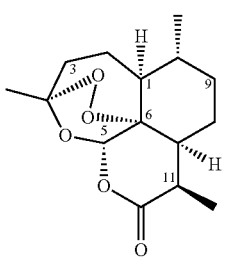

(+)-artemisinin (22)
Total SCF energy: −960.509858. Enthalpy at 298K: −960.508914
Gibbs free energy at 298K: −960.570049. Cartesian coordinates were also determined.

TABLE 3.2

Calculated Partial Atomic Charges for (+)-Artemisinin (22).

| H Atom Number (NPA) | NPA Charge (B3LYP/6-311++G(d, p)) | H Atom Number (Mulliken) | Mulliken Charge (B3LYP/6-31G(d)) |
|---|---|---|---|
| 10β | 0.186 | 10β | 0.126 |
| 5 | 0.187 | 1α | 0.133 |
| 9α | 0.193 | 9α | 0.133 |
| 8β | 0.195 | 9β | 0.139 |
| 2β | 0.204 | 7α | 0.141 |
| 9β | 0.206 | 8β | 0.144 |
| 1α | 0.210 | 2α | 0.146 |
| 2α | 0.212 | 3β | 0.146 |
| 3β | 0.213 | 2β | 0.151 |
| 8α | 0.216 | 8α | 0.153 |
| 7α | 0.216 | 5 | 0.153 |
| 3α | 0.224 | 3α | 0.167 |
| 11α | 0.253 | 11α | 0.196 |

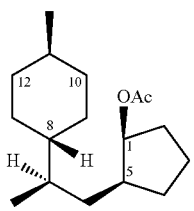 [SMILES: CC(=O)O[C@H]1CCC[C@H]1C[C@@H](C)[C@H]1CC[C@H](C)CC1]

(+)-(1S,2S)-2-((R)-2-((1r,4R)-4-methylcyclohexyl)propyl)cyclopentyl acetate (25)
Total SCF energy: −815.897675. Enthalpy at 298K: −815.896731
Gibbs free energy at 298K: −815.971968. Cartesian coordinates were also determined

TABLE 3.3

Calculated Partial Atomic Charges for (+)-Nectaryl Derivative (25).

| H Atom Number (NPA) | NPA Charge (B3LYP/6-311++G(d, p)) | H Atom Number (Mulliken) | Mulliken Charge (B3LYP/6-31G(d)) |
|---|---|---|---|
| 11α | 0.180 | 8β | 0.111 |
| 8β | 0.186 | 11α | 0.115 |
| 12β | 0.187 | 7α | 0.123 |
| 10β | 0.187 | 12β | 0.123 |
| 9α | 0.188 | 10β | 0.124 |
| 7α | 0.189 | 10α | 0.125 |
| 13α | 0.191 | 12α | 0.126 |
| 10α | 0.197 | 9β | 0.128 |
| 3α | 0.197 | 9α | 0.129 |
| 12α | 0.198 | 13β | 0.130 |
| 6β | 0.198 | 13α | 0.130 |
| 4β | 0.198 | 6β | 0.130 |
| 9β | 0.199 | 5α | 0.131 |
| 13β | 0.200 | 4α | 0.135 |
| 3β | 0.200 | 3α | 0.138 |
| 5α | 0.201 | 2β | 0.142 |
| 4α | 0.202 | 3β | 0.143 |
| 2β | 0.206 | 4β | 0.144 |
| 1α | 0.207 | 6α | 0.146 |
| 6α | 0.209 | 2α | 0.158 |
| 2α | 0.217 | 1α | 0.160 |

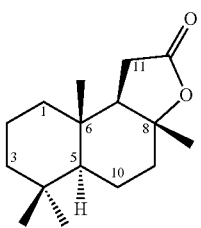

(+)-sclareolide (S12)
Total SCF energy: −775.413794. Enthalpy at 298K: −775.412850
Gibbs free energy at 298K: −775.471980. Cartesian coordinates were also determined

TABLE 3.4

Calculated Partial Atomic Charges for (+)-Sclareolide (S12).

| H Atom Number (NPA) | NPA Charge (B3LYP/6-311++G(d, p)) | H Atom Number (Mulliken) | Mulliken Charge (B3LYP/6-31G(d)) |
|---|---|---|---|
| 2β | 0.189 | 5α | 0.112 |
| 10β | 0.193 | 1α | 0.126 |
| 3α | 0.194 | 3α | 0.126 |
| 1α | 0.195 | 3β | 0.128 |
| 5α | 0.196 | 1β | 0.134 |
| 3β | 0.203 | 2β | 0.135 |
| 2α | 0.204 | 2α | 0.136 |
| 1β | 0.204 | 7α | 0.137 |
| 7α | 0.207 | 10β | 0.138 |
| 9α | 0.210 | 9β | 0.143 |
| 9β | 0.210 | 9α | 0.147 |
| 10α | 0.213 | 10α | 0.147 |
| 11β | 0.225 | 11β | 0.172 |
| 11α | 0.235 | 11α | 0.179 |

Parameterized Site Filter for Analysis of Substrate Reactivity.

To simplify the analysis of complex substrates with many possible sites of oxidation as well as provide a basis for further quantification of site-selectivity with Fe(PDP) (1) and Fe(CF$_3$-PDP) (2), a systematic procedure for assigning a value to all three reactivity factors (electronics, sterics and stereoelectronics) at a given site was developed.

Electronics: To assign an electronic parameter (E) to a particular site, we calculated the NPA partial charges (see "Computational Details" section above) for all hydrogen atoms in the molecule. Methyl groups and sites directly attached through heteroatoms to electron withdrawing groups were immediately excluded, given that no oxidation is observed at these sites. For methylene sites either: a) the average NPA charge of the two H-atoms was taken as E for that site if the molecule is conformationally flexible such that the hydrogens are on average nearly equivalent or b) the least hindered H-atom was selected. For example, on a cyclohexane, the less hindered equatorial H-atom was chosen. We consider this simplifying assumption to be valid considering the substantial difference in reactivity between axial and equatorial sites. It is very likely that some initial oxidation at a site does occur at the axial C—H bond; however, it is likely to be such a small percentage that it can be approximated as zero. Furthermore, 1° sites are uniformly not oxidized under our conditions and are excluded.

Sterics: To assign a steric value to a particular site we first considered that we needed to account both for the local steric hindrance around a site caused by substituents directly attached to that site as well as through space steric interactions caused by the conformation of the molecule.

Local Sterics: The most challenging issue was to parameterize the sizes of substituents attached to a site in a complex molecule. The sterics of simple groups, like Et, iPr, etc. have been well studied and parameterized using both empirical and computational methods ranging from Taft parameters, A-values, Charton values, Sterimol parameters, and interference values. Although the substituents at a site in complex molecules are all unique, we hypothesized that a reasonable approximation of the steric hindrance at a site could be obtained by generalizing all substituents: H, Me, OAc, C(O)Me, methylene carbons are approximated as Et, methine carbons as iPr, quaternary carbons as tBu. This approximation has the advantage of using a smaller set of parameters to represent the limitless variations in complex molecules as well as using groups that have already been well studied. While any of the previously defined steric parameters mentioned above provides a qualitative view of the relative sterics at a site, A-values provided the best fit for our. Each non-hydrogen substituent at a particular carbon (site) was approximated as one of the substituents listed above and assigned the corresponding A-value (scale adjusted such that H=1, Table 3.5). Although one hydrogen on a methylene site minimally hinders approach to the other, because this hydrogen could be oxidized to give product at that site, we do not count hydrogen substituents on the same site as causing steric hindrance.

Through Space Sterics: The need for a through space steric term is best exemplified by comparing cis- and trans-1,2-dimethylcyclohexane. The local steric parameter alone treats the tertiary sites in these molecules (C1) as equivalent as they are both attached to approximated substituents Me, Et, and iPr (2.74+2.79+3.21=8.7 steric parameter for both). However, the reactivity of these molecules is vastly different (cis favors 3° oxidation, trans slightly favors 2° oxidation. This phenomenon has long been recognized to arise from unfavorable interactions with the other axial hydrogens on the ring as the catalyst approaches in the trans-isomer. We therefore examined the geometry-optimized structure of any substrate under consideration and looked for 1,3-diaxial interactions or gauche/eclipsing butane-like interactions that would hinder the target hydrogen. The former were assigned the adjusted A-value for the group causing the 1,3-diaxial hindrance (Table 3.5) and the latter 0.9 and 2.2 corresponding to the conformational strain of those interactions. Although nearly all sites on a ring experience some 1,3-diaxial interactions with other hydrogens, if the ring site is a methylene, only the equatorial hydrogen is being evaluated and therefore 1,3-diaxial interactions that hinder the axial hydrogen are ignored. However, if the ring site is a methine with an axial C—H bond, that is the only C—H bond available for oxidation, all hindering 1,3-diaxial interactions must be considered.

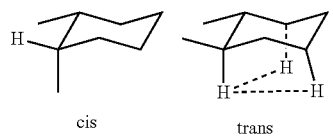

cis  trans

Both sites equivalent local sterics: Me, Et, iPr
trans hindered by other axial groups

TABLE 3.5

Adjusted A-Values (H = 1).

| Substituent | Adjusted A-Value |
|---|---|
| H | 1 |
| OAc | 1.78 |
| C(O)Me | 2.25 |
| Me | 2.74 |
| Et | 2.79 |
| iPr | 3.21 |
| tBu | 5.8 |

Stereoelectronics: Stereoelectronic effects can also have a strong impact on site selectivity. Although not examined in this report, hyperconjugative activation of neighboring C—H bonds by ethers and cyclopropane rings is generally so strong as to produce complete selectivity for the activated site.

A weaker form of activation takes the form of transition state strain relief. If a site has an axial group that experiences 1,3-diaxial strain with a large group, activation is possible. At the transition state for oxidation, the carbon becomes slightly planarized, relieving 1,3-diaxial strain slightly. Literature reports estimate that ~20% of the strain is relieved (Chen; Eschenmoser; Baran, *Angew. Chem. Int. Ed.* 2009, 48, 9705). Therefore, the A-value (unadjusted) for the group causing the strain is multiplied by 0.21 to obtain the stereoelectronic component. Since this is an activating effect, the stereoelectronic term is subtracted from the previously obtained steric term to arrive at a combined steric/stereoelectronic parameter (A). While we ignore axial hydrogens on methylene sites when assigning through space sterics because these hydrogens are significantly less prone to oxidation, 1,3-diaxial interactions with the axial hydrogen on a methylene site need to be considered for all sites because abstraction of the unhindered equatorial hydrogen causes planarization and relieves strain felt by the axial hydrogen.

The steric/stereoelectronic parameter (S)=Local+Through Space–Stereoelectronics.

An Example of Electronic, Steric and Stereoelectronic Analysis: (+)-Sclareolide. Assigning the Electronic Parameter (E) for Selected Sites in (+)-Sclareolide.

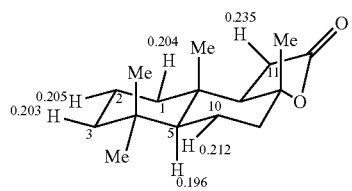

NPA charge = electronic parameter (E)

TABLE 3.6

Assigning Steric/Stereoelectronic Parameter (S) for Sites in (+)-Sclareolide (S12).

| Site ($H_{eq}$ atom) | Substituents Simplified Representation | Adjusted A-values | Through Space (value) | Stereoelectronic (value) | A |
|---|---|---|---|---|---|
| C1 | Et (C2 is a methylene), tBu (C6 is quaternary) | 2.79, 5.8 | gauche to C11 (0.9) | none (0) | 9.6 |
| C2 | Et, Et | 2.79, 2.79 | none (0) | 2Me C4, C6 (0.365) | 5.2 |
| C3 | Et, tBu | 2.79, 5.8 | none (0) | none (0) | 8.7 |
| C5 | Et, tBu, tBu | 2.79, 5.8, 5.8 | 4 axial H (2) | none (0) | 16.6 |
| C7 | Et, tBu, tBu | 2.79, 5.8, 5.8 | 2 axial H (1) | none (0) | 15.6 |
| C9 | Et, tBu | 2.79, 5.8 | none (0) | none (0) | 8.7 |
| C10 | Et, iPr | 2.79, 3.21 | 2 gauche to C4 methyls (1.8) | 2Me C6, C8 (0.365) | 7.4 |
| C11 | C(O)Me, iPr | 2.25, 3.21 | Gauche to C1 (0.9) | none (0) | 6.4 |

A = sum A-values + Through Space-Stereoelectronic guache butane-like interactions

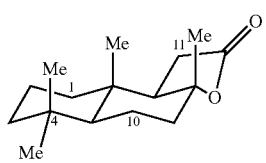

Through Space Hindrance in (+)-Sclareolide
1,3-diaxial strain

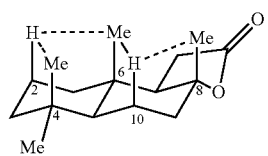

Stereoelectronic Activation in (+)-Sclareolide

Using the Parameterized Site Filter to Determine Reactive Sites within a Molecule. To simplify analysis of substrate properties, we developed a parameterized site filter to eliminate sites that are too electron poor or sterically hindered to be oxidized by catalyst 1 or 2. Using percent increases from the lowest value in the electronic and steric/stereoelectronic series, we define three regions: red=highly reactive, purple=moderately reactive, blue=unreactive. Only sites with two red or a red and a purple parameter are likely to be oxidized as all other sites are relatively unreactive. Table 3.7 depicts this process numerically for (+)-S12 and reveals that only sites C1, C2 and C3 are likely to be oxidized

TABLE 3.7

Parameterized Site Filter for Determining Likely Sites of Oxidation for (+)-Sclareolide (S12).

| Site ($H_{eq}$ atom) | Electronic Parameter (E) | Steric/Stereoelectronic Parameter (S) |
|---|---|---|
| 5 | 0.196 (red) | 16.6 (blue) |
| 3 | 0.203 (red) | 8.7 (purple) |
| 1 | 0.204 (red) | 9.6 (purple) |

TABLE 3.7-continued

Parameterized Site Filter for Determining Likely Sites of Oxidation for (+)-Sclareolide (S12).

| Site ($H_{eq}$ atom) | Electronic Parameter (E) | Steric/Stereoelectronic Parameter (S) |
|---|---|---|
| 2 | 0.205 (red) | 5.2 (red) |
| 7 | 0.207 (purple) | 15.6 (blue) |
| 9 | 0.210 (purple) | 8.6 (purple) |
| 10 | 0.212 (purple) | 7.4 (purple) |
| 11 | 0.235 (blue) | 6.4 (purple) |
| red lower limit | 0.196 (lowest E) | 5.2 (lowest S) |
| purple lower Limit | 0.206 = 0.196 + 5% | 7.3 = 5.2 + 40% |
| blue lower limit | 0.216 = 0.206 + 5% | 10.2 = 7.3 + 40% |

Creating Structure-Based Catalyst Reactivity Models: Having described the process for assigning electronic and steric/stereoelectronic parameters to each site in a molecule and using this information to identify likely sites of oxidation with a parameterized site filter, we sought to provide a quantitative model by which both the magnitude and direction of the site-selectivity could be predicted. This is an especially interesting question when comparing catalysts 1 and 2. Because the parameters E and S remain constant, these parameters must have different relative importance for each catalyst to produce the different site-selectivities we observe. To probe these questions we started with two assumptions:

1. the observed site-selectivity is determined kinetically, i.e. related to the $\Delta\Delta G^\ddagger$ between the two sites (a and b) in question and
2. $\Delta G^\ddagger$ is related to E and S at a given site.

Since we do not have the absolute $\Delta G^\ddagger$ for oxidation at a site, we considered that $\Delta\Delta G^\ddagger$ would be related to the difference between the E and S parameters ($\Delta E_{ab}$ and $\Delta S_{ab}$) of the two sites (a and b) as a function of catalyst such that $\Delta\Delta G^\ddagger = f_{cat}(\Delta E_{ab}, \Delta S_{ab})$. Because we have the E and S parameters for the sites as well as the observed $\Delta\Delta G^\ddagger$ from the experimentally measured site-selectivity, we can fit a curve to the data (Harper and Sigman, *Science* 2011, 333, 1875). The steps for constructing and utilizing our model are described below. See also FIG. 4.

Note that the model described herein may be implemented using a device comprising one or more processors and a non-transitory computer readable medium. For example, a non-transitory computer readable medium may include instructions stored thereon that when executed cause one or more processors to construct or utilize one or more of the models described herein. For example, computing device 100 described below with respect to FIG. 8A may be configured to construct a model described herein and/or may enable a user to predict reactivity of C—H bonds of a molecule toward oxidation using an embodiment of the model.

1. Assign the electronic (E) and steric/stereoelectronic (S) parameters at all sites in a molecule.

We selected a range of structurally varied compounds whose oxidation with Fe(PDP) (1) has been previously reported as well as the compounds reported herein with both catalyst 1 and 2. We then preformed the analyses described above to assign E and S at each site (see Table 3.6 for the results for (+)-S12 for example). These values provided a more concrete representation of the reactivity of each site, rather than more broad generalizations like, "3° C—H bonds are more electron rich." In (+)-S12, electronics are essentially equal, while C2 is preferred sterically; however, these are still mostly qualitative observations. Although they can be used to rationalize the outcome of a reaction, it would be difficult if not impossible to predict the site-selectivity a priori.

2. Use the E and S data to narrow down the potential sites of oxidation using the parameterized site filter. See process described above.

3. Normalize E and S.

We combined the E and S parameters for all substrates being used into a spreadsheet (25 molecules, ~140 sites). These values were normalized using the equation $P_n = (P - \mu)/\sigma$, where $P_n$ is the normalized parameter, P is the original parameter, $\mu$ is the mean of the parameters used and $\sigma$ is the standard deviation of the parameters used. Our data set represents a wide range of values likely to be encountered in many hydrocarbons which would be computationally time consuming for the reader to duplicate. Therefore, the mean and standard deviation values we used are provided so that the reader can obtain normalized values with a small data set of only one molecule: $\mu_E = 0.200533$, $\sigma_E = 0.013807$, $\mu_s = 7.839$, $\sigma_s = 2.712$. Steps 3 and 4 are most easily carried out using an excel spreadsheet which contains all the E and S values corresponding to each site. Using the cell equation functionality in excel, additional columns for normalized values can be created and calculated simultaneously. An example of the data output is shown in FIG. 8B.

4. Calculate $\Delta E_{ab}$ and $\Delta S_{ab}$ using the equation $\Delta E_{ab} = E_b - E_a$ where $E_b$ and $E_b$ are the normalized electronic parameters at site b and a respectively.

This step requires a reference site to be selected for calculating the a:b ratio and differences in E and S. Because the site-selectivities of the compounds being used to generate the model equation are known, a is selected as the major site for oxidation with Fe(PDP) (1). For example, C2 in (+)-sclareolide (S12) is the major site of oxidation so we calculate C2:C3 using $\Delta E_{2,3} = E_3 - E_2$ and C2:C1 using $\Delta E_{2,1} = E_1 - E_2$.

Figure 9:
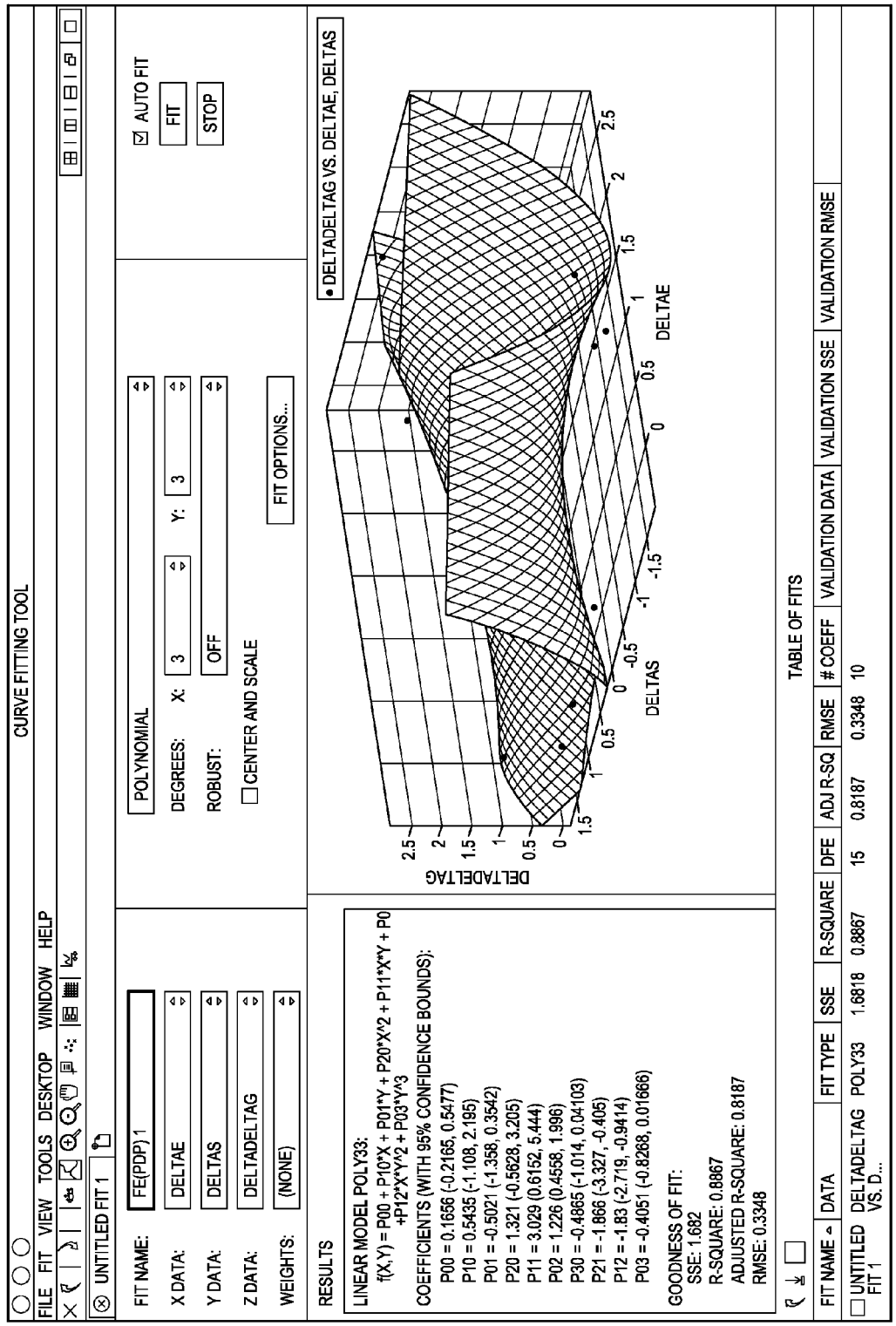
FIG. 9. Output of a curve fitting tool, as described by the methods of Example 3.

5. Import the data into Matlab (MATLAB version 7.14 (The MathWorks Inc., Natwick, M A, 2012)) and fit a curve, such as the curve illustrated in FIG. 9.

The data was fit to a third degree polynomial function using the curve-fitting tool. Where $X = \Delta E_{ab}$, $Y = \Delta S_{ab}$ and $Z = \Delta\Delta G^\ddagger$. We obtained the following two equations:

$$\Delta\Delta G_{PDP}^\ddagger = 0.4 + 0.0X - 0.8Y + 1.7X^2 + 3.5XY + 1.2Y^2 - 0.6X^3 - 2.1X^2Y - 1.8XY^2 - 0.4Y^3$$

$$\Delta\Delta G_{CF3\text{-}PDP}^\ddagger = 0.5 - 3.4X - 0.8Y + 5.9X^2 + 3.3XY + 1.0Y^2 + 0.1X^3 + 2.4X^2Y + 0.4XY^2 - 0.2Y^3$$

Notably we omitted two molecules (+)-nectaryl derivative (25) and (+)-(2S,4S)-methyl 2,4-dimethylhexanoate (3) which had not been oxidized previous to this report with one or both of the catalysts. These would provide a test of the predictive power of our model in the future.

6. Use the equation to calculate $\Delta\Delta G^\ddagger$

Figure 10:
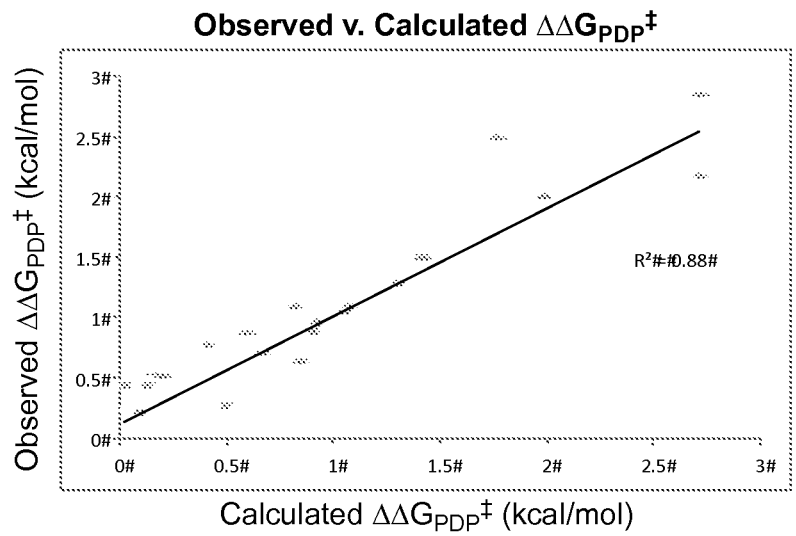
FIG. 10. Goodness of Fit plots of observed versus calculated $\Delta\Delta G^{\ddagger}$ for catalysts 1 and 2, demonstrating the goodness of the fit for the experimental data, as described in Example 3.
Figure 10:
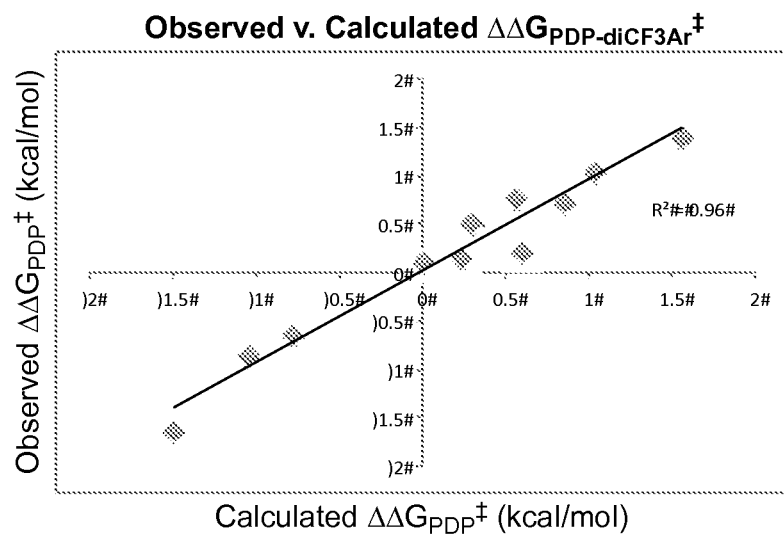

The E and S values for two sites can be normalized, the difference taken and $X = \Delta E_{ab}$ and $Y = \Delta S^{ab}$ input into the equation to obtain $\Delta\Delta G^\ddagger$ for either Fe(PDP) (1) or Fe(CF$_3$-PDP) (2). We consider a difference in observed versus calculated $\Delta\Delta G^\ddagger$ of 0.3 kcal/mol to be in good agreement while up to 0.5 kcal/mol is acceptable. The value 0.5 kcal/mol represents the difference between 1:1 and ~2:1 selectivity, meaning an equation predicting within this limit can differentiate between a non-selective (1.5:1 to 1:1), moderately selective (1.6:1 to 3:1) and selective reaction (>3:1). In practice, the differences are often much smaller. The plots of observed versus calculated $\Delta\Delta G^\ddagger$ for each catalyst demonstrate the goodness of the fit for the experimental data, as shown in FIG. 10.

In addition to providing a good fit for the data, these equations also predict the site selectivity for the two substrates omitted from the curve fitting process (+)-25 and (+)-3.

It should be noted that polynomial functions provide predictive power only in and around the region where data points have defined the curve. Because the curve is only defined for reactive sites, other sites on the molecule may not provide accurate predictions with these equations. For this reason, we only examine sites that are considered reactive using our parameterized site filter (see the Parameterized Site Filter for Analysis of Substrate Reactivity section above). We anticipate that as these catalysts continue to be used and site-selectivities reported, the equation can be further refined with the aid of additional data points to provide a wider predictive window.

Example 4

Catalyst-Controlled Oxidation of (+)-Sclareolide and Application of the Structure Based-Reactivity Models

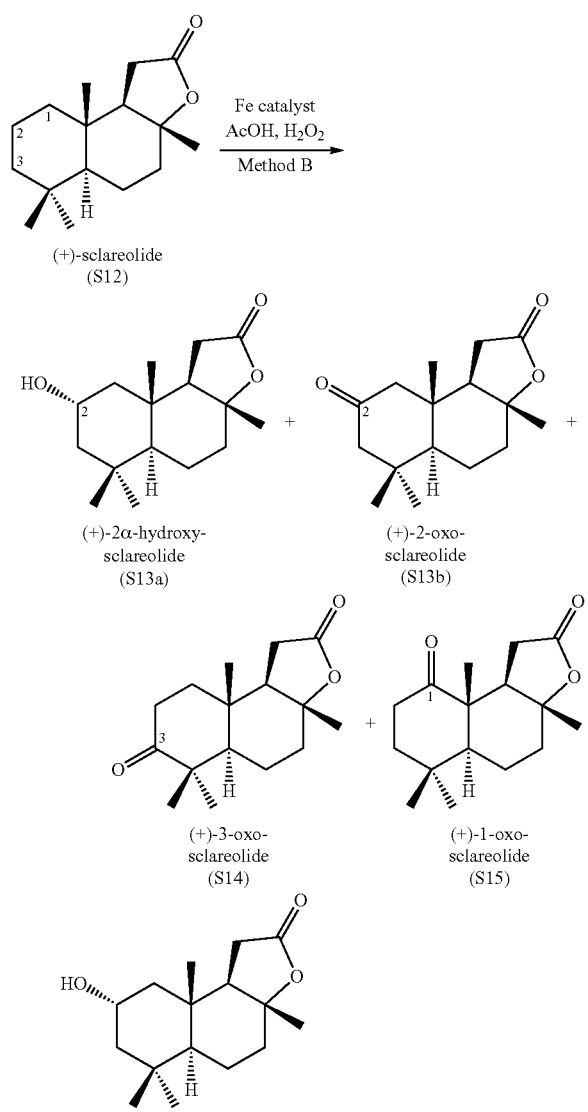

(+)-2α-hydroxy-sclareolide (S13a). (+)-sclareolide (S12) (75.1 mg, 0.3 mmol, 1.0 equiv) in MeCN (1.5 mL) was reacted with (R,R)—Fe(CF$_3$-PDP) (2) according to Method B. Purification by flash chromatography on silica (~75 mL) eluting with gradient 10→20→30% acetone/hexane. Reported ratios are of isolated material. Overlapping peaks in the crude $^1$H NMR and GC made accurate C2:C3 ratio determination impossible so isolated ratios are reported. Run 1: recycled one time for a total of 32% (+)-S13a, 20% (+)-S13b, 20% (+)-S14, 10% (+)-S15, 9% RSM, 2.6:1 C2:C3 oxidation, 52% total C2 oxidation; cycle 1 (+)-S13a (20.8 mg, 0.078 mmol, 26%), (+)-S13b (13.1 mg, 0.05 mmol, 17%), (+)-S14 (13.1 mg, 0.05 mmol, 17%), (+)-S15 (7.3 mg, 0.028 mmol, 10%), RSM (15.9 mg, 0.064 mmol, 21%); cycle 2 (+)-S13a (4.5 mg, 0.017 mmol, 28%), (+)-S13b (2.7 mg, 0.01 mmol, 16%), (+)-S14 (2.7 mg, 0.01 mmol, 16%), (+)-S15 trace, RSM (6.5 mg, 0.026 mmol, 41%). Run 2: recycled one time for a total of 32% (+)-S13a, 24% (+)-S13b, 24% (+)-S14, 9% (+)-S15, 6% RSM, 2.3:1 C2:C3 oxidation; cycle 1 (+)-S13a (24.0 mg, 0.09 mmol, 30%), (+)-S13b (13.9 mg, 0.05 mmol, 18%), (+)-S14 (13.9 mg, 0.05 mmol, 17%), (+)-S15 (7.2 mg, 0.03 mmol, 9%), RSM (23.7 mg, 0.09 mmol, 32%); cycle 2 (+)-S13a (5.3 mg, 0.021 mmol, 27%), (+)-S13b (2.8 mg, 0.012 mmol, 15%), (+)-S14 (2.8 mg, 0.012 mmol, 15%), (+)-S15 trace, RSM (4.5 mg, 0.018 mmol, 23%). Run 3: recycled one time for a total of 36% (+)-S13a, 21% (+)-S13b, 21% (+)-S14, 8% (+)-S15, 7% RSM, 2.7:1 C2:C3 oxidation; cycle 1 (+)-S13a (23.4 mg, 0.088 mmol, 29%), (+)-S13b (13.6 mg, 0.05 mmol, 17%), (+)-S14 (13.6 mg, 0.05 mmol, 17%), (+)-S15 (6.3 mg, 0.024 mmol, 8%), RSM (18.8 mg, 0.075 mmol, 25%); cycle 2 (+)-S13a (5.2 mg, 0.02 mmol, 25%), (+)-S13b (3.3 mg, 0.013 mmol, 17%), (+)-S14 (3.3 mg, 0.013 mmol, 17%), (+)-S15 trace, RSM (5.7 mg, 0.023 mmol, 30%). Average overall yield (+)-S13a: 33±2%. Average overall yield (+)-S13b: 22±2% Average overall yield C2 oxidation: 55±4%. Average overall yield (+)-S14: 22±2%. Average overall yield (+)-S15: 9±1%. Average overall RSM: 7±2%. Average ratio C2:C3 oxidation: 2.6:1±0.2. $^1$H NMR (500 MHz, CDCl$_3$) δ 3.96 (m, 1H), 2.42 (app t, J=15.5 Hz, 1H), 2.24 (dd, J=16.5, 6.5 Hz, 1H), 2.07 (d, J=12.0 Hz, 1H), 1.99 (dd, J=15.0, 6.5 Hz, 1H), 1.89 (dd, J=14.0, 3.0 Hz, 1H), 1.84-1.76 (m, 2H), 1.68 (td, J=12.5, 3.5 Hz, 1H), 1.40-1.32 (m, 1H), 1.31 (s, 3H), 1.14 (t, J=12.0 Hz, 1H), 1.07 (dd, J=12.5, 1.5 Hz, 1H), 0.96 (t, J=12.5 Hz, 1H), 0.94 (s, 6H), 0.89 (s, 3H); $^{13}$C NMR (125 MHz, CDCl$_3$) δ 176.4, 86.1, 64.2, 58.8, 56.1, 51.3, 48.3, 38.4, 37.3, 34.7, 33.2, 28.7, 21.7, 21.6, 20.1, 16.1; IR (film): 3396, 2947, 2872, 1770, 1460, 1389, 1367, 1281, 1227, 1196, 1178, 1120, 1036 cm$^{-1}$; HRMS (ESI) m/z calc'd for C$_{16}$H$_{27}$O$_3$ [M+H]$^+$: 267.1960, found 267.1966; [α]$_D^{23}$=+27.8° (c=0.5, CHCl$_3$).

The site of oxidation was confirmed by oxidizing (+)-2α-hydroxy-sclareolide (S13a) to (+)-S13b using DMP and matching the spectral data to those reported in the literature (*Science* 2010, 327, 566). The stereochemistry of the 2° alcohol was assigned based on a combination of $^1$H NMR, $^1$H-$^1$H TOCSY and NOESY1D NMR methods. The axial proton at C2 shows NOE correlations with the two axial methyl groups on the A-ring as well as the two adjacent equatorial protons on the A-ring at the C1 and C3 positions.

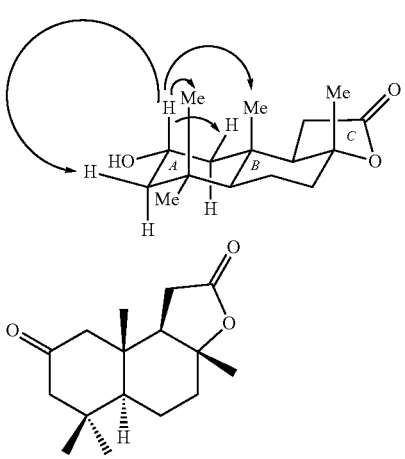

(+)-2-oxo-sclareolide (S13b). $^1$H NMR (500 MHz, CDCl$_3$) δ 2.45 (dd, J=14.5, 12.5 Hz, 1H), 2.34-2.14 (m, 7H), 2.03 (app dq, J=14.5, 2.3 Hz, 1H), 1.80 (td, J=12.5, 4.0 Hz, 1H), 1.69 (dd, J=12.5, 3.0 Hz, 1H), 1.49 (qd, J=13.0, 3.5 Hz, 1H), 1.35 (s, 3H), 1.09 (s, 3H), 0.93 (s, 6H); HRMS (ESI) m/z calc'd for $C_{16}H_{25}O_3$ [M+H]$^+$: 265.1804, found 265.1804. These spectral data match those reported in the literature (*Science* 2010, 327, 566).

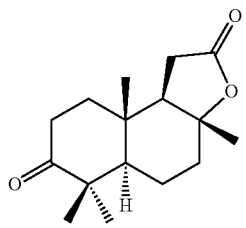

(+)-3-oxo-sclareolide (S14). $^1$H NMR (500 MHz, CDCl$_3$) δ 2.62-2.55 (m, 1H), 2.52-2.46 (m, 1H), 2.48 (dd, J=16.5, 14.5 Hz, 1H), 2.29 (dd, J=16.0, 6.5 Hz, 1H), 2.13 (dt, J=11.5, 3.0 Hz, 1H), 2.00 (dd, J=14.5, 6.5 Hz, 1H), 1.87-1.82 (m, 1H), 1.77-1.70 (m, 2H), 1.63-1.53 (m, 3H), 1.39 (s, 3H), 1.13 (s, 3H), 1.06 (s, 3H), 1.03 (s, 3H); HRMS (ESI) m/z calc'd for $C_{16}H_{25}O_3$ [M+H]$^+$: 265.1804, found 265.1805. These spectral data match those reported in the literature (*Science* 2010, 327, 566).

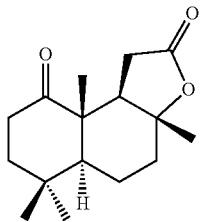

(+)-1-oxo-sclareolide (S15). $^1$H NMR (500 MHz, CDCl$_3$) δ 2.96 (dd, J=16.5, 6.5 Hz, 1H), 2.67 (ddd, J=14.5, 9.5, 5.0 Hz, 1H), 2.53 (dd, J=17.0, 14.0 Hz, 1H), 2.32-2.24 (m, 1H), 2.15 (dd, J=14.0, 6.5 Hz, 1H), 2.08 (dt, J=11.5, 3.5 Hz, 1H), 1.92-1.80 (m, 2H), 1.70-1.48 (m, 4H), 1.34 (s, 3H), 1.19 (s, 3H), 1.05 (s, 3H), 1.01 (s, 3H); HRMS (ESI) m/z calc'd for $C_{16}H_{25}O_3$ [M+H]$^+$: 265.1804, found 265.1807. These spectral data match those reported in the literature (Cano et al., *J Braz. Chem. Soc.* 2011, 22, 1177).

Oxidation with (S,S)—Fe(CF$_3$-PDP) (2) according to Method B. Run 1: (+)-S13a (11.5 mg, 0.043 mmol, 14%), (+)-S13b (17.5 mg, 0.066 mmol, 22%), (+)-S14 (24.6 mg, 0.09 mmol, 31%), (+)-S15 (5.5 mg, 0.012 mmol, 4%), RSM (11.9 mg, 0.043 mmol, 14%), 1.2:1 C2:C3 oxidation. Run 2: (+)-S13a (14.3 mg, 0.054 mmol, 18%), (+)-S13b (18.6 mg, 0.07 mmol, 23%), (+)-S14 (26.0 mg, 0.1 mmol, 33%), (+)-S15 (6.7 mg, 0.025 mmol, 8%), RSM (10.1 mg, 0.04 mmol, 13%), 1.2:1 C2:C3 oxidation. Average yield (+)-S13a: 16%. Average yield S13b: 23%. Average yield C2 oxidation: 39%. Average yield (+)-S14: 32%. Average RSM: 14%. Average ratio C2:3 oxidation: 1.2:1.

Example 5

Oxidation of Triacetoxy Tricalysiolide B

Data for the substrate controlled and catalyst controlled oxidation of triacetoxy tricalysiolide B, and its corresponding structure-based reactivity data, are shown in FIG. 5.

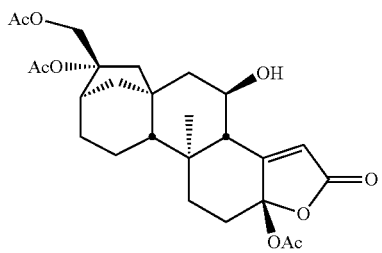

(−)-6β-hydroxy-triacetoxy tricalysiolide B (20). Triacetoxy tricalysiolide B (19) (71.2 mg, 0.15 mmol, 1.0 equiv) in MeCN (2 mL) was reacted with (R,R)—Fe(CF$_3$-PDP) (2) according to Method A. Purification by flash chromatography on silica (~75 mL) eluting with gradient 30→40% acetone/hexane. Residual iron catalyst could not be removed from the crude reaction mixture without either losing oxidized products, broadening the $^1$H NMR spectrum or running a standard flash column. Therefore, isolated ratios are reported. Run 1: recycled one time for a total of 62% (−)-20, >5% (−)-21, 15% RSM, >10:1 C6:C7; cycle 1 (−)-20 (33.2 mg, 0.068 mmol, 45%), (−)-21 (3.1 mg, 0.006 mmol, 4%), RSM (30.2 mg, 0.064 mmol, 42%); cycle 2 (−)-20 (12.3 mg, 0.025 mmol, 38%), (−)-21 (<1 mg, <5%), RSM (12.1 mg, 0.026 mmol, 41%). Run 2: recycled one time for a total of 59% (−)-20, <5 (−)-21, 17% RSM, >10:1 C6:C7; cycle 1 (−)-20 (30.5 mg, 0.062 mmol, 42%), (−)-21 (2.3 mg, 0.005 mmol, 3%), RSM (33.1 mg, 0.07 mmol, 47%); cycle 2 (−)-20 (13.1 mg, 0.027 mmol, 38%), (−)-21 (<1 mg, <5%), RSM (11.9 mg, 0.025 mmol, 36%). Run 3: recycled one time for a total of 63% yield (−)-20, 5% (−)-21, 18% RSM, >10:1

TABLE 4.1

Catalyst Comparison for the Oxidation of (+)-Sclareolide (S12).

| Catalyst | % isolated yield (+)-S13a | % isolated yield (+)-S13b | % isolated yield C2 oxidation | % isolated yield (+)-S14 | % isolated yield (+)-S15 | % isolated yield RSM | C2:C3$^a$ |
|---|---|---|---|---|---|---|---|
| (R,R)—Fe(PDP) (1) | — | 46 | 46 | 33 | 8 | 9 | 1.4:1 |
| (S,S)—Fe(PDP) (1) | — | 26 | 26 | 25 | 9 | 9 | 1:1 |
| (R,R)—Fe(CF$_3$-PDP) (2)$^b$ | 33$^c$ | 22 | 55 | 22 | 9 | 7 | 3:1 |
| (S,S)—Fe(CF$_3$-PDP) (2)$^b$ | 16$^d$ | 23 | 39 | 32 | 6 | 14 | 1.2:1 |

$^a$Isolated ratio.
$^b$Starting material was recycled 1 time.
$^c$Average of 3 runs at 0.3 mmol.
$^d$Average of 2 runs at 0.3 mmol.

C6:C7; cycle 1 (−)-20 (33.4 mg, 0.068 mmol, 45%), (−)-21 (3.6 mg, 0.008 mmol, 5%), RSM (30.9 mg, 0.065 mmol, 43%); cycle 2 (−)-20 (13.1 mg, 0.027 mmol, 41%), (−)-21 (<1 mg, <5%), RSM (12.7 mg, 0.027 mmol, 41%). Average overall yield (−)-20: 61±3%. Average overall yield (−)-21: <5%. Overall RSM: 16±2%. Average ratio C6:C7 oxidation: >10:1. $^1$H NMR (500 MHz, CDCl$_3$) δ 6.00 (s, 1H), 4.70 (ABq, J=12.5 Hz, Δv$_{AB}$=258.5 Hz, 2H), 3.95 (td, J=10.5, 4.0 Hz, 1H), 2.63-2.61 (m, 1H), 2.56 (br s, 1H), 2.10-2.05 (m, 1H), 2.08 (s, 3H), 2.07 (s, 3H), 2.01 (s, 3H), 1.96-1.90 (m, 2H), 1.86-1.72 (m, 3H), 1.70-1.46 (m, 7H), 1.32 (d, J=7.5 Hz, 1H), 1.30-1.21 (m, 2H), 0.90 (s, 3H); HRMS (ESI) m/z calc'd for C$_{26}$H$_{35}$O$_9$ [M+H]$^+$: 491.2281, found 491.2278. These spectral data match those reported in the literature (Bigi et al., *Synlett* 2012, 23, 2768).

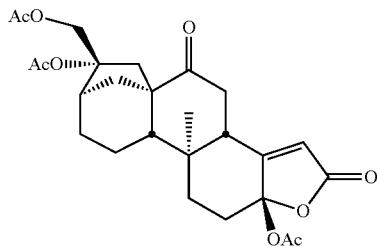

(−)-7oxo-triacetoxy tricalysiolide B (21). $^1$H NMR (CDCl$_3$, 500 MHz): δ 5.80 (s, 1H), 4.96 (d, J=12.0 Hz, 1H), 4.49 (d, J=12.5 Hz, 1H), 3.17 (d, J=15.5 Hz, 1H), 2.77-2.67 (m, 3H), 2.60-2.53 (m, 2H), 2.10-2.05 (m, 1H), 2.08 (s, 3H), 2.07 (s, 3H), 2.01 (s, 3H), 1.95-1.90 (m, 1H), 1.85-1.65 (m, 7H), 1.65-1.60 (m, 1H), 1.32 (td, J=14.5, 4.0 Hz, 1H), 1.04 (s, 3H); HRMS (ESI) m/z calc'd for C$_{26}$H$_{33}$O$_9$ [M+H]$^+$: 489.2125, found 489.2124. These spectral data match those reported in the literature (Bigi et al., *Synlett* 2012, 23, 2768).

TABLE 5.1

Catalyst Comparison for the Oxidation of (−)-Triacetoxy Tricalysiolide B (19).

| Catalyst | % isolated yield (−)-20 | % isolated yield (−)-21 | % isolated yield RSM | C6:C7[b] |
|---|---|---|---|---|
| (S,S)-Fe(PDP) (1)[c] | 31 | 12 | 10 | 3:1 |
| (R,R)-Fe(PDP) (1)[c] | 27 | 19 | 8 | 1.4:1 |
| (R,R)-Fe(CF$_3$-PDP) (2)[c] | 61 | <5 | 17 | >10:1 |
| (S,S)-Fe(CF$_3$-PDP) (2)[c,d] | 40 | <5 | 37 | 8:1 |

[a]Average of 3 runs at 0.15 mmol.
[b]Isolated ratio.
[c]Starting material was recycled 1 time.
[d]Average of 2 runs at 0.15 mmol.

Oxidation with (R,R)—Fe(PDP) (1) according to Method A. Run 1: recycled 1 time for a total of 21% (−)-20, 16% (−)-21, 10% RSM, 1.3:1 C6:C7 oxidation; cycle 1 (−)-20 (14.2 mg, 0.029 mmol, 19%), (−)-21 (11.9 mg, 0.024 mmol, 16%), RSM (23.8 mg, 0.05 mmol, 33%); cycle 2 (−)-20 (5.4 mg, 0.011 mmol, 22%), (−)-21 (3.7 mg, 0.008 mmol, 15%), RSM (7.1 mg, 0.015 mmol, 30%). Run 2: recycled 1 time for a total of 30% (−)-20, 19% (−)-21, 9% RSM, 1.6:1 C6:C7 oxidation; cycle 1 (−)-20 (18.1 mg, 0.037 mmol, 24%), (−)-21 (11.0 mg, 0.023 mmol, 15%), RSM (19.7 mg, 0.042 mmol, 28%); cycle 2 (−)-20 (3.7 mg, 0.008 mmol, 18%), (−)-21 (2.7 mg, 0.005 mmol, 13%), RSM (6.4 mg, 0.013 mmol, 32%). Run 3: recycled 1 time for a total of 29% (−)-20, 23% (−)-21, 8% RSM, 1.3:1 C6:C7 oxidation; cycle 1 (−)-20 (17.0 mg, 0.035 mmol, 23%), (−)-21 (13.3 mg, 0.027 mmol, 18%), RSM (19.2 mg, 0.04 mmol, 27%); cycle 2 (−)-20 (3.8 mg, 0.008 mmol, 19%), (−)-21 (3.2 mg, 0.007 mmol, 16%), RSM (5.7 mg, 0.012 mmol, 30%). Average overall yield (−)-20: 27±5%. Average overall yield (−)-21: 19±4%. Average overall RSM: 9±1%. Average ratio C6:C7 oxidation: 1.4±0.2:1. Note: When the reaction is run with (R,R)-1 the C7 ketone is isolated as an inseparable mixture with another ketone. Based on the structure-based catalyst reactivity model, it is very likely that this is the C11 ketone; however, this structure could not be unambiguously assigned by X-ray crystallographic or $^1$H NMR analysis in contrast to the C7 ketone. This highlights the advantage of using more (R,R)-2.

Oxidation with (S,S)—Fe(CF$_3$-PDP) (2) according to Method A. Run 1: recycled 1 time for a total of 42% (−)-20, 6% (−)-21, 39% RSM, 7:1 C6:C7 oxidation, cycle 1 (−)-20 (18.7 mg, 0.038 mmol, 25%), (−)-21 (2.5 mg, 0.005 mmol, 3%), RSM (43.6 mg, 0.092 mmol, 61%); cycle 2 (−)-20 (12.2 mg, 0.025 mmol, 27%), (−)-21 (1.8 mg, 0.004 mmol, 4%), RSM (27.9 mg, 0.059 mmol, 64%). Run 2: recycled 1 time for a total of 38% (−)-20, 4% (−)-21, 36% RSM, 10:1 C6:C7 oxidation; cycle 1 (−)-20 (17.2 mg, 0.035 mmol, 23%), (−)-21 (2.2 mg, 0.004 mmol, 3%), RSM (42.2 mg, 0.089 mmol, 60%); cycle 2 (−)-20 (10.9 mg, 0.022 mmol, 25%), (−)-21 (0.9 mg, 0.002 mmol, 2%), RSM (25.8 mg, 0.054 mmol, 61%). Average overall yield (−)-20: 40%. Average overall yield (−)-21: <5%. Average overall RSM: 37%. Average ratio C6:C7 oxidation: 8:1.

Example 6

Oxidation of (+)-Artemisinin

Data for the substrate controlled and catalyst controlled oxidation of (+)-Artemisinin, and its corresponding structure-based reactivity data, are shown in FIG. 6.

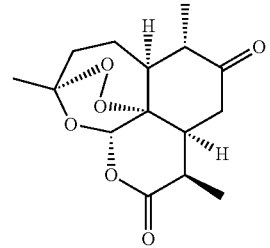 [SMILES: C[C@@H]1C(=O)C[C@H]2[C@@H](C)C(=O)O[C@@H]3O[C@@]4(C)CC[C@@H]1[C@]32OO4]

(+)-9-oxo-artemisinin (23). (+)-Artemisinin (22) (141.1 mg, 0.5 mmol, 1.0 equiv) in MeCN (2.25 mL) was reacted with (S,S)—Fe(CF$_3$-PDP) (3) according to Method A but using reduced loading of AcOH (2.9 µmL, 3.0 mg, 0.05 mmol, 0.1 equiv). Purification was carried out by flash chromatography on silica (~125 mL) eluting with 10→30% EtOAc/hexane. Run 1: recycled five times for a total of 52% (+)-23, <5% (+)-24, 7% RSM, 9:1 crude 2°:3° by $^1$H NMR; cycle 1 (+)-23 (60.1 mg, 0.2 mmol, 20%), (+)-24 (3.9 mg, 0.013 mmol, 1%), RSM (194.7 mg, 0.69 mmol, 69%); cycle 2 (+)-23 (38.8 mg, 0.13 mmol, 19%), RSM (130.4 mg, 0.46 mmol, 67%); cycle 3 (+)-23 (26.2 mg, 0.088 mmol, 19%), RSM (86.9 mg, 0.31 mmol, 67%); cycle 4 (+)-23 (15.4 mg, 0.052 mmol, 17%), RSM (56.8 mg, 0.2 mmol, 65%); cycle 5 (+)-23 (9.1 mg, 0.031 mmol, 15%), RSM (34.5 mg, 0.12 mmol, 61%); cycle 6 (+)-23 (6.0 mg, 0.02 mmol, 17%), RSM (20.7 mg, 0.073 mmol, 61%). Run 2: recycled five times for a total of 52% yield (+)-23<5% (+)-24, 8% RSM, 12:1 crude 2°:3° by $^1$H NMR; cycle 1 (+)-23 (57.5 mg, 0.19 mmol, 19%), (+)-24 (3.8 mg, 0.013 mmol, 1%), RSM (192.8 mg, 0.68 mmol, 68%); cycle 2 (+)-23 (34.3 mg, 0.12 mmol, 17%), RSM (134.3 mg, 0.48 mmol, 70%); cycle 3 (+)-23 (28.4 mg, 0.096 mmol, 20%), RSM (88.1 mg, 0.31 mmol, 65%); cycle 4 (+)-23 (15.6 mg, 0.053 mmol, 17%), RSM (59.5 mg, 0.21 mmol, 68%); cycle 5 (+)-23 (11.3 mg, 0.038 mmol, 18%), RSM (37.3 mg, 0.13 mmol, 63%); cycle 6 (+)-23 (5.8 mg, 0.02 mmol, 17%), RSM (22.7 mg, 0.073 mmol, 61%). Run 3: recycled five times for a total of 49% (+)-23, <5% (+)-24, 9% RSM, 12:1 crude 2°:3° by $^1$H NMR; cycle 1 (+)-23 (53.3 mg, 0.18 mmol, 18%), (+)-24 (5.1 mg, 0.017 mmol, 2%), RSM (186.3 mg, 0.66 mmol, 66%); cycle 2 (+)-23 (39.8 mg, 0.13 mmol, 20%), RSM (128.9 mg, 0.46 mmol, 69%); cycle 3 (+)-23 (23.6 mg, 0.08 mmol, 17%), RSM (84.5 mg, 0.30 mmol, 65%); cycle 4 (+)-23 (15.2 mg, 0.051 mmol, 17%), RSM (60.2 mg, 0.21 mmol, 70%); cycle 5 (+)-23 (9.6 mg, 0.032 mmol, 15%), RSM (36.9 mg, 0.13 mmol, 62%); cycle 6 (+)-23 (7.4 mg, 0.025 mmol, 19%), RSM (25.3 mg, 0.09 mmol, 69%). Average overall yield (+)-23: 51±2%. Average overall yield (+)-24: <5%. Average overall RSM: 8±1%. Average ratio 2°:3° oxidation: 11:1. $^1$H NMR (500 MHz, CDCl$_3$) δ 6.20 (s, 1H), 3.47-3.38 (m, 1H), 2.62 (d, J=9.5 Hz, 1H), 2.54-2.46 (m, 1H), 2.32 (app sextet, J=6.5 Hz, 1H), 2.22-2.12 (m, 3H), 2.10-2.03 (m, 1H), 1.83 (td, J=11.0, 7.0 Hz, 1H), 1.72-1.62 (m, 1H), 1.50 (s, 3H), 1.22 (d, J=7.5 Hz, 3H), 1.34 (d, J=6.5 Hz, 3H); HRMS (ESI) m/z calc'd for $C_{15}H_{21}O_6$ [M+H]$^+$: 297.1338, found 297.1346; [α]$_D^{23}$=+58.3° (c=0.6, CHCl$_3$). These spectral data match those reported in the literature (Liu et al., *Bioorg. Med. Chem. Lett.* 2006, 16, 1909).

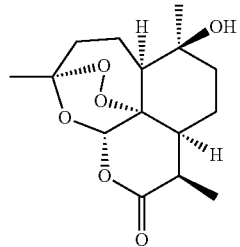 [SMILES: C[C@H]1C(=O)O[C@@H]2O[C@@]3(C)CC[C@@H]4[C@@]2(OO3)[C@H]1CC[C@]4(C)O]

(+)-10β-hydroxy-arteminin (24). $^1$H NMR (500 MHz, CDCl$_3$) δ 6.48 (s, 1H), 3.35 (dq, J=7.0, 5.5 Hz, 1H), 2.44 (ddd, J=14.5, 13.5, 4.5 Hz, 1H), 2.10 (m, 1H), 2.01 (m, 1H), 1.86-1.72 (m, 4H), 1.66 (dd, J=11.5, 7.0 Hz, 1H), 1.49-1.47 (m, 2H), 1.45 (s, 3H), 1.30 (s, 3H), 1.22 (d, J=7.0 Hz, 3H); HRMS (ESI) m/z calc'd for $C_{15}H_{23}O_6$ [M+H]$^+$: 299.1495, found 299.1496. These spectral data match those reported in the literature (*Science* 2007, 318, 783).

TABLE 6.1

Catalyst Comparison for the Oxidation of (+)-Artemisinin (22).

| Catalyst | % isolated yield (+)-23 | % isolated yield (+)-24 | % isolated yield RSM | 2°:3°[a] |
|---|---|---|---|---|
| (S,S)-Fe(PDP) (1)[b] | 23 | 54 | 8 | 1:2.3 |
| (R,R)-Fe(PDP) (1)[b] | 10 | 14 | 74 | 1:1.4 |
| (S,S)-Fe(CF$_3$-PDP) (3)[c] | 52[d] | <5 | 8 | 11:1 |
| (R,R)-Fe(CF$_3$-PDP) (3) | 11[e] | trace | 65 | 9:1 |

[a]Crude ratio determined by $^1$H NMR.
[b]Starting material was recycled 2 times.
[c]Starting material was recycled 5 times.
[d]Average of 3 runs at 1.0 mmol.
[e]Average of 2 runs at 0.5 mmol.

Oxidation with (R,R)—Fe(CF$_3$-PDP) (2) according to Method A but using reduced loading of AcOH (2.9 μL, 3.0 mg, 0.05 mmol, 0.1 equiv). Purification by flash chromatography on silica (~75 mL) eluting with 10→30% EtOAc/hexane. Run 1: (+)-23 (14.8 mg, 0.05 mmol, 10%), RSM (93.1 mg, 0.33 mmol, 66%). Run 2: (+)-23 (15.1 mg, 0.051 mmol, 11%), RSM (90.5 mg, 0.32 mmol, 64%). Average yield (+)-23: 11%. Average RSM: 65%.

Example 7

Oxidation of a Nectaryl Derivative

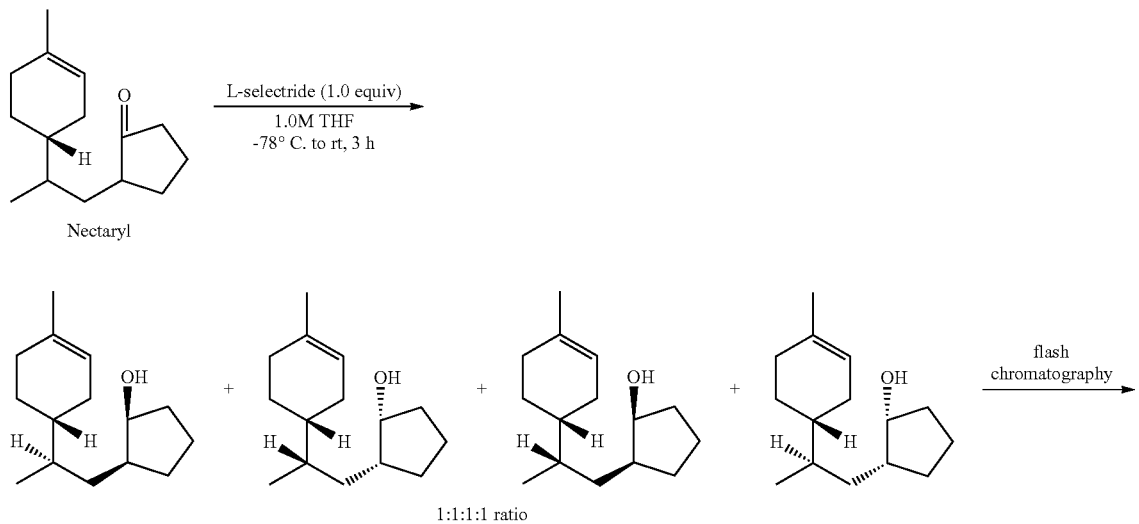

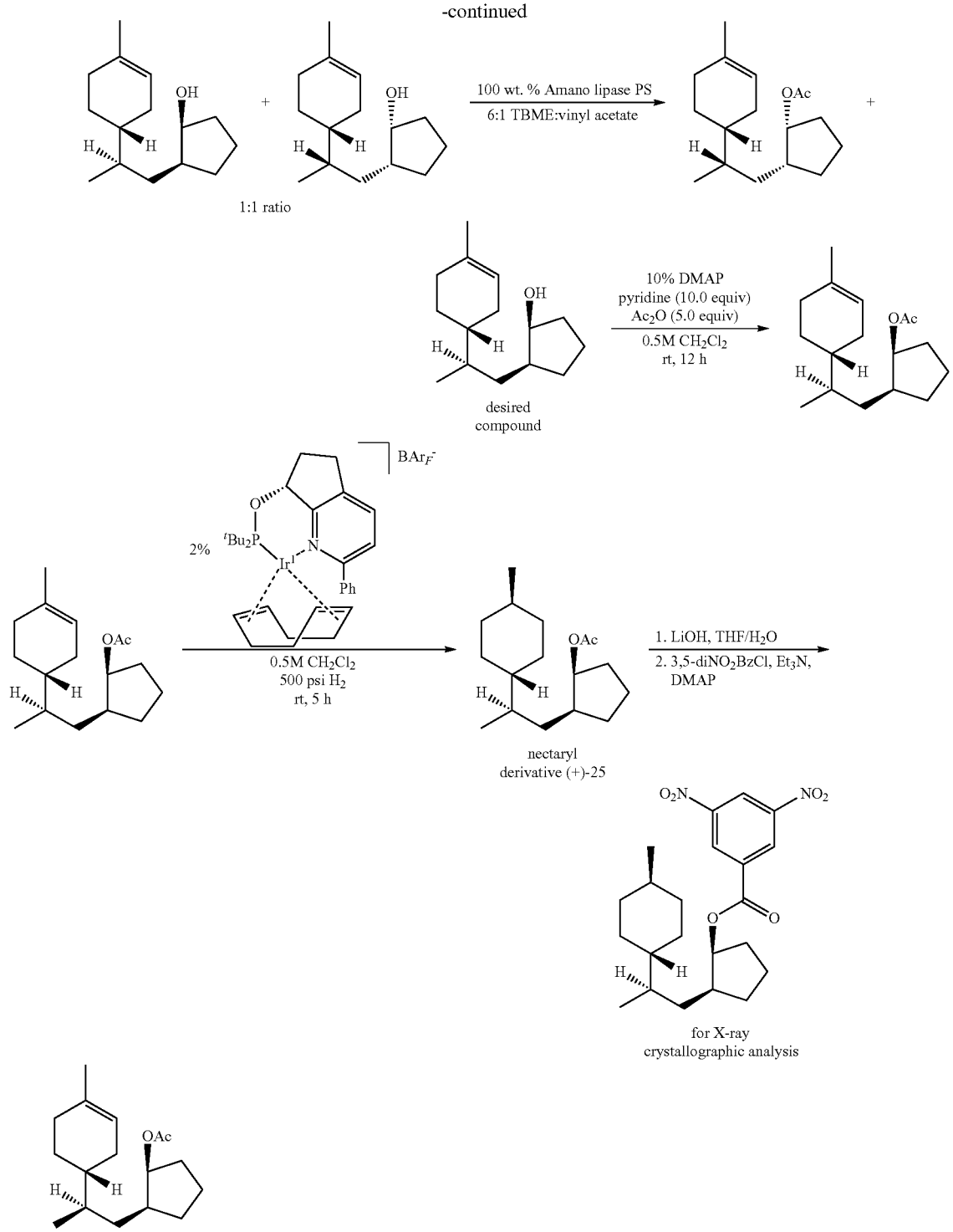

(+)-(1S,2S)-2-((R)-2-((R)-4-methylcyclohex-3-en-1-yl)propyl)cyclopentyl acetate. No precautions were taken to avoid air or moisture. (+)-(1S,2S)-2-((R)-2-((R)-4-methylcyclohex-3-en-1-yl)propyl)cyclopentanol (2.37 g, 10.6 mmol, 1.0 equiv, prepared according to the procedure of Gatti (Tetrahedron: Asymmetry 2008, 19, 800) was dissolved in $CH_2Cl_2$ (20 mL, 0.5 M) in a 100 mL round bottomed flask containing a stir bar. Pyridine (8.6 mL, 8.38 g, 106.0 mmol, 10.0 equiv, Sigma-Aldrich), acetic anhydride (5 mL, 5.41 g, 53.0 mmol, 5.0 equiv, Fisher Scientific) and 4-dimethylaminopyridine (DMAP, 130 mg, 1.1 mmol, 10 mol %, Sigma-Aldrich) were added and the reaction was stirred 12 h at room temperature. The reaction was quenched with saturated aqueous $NaHCO_3$. The layers were separated and the organic layer was washed with 3M HCl(1×10 mL). The organic layer was dried ($MgSO_4$), filtered and concentrated. Purification by flash chromatography on silica (~250 mL) eluting with 5% EtOAc/hexanes afforded the title compound in quantitative yield (2.79 g, 10.5 mmol) as a colorless oil. $^1$H NMR (500 MHz, CDCl$_3$) δ 5.35 (br s, 1H), 5.14 (t, J=5.0 Hz, 1H), 2.01 (s, 3H), 1.96-1.84 (m, 5H), 1.79-1.64 (m, 4H), 1.62 (s, 3H), 1.62-1.50 (m, 3H), 1.44-1.30 (m, 3H), 1.22 (qd, J=12.0, 6.0 Hz, 1H), 1.10 (td, J=14.1, 8.9, 5.7 Hz, 1H), 0.84 (d, J=6.0 Hz, 3H); $^{13}$C NMR (125 MHz, CDCl$_3$) δ 170.8, 134.0, 121.0, 77.1, 42.1, 38.6, 35.4, 32.9, 32.7, 30.8, 30.4, 29.0, 25.3, 23.4, 21.9, 21.3, 16.7; IR (film): 2960, 2916, 2875, 2837, 1738, 1643, 1435, 1373, 1246, 1018 cm$^{-1}$; HRMS (ESI) m/z calc'd for C$_{17}$H$_{28}$O$_2$Na [M+Na]$^+$: 287.1987, found 287.1992; [α]$_D^{25}$=+103.9° (c=1.2, CHCl$_3$).

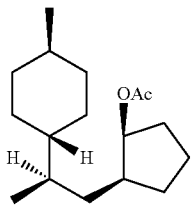 [SMILES: CC(=O)O[C@H]1CCC[C@H]1C[C@@H](C)[C@H]1CC[C@H](C)CC1]

(+)-(1S,2S)-2-((R)-2-((1r,4R)-4-methylcyclohexyl)propyl)cyclopentyl acetate (25). According to the procedure of Pfaltz (*Angew. Chem. Int. Ed.* 2006, 45, 5194), (+)-(1S,2S)-2-((R)-2-((R)-4-methylcyclohex-3-en-1-yl)propyl)cyclopentyl acetate was dissolved in CH$_2$Cl$_2$ (1.5 mL) in a 1 dram vial containing a stir bar. (+)-(R)-[1,5-Cycloocatdien-7-(2-phenyl-6,7-dihydro-5H-[1]pyridine)-di-(tert-butyl)-phosphinite-iridium(I)]-tetrakis-(3,5-bis(trifluoromethyl)-phenyl)-borate (9.0 mg, 0.006 mmol, 2 mol %) was added and the reaction was pressurized to 500 psi in an autoclave while stirring. After 5 h, the pressure was released and the reaction was concentrated. GC of the crude showed 24:1 dr. Flash chromatography on silica (~75 mL) eluting with 2% EtOAc/hexanes afforded the title compound in quantitative yield (79.9 mg, 0.3 mmol) as a colorless oil. $^1$H NMR (500 MHz, CDCl$_3$) δ 5.14 (t, J=5.0 Hz, 1H), 2.01 (s, 3H), 1.87-1.82 (m, 2H), 1.80-1.63 (m, 5H), 1.60-1.44 (m, 4H), 1.44-1.35 (m, 1H), 1.30-1.20 (m, 2H), 1.10-0.94 (m, 4H), 0.92-0.83 (m, 2H), 0.85 (d, J=6.5 Hz, 3H), 0.81 (s, J=7.0 Hz, 3H); $^{13}$C NMR (125 MHz, CDCl$_3$) δ 170.8, 77.2, 42.6, 42.2, 36.1, 35.7, 35.6, 33.2, 33.0, 32.7, 30.4, 30.1, 28.6, 22.7, 22.0, 21.3, 16.8; IR (film): 2949, 2918, 2868, 2854, 1738, 1645, 1448, 1373, 1246, 1018 cm$^{-1}$; HRMS (ESI) m/z calc'd for C$_{17}$H$_{30}$O$_2$Na [M+Na]$^+$: 289.2144, found 289.2152; [α]$_D^{23}$=+59.9° (c=1.2, CHCl$_3$).

The stereochemistry of this compound was assigned based on the stereochemical model proposed by Andersson (*Organometallics* 2010, 29, 6769) and confirmed by X-ray crystallographic analysis of the 3,5-dinitrobenzoate ester. To 20 mg of the solid 3,5-dinitrobenzoate ester in a 1 dram vial was added 1 mL hexane, 1 drop of PhH and the minimum amount of acetone needed to completely solubilize the compound. The vial was loosely capped and allowed so slowly evaporate to afford clear needles suitable for single crystal X-ray crystallographic analysis after 1-2 days. X-ray crystal structure data was then recorded.

Figure 7:
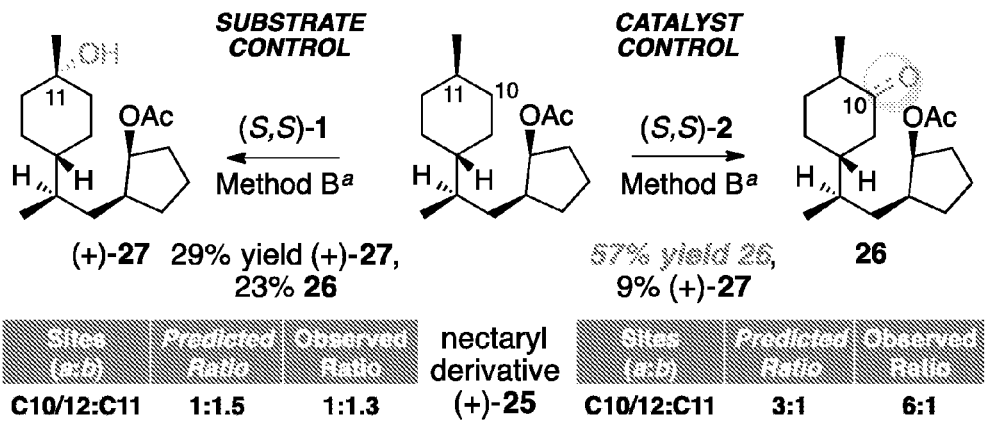
FIG. 7. Predictably Altering Inherent Site-Selectivity of C—H Oxidation. $^a$ Average of three runs. Starting material was recycled one time. Standard deviation=3%. A 3:1 ketone:alcohol ratio for 26 was obtained.

Data for the substrate controlled and catalyst controlled oxidation of nectaryl derivative (+)-25, and its corresponding structure-based reactivity data, are shown in FIG. 7.

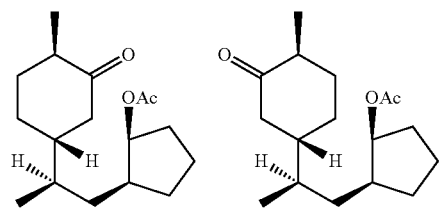 [SMILES: CC(=O)O[C@H]1CCC[C@H]1C[C@@H](C)[C@@H]1CC[C@@H](C)C(=O)C1 ; CC(=O)O[C@H]1CCC[C@H]1C[C@@H](C)[C@H]1CC[C@H](C)C(=O)C1]

(1S,2S)-2-((R)-2-((1R,4R)-4-methyl-3-oxocyclohexyl)propyl)cyclopentyl acetate and (1S,2S)-2-((R)-2-((1S,4S)-4-methyl-3-oxocyclohexyl)propyl)cyclopentyl acetate (26a). (+)-(1S,2S)-2-((R)-2-((1r,4R)-4-methylcyclohexyl)propyl)cyclopentyl acetate (25) (79.9 mg, 0.3 mmol, 1.0 equiv) in MeCN (0.5 mL) was reacted with (S,S)—Fe(CF$_3$-PDP) (2) according to Method B. Purification by flash chromatography on silica (~75 mL) eluting with 10→30% EtOAc/hexane. Overlapping peaks in the crude $^1$H NMR and GC made accurate 2°:3° ratio determination impossible so isolated ratios are reported. Run 1: recycled one time for a total of 40% 26a, 15% 26b, 10% (+)-27, 10% RSM, 5.4:1 2°:3° oxidation, 55% total 2° oxidation; cycle 1 26a (27.1 mg, 0.097 mmol, 32%), 26b (8.5 mg, 0.03 mmol, 10%), (+)-27 (5.7 mg, 0.02 mmol, 7%), RSM (26.0 mg, 0.1 mmol, 33%); cycle 2 26a (6.4 mg, 0.023 mmol, 23%), 26b (4.1 mg, 0.014 mmol, 14%), (+)-27 (2.7 mg, 0.01 mmol, 10%), RSM (7.6 mg, 0.029 mmol, 29%). Run 2: recycled one time for a total of 36% 26a, 12% 26b, 9% (+)-27, 7% RSM, 5.6:1 2°:3° oxidation; cycle 1 26a (25.2 mg, 0.09 mmol, 30%), 26b (7.6 mg, 0.027 mmol, 9%), (+)-27 (5.4 mg, 0.02 mmol, 6%), RSM (23.5 mg, 0.088 mmol, 29%); cycle 2 26a (4.7 mg, 0.017 mmol, 19%), 26b (3.3 mg, 0.01 mmol, 14%), (+)-27 (2.2 mg, 0.008 mmol, 9%), RSM (5.9 mg, 0.02 mmol, 22%). Run 3: recycled one time for a total of 65% 26a, 19% 26b, 11% (+)-27, 8% RSM, 5.8:1 2°:3° oxidation; cycle 1 26a (29.6 mg, 0.11 mmol, 35%), 26b (11.8 mg, 0.042 mmol, 14%), (+)-27 (6.8 mg, 0.024 mmol, 8%), RSM (24.3 mg, 0.091 mmol, 30%); cycle 2 26a (7.7 mg, 0.027 mmol, 30%), 26b (4.0 mg, 0.014 mmol, 15%), (+)-27 (2.5 mg, 0.009 mmol, 10%), RSM (6.1 mg, 0.023 mmol, 25%). Average overall yield 26a: 51±5%. Average overall yield 26b: 11±3%. Average overall yield 2° oxidation: 56%. Average overall yield (+)-27: 9±1%. Average overall RSM: 8±2%. Average ratio 2°:3° oxidation: 5.6±0.2:1. $^1$H NMR (500 MHz, CDCl$_3$) δ 5.11, (q, J=5.0 Hz, 1H), 2.34-2.22 (m, 2H), 2.50-2.01 (m, 2H), 1.99 and 1.98 (s, 3H), 1.90-1.80 (m, 2H), 1.77-1.67 (m, 3H), 1.67-1.34 (m, 7H), 1.31-1.22 (m, 1H), 1.11-1.04 (m, 1H), 0.97 (d, J=6.5 Hz, 3H), 0.87 and 0.85 (d, J=7.0 Hz, 3H); $^{13}$C NMR (125 MHz, CDCl$_3$) δ 213.4, 213.3, 170.6, 76.9, 45.6, 45.2, 45.1, 44.1, 41.9, 41.8, 35.8, 35.7, 35.0, 33.1, 32.8, 32.6, 30.2, 29.2, 27.6; IR (film): 2962, 2931, 2872, 1734, 1712, 1452, 1373, 1317, 1248, 1167, 1126, 1020, 972, 941, 887 cm$^{-1}$; HRMS (ESI) m/z calc'd for C$_{17}$H$_{29}$O$_3$ [M+H]$^+$: 281.2117, found 281.2126.

The site of oxidation was confirmed by independent preparation of an authentic standard (see below) and comparison of $^1$H NMR, $^{13}$C NMR, GC and mass spectrometry data.

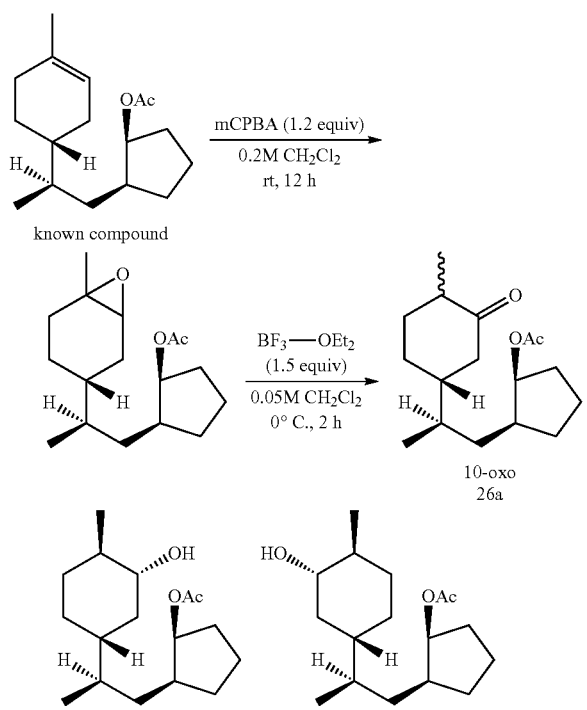

(1S,2S)-2-((R)-2-((1R,3R,4R)-3-hydroxy-4-methylcyclohexyl)propyl)cyclopentyl acetate and (1S,2S)-2-((R)-2-((1S,3S,4S)-3-hydroxy-4-methylcyclohexyl)propyl)cyclopentyl acetate (26b). $^1$H NMR (500 MHz, CDCl$_3$) δ 5.14 (app t, J=4.5 Hz, 1H), 3.10 (td, J=10.5, 4.5 Hz, 1H), 2.02 (s, 3H), 1.93-1.84 (m, 2H), 1.81-1.67 (m, 5H), 1.61-1.46 (m, 4H), 1.43-1.19 (m, 6H), 1.05-1.13 (m, 1H), 1.02-0.96 (m, 1H), 0.99 (d, J=6.5 Hz, 3H), 0.84 (d, J=7.0 Hz, 3H); $^{13}$C NMR (125 MHz, CDCl$_3$) δ 170.9, 77.2, 76.7, 42.1, 41.7, 40.3, 37.7, 35.7, 33.3 (2C), 32.7, 30.4, 29.4, 22.0, 21.3, 18.3, 16.6; IR (film): 3421, 2924, 2872, 1736, 1452, 1375, 1250, 1165, 1147, 1124, 1034, 1020, 974, 939, 841 cm$^{-1}$; HRMS (ESI) m/z calc'd for C$_{17}$H$_{31}$O$_3$ [M+H]$^+$: 283.2273, found 283.2275.

The site of oxidation was determined by oxidizing products 26b with DMP to afford products 26a as determined by matching their $^1$H NMR, $^{13}$C NMR, GC and mass spectrometry data. The stereochemistry of the hydroxyl group was assigned based on the coupling constants and splitting pattern of the C10 proton at 3.10 ppm, which is an axial proton coupling to two other axial protons (J=10.5 Hz) and 1 equatorial proton (J=4.5 Hz).

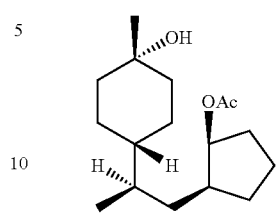

(+)-(1S,2S)-2-((R)-2-((1s,4S)-4-hydroxy-4-methylcyclohexyl)propyl)cyclopentyl acetate (27). $^1$H NMR (500 MHz, CDCl$_3$) δ 5.14 (app t, J=4.0 Hz, 1H), 2.01 (s, 3H), 1.93-1.83 (m, 2H), 1.79-1.49 (m, 6H), 1.45-1.29 (m, 8H), 1.26-1.20 (m, 1H), 1.19 (s, 3H), 1.12-1.05 (m, 2H), 0.84 (d, J=7.0 Hz, 3H); $^{13}$C NMR (125 MHz, CDCl$_3$) δ 170.9, 77.1, 69.3, 42.2, 42.1, 39.0, 38.9, 35.8, 33.0, 32.7, 31.4, 30.4, 25.1, 23.9, 21.9, 21.3, 16.8; IR (film): 3437, 2956, 2926, 2870, 1736, 1720, 1446, 1373, 1248, 1167, 1124, 1020, 973, 941, 910 cm$^{-1}$; HRMS (ESI) m/z calc'd for C$_{17}$H$_{30}$O$_3$Na [M+Na]$^+$: 305.2093, found 305.2096; [α]$_D^{23}$=+46.9° (c=1.0, CHCl$_3$).

The site of oxidation was assigned based on $^1$H NMR. The two methyl groups in the starting material show up as doublets whereas in the product they appear as a singlet and a doublet. This indicates oxidation at either the C7 or C11 tertiary sites. A 1H-1H TOCSY experiment with 300 ms mix time allows the C1 proton α-to the acetate to see coupling to the C7 methyl group. These two protons in the same spin system is only possible if there is a C7 proton (i.e., an unoxidized tertiary site).

TABLE 7.1

Catalyst Comparison for the Oxidation of (+)-Nectaryl Derivative (25).

| Catalyst | % isolated yield 26a | % isolated yield 26b | % isolated yield total 2° oxidation | % isolated yield (+)-27 | % isolated yield RSM | 2°:3°[b] |
|---|---|---|---|---|---|---|
| (S,S)—Fe(PDP) (1) | 24[a] | 0 | 24 | 30 | 15 | 1:1.3 |
| (R,R)—Fe(PDP) (1) | 14[c] | 0 | 14 | 19 | 15 | 1:1.4 |
| (S,S)—Fe(CF$_3$- PDP) (2)[d] | 41[a] | 16 | 57 | 9 | 8 | 6:1 |
| (R,R)—Fe(CF$_3$- PDP) (2) | 15[c] | 9 | 24 | 6 | 33 | 4:1 |

[a]Average of 3 runs at 0.3 mmol.
[b]Isolated ratio.
[c]Average of 2 runs at 0.3 mmol.
[d]Starting material was recycled 1 time.

Oxidation with (S,S)—Fe(PDP) (1) according to Method B. Run 1: 26a (20.4 mg, 0.072 mmol, 24%), (+)-27 (23.9 mg, 0.085 mmol, 28%), RSM (10.8 mg, 0.041 mmol, 14%), 1:1.2 2°:3°. Run 2: 26a (18.6 mg, 0.066 mmol, 22%), (+)-27 (25.4 mg, 0.09 mmol, 30%), RSM (10.2 mg, 0.038 mmol, 13%) 1:1.4 2°:3°. Run 3: 26a (21.2 mg, 0.075 mmol, 25%), (+)-27 (27.5 mg, 0.097 mmol, 32%), RSM (14.5 mg, 0.054 mmol, 18%), 1:1.3 2°:3°. Average yield 26a: 23%. Average yield 2° oxidation: 23±2%. Average yield (+)-27: 29±2%. Average RSM: 14±3%. Average ratio 2°:3° oxidation: 1:1.3±0.1.

Oxidation with (R,R)—Fe(PDP) (1) according to Method B. Run 1: 26a (12.0 mg, 0.042 mmol, 14%), (+)-27 (18.0 mg, 0.063 mmol, 21%), RSM (11.7 mg, 0.045 mmol, 15%). Run 2: 26a (10.9 mg, 0.039 mmol, 13%), (+)-27 (14.6 mg, 0.051 mmol, 17%), RSM (12.8 mg, 0.046 mmol, 15%).

Average yield 26a: 14%. Average yield (+)-27: 19%. Average RSM: 15%. Average ratio 2°:3° oxidation: 1:1.4. Oxidation with (R,R)—Fe(CF$_3$-PDP) (2) according to Method B. Run 1: 26a (11.8 mg, 0.042 mmol, 14%), 26b (7.6 mg, 0.026 mmol, 9%), (+)-27 (4.4 mg, 0.016 mmol, 5%), RSM (27.9 mg, 0.11 mmol, 35%). Run 2: 26a (12.4 mg, 0.044 mmol, 15%), 26b (9.9 mg, 0.035 mmol, 9%), (+)-27 (5.8 mg, 0.021 mmol, 6%), RSM (23.8 mg, 0.09 mmol, 30%). Average yield 26a: 15%. Average yield 26b: 9%. Average yield 2° oxidation: 24%. Average yield (+)-27: 6%. Average RSM: 33%. Average ratio 2°:3° oxidation: 4:1.

Example 8

Validating the Predictive Power of the Structure-Based Catalyst Reactivity Models Parameterized Site Filters for Complex Molecules. Tables 8.1-8.3 show the parameterized site filter for determining likely sites of oxidation for (−)-Triacetoxy Tricalysiolide B (19), (+)-Artemisinin (22), and (+)-Nectaryl derivative (25).

TABLE 8.1

Parameterized Site Filter for Determining Likely Sites of Oxidation for (−)-Triacetoxy Tricalysiolide B (19).

| Site ($H_{eq}$ atom) | Electronic Parameter (E) | Steric/Stereoelectronic Parameter (S) |
|---|---|---|
| 9 | 0.201 (red) | 15.4 (blue) |
| 11 | 0.206 (red) | 9.1 (purple) |
| 7 | 0.208 (red) | 8.6 (purple) |
| 1 | 0.211 (purple) | 9.5 (purple) |
| 14 | 0.212 (purple) | 11.3 (blue) |
| 6 | 0.213 (purple) | 5.6 (red) |
| 12 | 0.215 (purple) | 7.8 (red) |
| 5 | 0.220 (purple) | 15.7 (blue) |
| 13 | 0.223 (blue) | 11.4 (blue) |
| 15 | 0.226 (blue) | 12.5 (blue) |
| 2 | 0.229 (blue) | 8.4 (purple) |
| red lower limit | 0.201 (lowest E) | 5.6 (lowest S) |
| purple lower Limit | 0.211 = 0.201 + 5% | 7.8 = 5.6 + 40% |
| blue lower limit | 0.222 = 0.211 + 5% | 10.9 = 7.8 + 40% |

TABLE 8.2

Parameterized Site Filter for Determining Likely Sites of Oxidation for (+)-Artemisinin (22).

| Site ($H_{eq}$ atom) | Electronic Parameter (E) | Steric/Stereoelectronic Parameter (S) |
|---|---|---|
| 10 | 0.186 (red) | 10.6 (purple) |
| 5 | 0.187 (red) | 14.7 (blue) |
| 9 | 0.206 (purple) | 6.0 (red) |
| 1 | 0.210 (blue) | 13.3 (blue) |
| 2 | 0.212 (blue) | 6.9 (red) |
| 3 | 0.213 (blue) | 8.6 (purple) |
| 8 | 0.216 (blue) | 6.9 (red) |
| 7 | 0.216 (blue) | 12.8 (blue) |
| 11 | 0.253 (blue) | 9.1 (purple) |
| red lower limit | 0.186 (lowest E) | 6.0 (lowest S) |
| purple lower Limit | 0.195 = 0.186 + 5% | 8.4 = 6.0 + 40% |
| blue lower limit | 0.206 = 0.195 + 5% | 11.8 = 8.4 + 40% |

TABLE 8.3

Parameterized Site Filter for Determining Likely Sites of Oxidation for (+)-Nectaryl derivative (25).

| Site ($H_{eq}$ atom) | Electronic Parameter (E) | Steric/Stereoelectronic Parameter (S) |
|---|---|---|
| 11 | 0.181 (red) | 9.3 (purple) |
| 8 | 0.187 (red) | 9.8 (purple) |
| 7 | 0.189 (red) | 9.6 (purple) |
| 10, 12 | 0.198 (purple) | 6.0 (red) |
| 3 | 0.198 (purple) | 6.5 (red) |
| 9, 13 | 0.199 (purple) | 6.9 (red) |
| 4 | 0.200 (blue) | 6.9 (red) |
| 5 | 0.201 (blue) | 9.7 (purple) |
| 6 | 0.204 (blue) | 9.1 (purple) |
| 1 | 0.207 (blue) | 8.7 (purple) |
| 2 | 0.211 (blue) | 6.0 (red) |
| red lower limit | 0.181 (lowest E) | 6.0 (lowest S) |
| purple lower Limit | 0.190 = 0.181 + 5% | 8.4 = 6.0 + 40% |
| blue lower limit | 0.199 = 0.190 + 5% | 11.8 = 8.4 + 40% |

A. Structure-Based Catalyst Reactivity Model Predictions for Likely Sites of Oxidation in Other Substrates in this disclosure. All calculated and observed $\Delta\Delta G^{\ddagger}$'s are corrected for statistics. For example if there are two equivalent sites in a molecule because of a plane of symmetry, there is twice the likelihood that the site will be oxidized in relation to a site with only one possible outcome. So for example, if we observe a 4:1 ratio for oxidation favoring that site, after correcting for statistics, it is recorded for the purpose of the model as a 2:1 selectivity, $\Delta\Delta G^{\ddagger}=0.41$ kcal/mol. Similarly, if we calculate $\Delta\Delta G^{\ddagger}=0.50$ kcal/mol for that site (2.3:1 selectivity), because the equations report data already corrected for statistics, the calculations would predict that we observe a ~5:1 ratio. Substrate 10 exemplifies this correction. There is a plane of symmetry running through C4 and C1 making C3 and C5 equivalent.

TABLE 8.4

Calculated $\Delta\Delta G^{\ddagger}$ for All Likely to be Oxidized Sites for Fe(PDP) (1).

| Substrate | Sites Compared (a:b) | Calc'd $\Delta\Delta G^{\ddagger}$ (kcal/mol)* | Observed $\Delta\Delta G^{\ddagger}$ (kcal/mol)[†] | Obs-calc'd (kcal/mol) |
|---|---|---|---|---|
| 6 | 1/6:2/5 | 0.45 | 0.16 | −0.29 |
|  | 1/6:3/4 | 0.34 | 0.02 | −0.32 |
| 10 | 4:3/5 | 1.00 | 0.82 | −0.18 |
| (+)-S12 | C2:C3 | 0.44 | 0.20 | −0.24 |
|  | C2:C1 | 0.80 | 0.90 | 0.10 |
| (−)-19 | C6:C7 | −0.06 | 0.24 | 0.30 |
|  | C6:C11 | −0.20 | N/A | N/A |
|  | C6:C12 | 0.84 | N/A | N/A |
| (+)-22 | C10:C9 | 0.18 | 0.49 | 0.31 |

*Output $\Delta\Delta G^{\ddagger}$ has been designed into the equation to be corrected for statistics (i.e. two possible sites C3/5 versus one C4 in 10).
[†]Observed $\Delta\Delta G^{\ddagger}$ corrected for statistics.

The calculated and observed values match within a reasonable margin of error for all sites where the data can be compared.

TABLE 8.5

Calculated $\Delta\Delta G^{\ddagger}$ for All Likely to be Oxidized Sites in the Complex Molecules for Fe(CF$_3$-PDP) (2).

| Substrate | Sites Compared (a:b) | Calc'd $\Delta\Delta G^{\ddagger}$ (kcal/mol)* | Observed $\Delta\Delta G^{\ddagger}$ (kcal/mol)[†] | Obs-calc'd (kcal/mol) |
|---|---|---|---|---|
| 6 | 1/6:2/5 | −0.66 | −0.77 | −0.12 |
|  | 1/6:3/4 | −0.87 | −1.05 | −0.18 |

TABLE 8.5-continued

Calculated ΔΔG‡ for All Likely to be Oxidized Sites in the Complex Molecules for Fe(CF₃-PDP) (2).

| Substrate | Sites Compared (a:b) | Calc'd ΔΔG‡ (kcal/mol)* | Observed ΔΔG‡ (kcal/mol)‡ | Obs-calc'd (kcal/mol) |
|---|---|---|---|---|
| 10 | 4:3/5 | 0.10 | 0 | −0.10 |
| (+)-S12 | C2:C3 | 0.77 | 0.56 | −0.20 |
|  | C2:C1 | 1.03 | 1.03 | 0.0 |
| (−)-19 | C6:C7 | 1.40 | 1.56 | 0.16 |
|  | C6:C11 | 2.25 | N/A | N/A |
|  | C6:C12 | 1.01 | N/A | N/A |
| (+)-22 | C10:C9 | −1.63 | −1.49 | 0.14 |

*Output ΔΔG‡ has been designed into the equation to be corrected for statistics (i.e. two possible sites C3/5 versus one C4 in 4).
‡Observed ΔΔG‡ corrected for statistics.

The calculated and observed values match within a reasonable margin of error for all sites where the data can be compared. For sites C11 and C12 in (−)-19, the model accurately predicts that C11 will not be oxidized; however, C12 seems to be an outlier because of it is predicted to be more reactive than C7 (although still a minor product compared to C6, calc'd C6:C12 5.6:1).

B. Validating the Structure-Based Catalyst Reactivity Models on Substrates Whose Data was Not Used to Create It.

TABLE 8.6

E and S Parameters Calculated for Substrates (+)-3 and (+)-25.

| Substrate | Site | E* | S* | $E_n$† | $S_n$† |
|---|---|---|---|---|---|
| (+)-3 | 2 | 0.214 (blue) | 8.7 (purple) |  |  |
|  | 3 | 0.203 (purple) | 6.4 (red) | 0.2114 | −0.5240 |
|  | 4 | 0.185 (red) | 9.2 (purple) | −1.1419 | 0.5092 |
|  | 5 | 0.189 (red) | 6.0 (red) | −0.8277 | −0.6974 |
| (+)-25 | 1 | 0.207 (blue) | 8.7 (purple) |  |  |
|  | 2 | 0.211 (blue) | 6 (red) |  |  |
|  | 3 | 0.198 (purple) | 6.5 (red) | −0.1636 | −0.5018 |
|  | 4 | 0.200 (blue) | 6.9 (red) |  |  |
|  | 5 | 0.201 (blue) | 9.7 (purple) |  |  |
|  | 6 | 0.204 (blue) | 9.1 (purple) |  |  |
|  | 7 | 0.189 (red) | 9.6 (purple) | −0.8595 | 0.6642 |
|  | 8 | 0.187 (red) | 9.8 (purple) | −0.9986 | 0.7195 |
|  | 9/13 | 0.199 (purple) | 6.9 (red) | −0.0999 | −0.3469 |
|  | 10/12 | 0.198 (purple) | 6 (red) | −0.2114 | −0.7690 |
|  | 11 | 0.181 (red) | 9.3 (purple) | −1.4337 | 0.5461 |

*Coloring based on the parameterized site filter. Only red-red or red-purple sites considered.
†Normalized parameters only reported for likely to be oxidized sites.

TABLE 8.7

Calculated Selectivities for Substrates (+)-3 and (+)-25 for Oxidation with Fe(PDP) 1.

| Substrate | Sites Compared (ratio a:b) | $\Delta E_{ab}$ | $\Delta S_{ab}$ | Calc'd ΔΔG‡ (kcal/mol)* | Observed ΔΔG‡ (kcal/mol)† | obs-calc'd (kcal/mol) |
|---|---|---|---|---|---|---|
| (+)-3 | 5:4 | 0.3143 | 1.2066 | 0.08 | 0.24 | 0.16 |
|  | 5:3 | 1.0391 | 0.1734 | 1.68 | N/A | N/A |
| (+)-25 | 11:10/12 | 1.2251 | −1.2251 | 0.65 | 0.49 | −0.16 |
|  | 11:9/13 | 1.3338 | −0.8930 | 1.26 | N/A | N/A |
|  | 11:8 | 0.1734 | 0.7422 | 0.74 | N/A | N/A |
|  | 11:7 | 0.5742 | 0.1181 | 0.91 | N/A | N/A |
|  | 11:3 | 1.27 | −1.048 | 0.93 | N/A | N/A |

*Output ΔΔG‡ has been designed into the equation to be corrected for statistics (i.e. two possible sites 10/12 versus one C11 in (+)-25).
†Observed ΔΔG‡ corrected for statistics.

TABLE 8.8

Calculated Selectivities for Substrates (+)-3 and (+)-25 for Oxidation with Fe(CF₃-PDP) 2.

| Substrate | Sites Compared (ratio a:b) | Calc'd ΔΔG‡ (kcal/mol)* | Observed ΔΔG‡ (kcal/mol)† | obs-calc'd (kcal/mol) |
|---|---|---|---|---|
| (+)-3 | 5:4 | 1.21 | 0.83 | −0.38 |
|  | 5:3 | 3.84 | N/A | N/A |
| (+)-25 | 11:10/12 | −0.28 | −0.53 | −0.25 |
|  | 11:9/13 | 1.14 | N/A | N/A |
|  | 11:8 | 0.35 | N/A | N/A |
|  | 11:7 | 0.78 | N/A | N/A |
|  | 11:3 | 0.36 | N/A | N/A |

*Output ΔΔG‡ has been designed into the equation to be corrected for statistics (i.e. two possible sites 10/12 versus one C11 in (+)-25).
†Observed ΔΔG‡ corrected for statistics.

Using the equation requires setting some site (a) as the reference site to which the selectivity of all other sites (b) is compared. For new substrates, for which the major site of oxidation is not known, either the most electron rich or least sterically hindered site of sites likely to be oxidized (from the narrowing filter, see the discussion above regarding Parameterized Site Filter for Analysis of Substrate Reactivity) should be selected based on the calculated E and S parameters. For (+)-3, the major site was known for catalyst 1, so C5 was set as the reference site, while for (+)-25 the most electron rich site was likely to be a major site of oxidation with catalyst 1, so C11 was selected as the reference site.

The calculations predict the site-selectivity trend of the reactions and give a reasonable estimate for the magnitude of the observed site selectivity, without the need for prior experimental determination. That is, this model effectively predicts non-selective, moderately selective and highly selective reactions. For (+)-3 the C5:C4 2°:3° ratio is predicted within 0.16 kcal/mol for catalyst 1 and 0.38 kcal/mol for catalyst 2. Notably, the other likely site of oxidation C3 (as determined by applying our narrowing filter) is predicted to be very unreactive (17 and 600 times less reactive than C5), consistent with the experimental observation that no C3 oxidation is observed. For (+)-25, other sites, particularly C7 are predicted to be somewhat reactive compared to C11 for Fe(PDP) 1 and to a lesser extent Fe(CF₃-PDP) 2. The reduced mass balance of the reaction of (+)-25 with each catalyst (~70%) is indicative of oxidation at one or more other sites. The GC traces of these reactions confirms the presence of some minor other products. Although sufficient quantities of these products are not produced to isolate and identify them, we suspect that, as predicted by the equation, small amount of other oxidations are occurring. Importantly, oxidation of (+)-25, despite many other likely sites of oxidation, provides preparative yields (52%) of C10/12 oxidation.

Example 9

Matched-Mismatched Reactivity and Chirality Controlled C—H Oxidation

In addition to altering the steric environment along a substrate's approach to the catalyst active site using trajectory restriction, we have also demonstrated that such modifications can alter the chiral environment around the metal center. The iron catalysts described herein can be utilized both to control the site-selective oxidation of chiral substrates and to carry out enantioselective oxidations of achiral substrates. Examples of site-selective oxidation may be observed in the differential reactivity of complex organic substrates (e.g., a nectaryl derivative, sclareolide and artemisinin) with opposite enantiomers of the Fe(CF$_3$-PDP) and Fe(PDP) catalyst.

Scheme 9.1 shows the yields obtained with the (S,S) or (R,R) catalysts for various chiral substrates. Because the C—H bonds in those molecules reside in different chiral environments, the catalyst substrate interactions that control the site-selectivity depend not only on sterics, but also the chirality of the catalyst. In the nectaryl derivative, (S,S)—Fe(CF$_3$-PDP) provides much higher yield and selectivity for oxidation at the C10/12 position compared to (R,R)—Fe(CF$_3$-PDP). Similar results are observed in sclareolide and artemisinin. Furthermore, in the oxidation of (S)-2-acetoxy-3-cyclohexylpropanoic acid, (S,S)—Fe(PDP) affords a 4:1 ratio of the 5-membered (5):6-membered (6) lactones; however, the opposite enantiomer inverts this ratio to 1:2 5:6 (Scheme 9.1 B). The achiral Fe(mep) catalyst provides no selectivity indicating that the chiral environment around the metal center is the controlling factor for site-selectivity.

Fe(mep) (non-selective complex) =

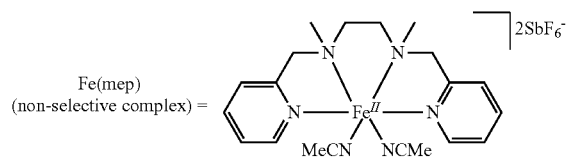

Scheme 9.1

A. Chiral catalyst-chiral substrate matched-mismatched reactivity

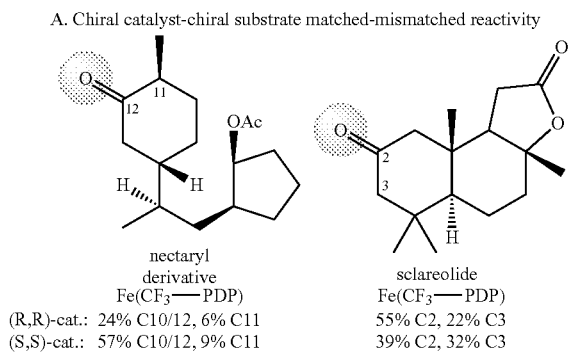

nectaryl derivative
Fe(CF$_3$—PDP)
(R,R)-cat.: 24% C10/12, 6% C11
(S,S)-cat.: 57% C10/12, 9% C11 sclareolide
Fe(CF$_3$—PDP)
55% C2, 22% C3
39% C2, 32% C3

-continued

B. Chirality controlled C—H oxidation

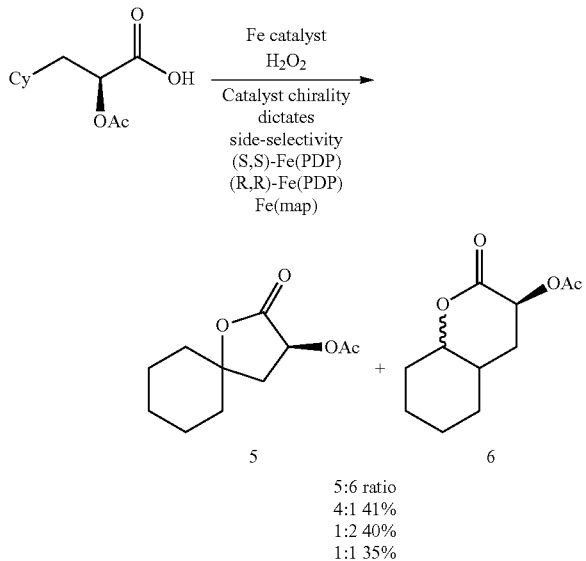

5:6 ratio
4:1 41%
1:2 40%
1:1 35%

The chiral environment provided by the Fe(CF$_3$-PDP) catalyst can also induce enantioselectivity in achiral substrates (Scheme 9.2). In these cases, both C—H bonds are equivalent sterically, so it is the chiral environment around the metal center alone that distinguishes between the bonds. Oxidation of 2,2-dimethylhexanoic acid with (R,R)—Fe(CF$_3$-PDP) provides the lactone in 36% ee. Modifications to the catalyst that enhance or alter the chiral environment, such as methylation of the bispyrrolidines as in Fe(DMPDP) improves the ee to 41% or 64% at −30° C.

Scheme 9.2

Enantioselective C—H oxidation

| catalyst | % ee |
| --- | --- |
| (R,R)-Fe(PDP) | −7 |
| (R,R)-Fe(CF$_3$-PDP) | −36 |
| (R,R,S,S)-Fe(DMPDP), RT | +41 |
| (R,R,S,S)-Fe(DMPDP,) -30° C. | +64 |

Figure 11:
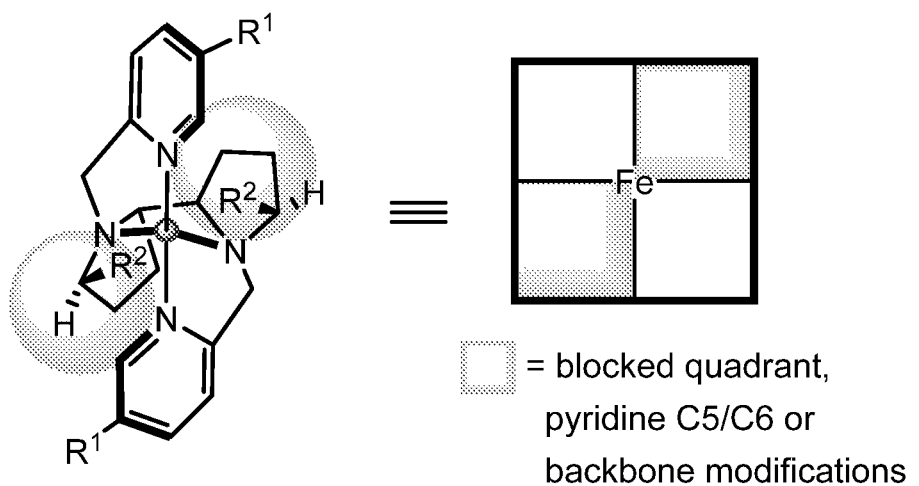
FIG. 11. A schematic showing the C-2 symmetric ((R,R) or (S,S,R,R)) iron catalyst as an open quadrant-blocked quadrant structure.

This effect can be understood viewing the C-2 symmetric catalyst as an open quadrant-blocked quadrant structure, a feature similar to other asymmetric catalysts (FIG. 11). The catalyst pyridines, as well as modifications on the pyridines or the bispyrrolidine, block two of the quadrants thereby creating a chiral environment. For example, the aryl groups of Fe(CF$_3$-PDP) or the methyl groups of Fe(DMPDP) extend into these quadrants and amplify the chiral environment around the metal center compared to Fe(PDP). The success of this approach indicates that steric modifications in these quadrants can be used to enhance site-selectivity based on catalyst chirality and to carry out a wide variety of enantioselective reactions.

Example 10

Tri-CF$_3$-PDP Extends Catalyst Lifetime and Improves Selectivities

To reduce catalyst loading carrying out the selective oxidations, we designed and synthesized a new catalyst, Fe(tri-CF$_3$-PDP) (2) (Scheme 10.1). The additional electron-withdrawing —CF$_3$ group on the phenyl ring make the ring more stable and also sterically prevents the formation of oligomers during oxidation.

Scheme 10.1. Fe(CF$_3$—PDP) (1) and Fe(tri-CF$_3$—PDP) (2).

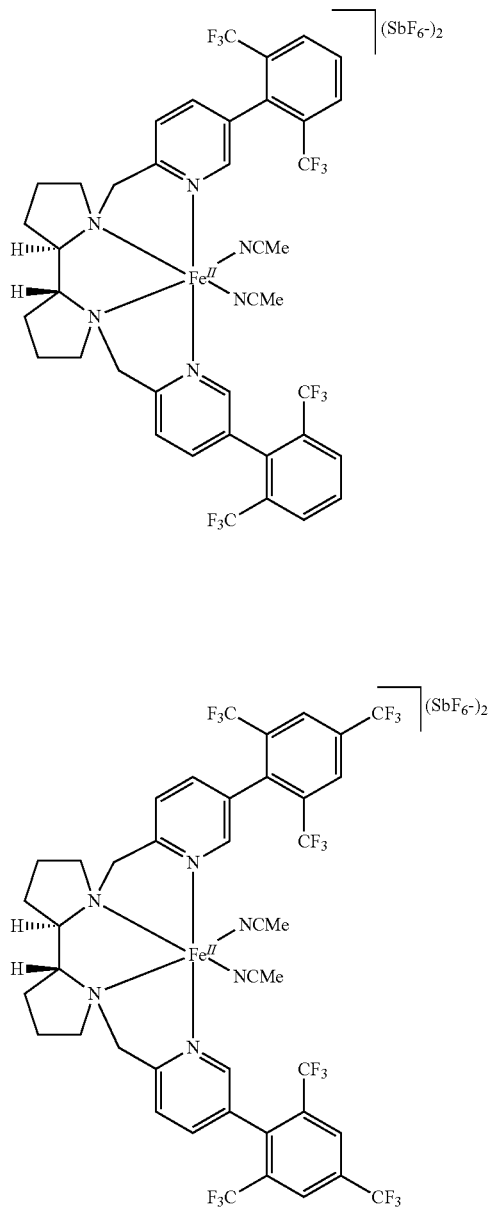

Both (R,R)-1 and (R,R)-2 were evaluated via the oxidation of methyl N-nosyl isoleucinate (3) under reduced catalyst loadings (Table 10.1).

TABLE 1

Oxidation of Methyl N-Nosyl Isoleucinate (3).

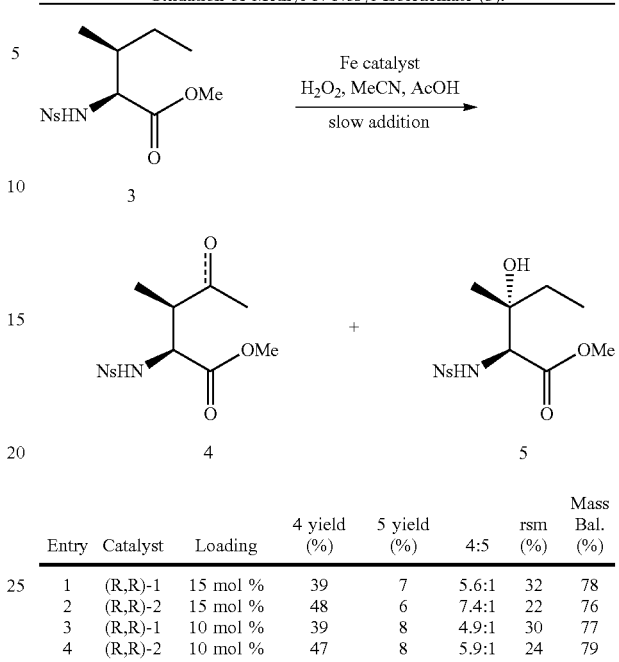

| Entry | Catalyst | Loading | 4 yield (%) | 5 yield (%) | 4:5 | rsm (%) | Mass Bal. (%) |
|---|---|---|---|---|---|---|---|
| 1 | (R,R)-1 | 15 mol % | 39 | 7 | 5.6:1 | 32 | 78 |
| 2 | (R,R)-2 | 15 mol % | 48 | 6 | 7.4:1 | 22 | 76 |
| 3 | (R,R)-1 | 10 mol % | 39 | 8 | 4.9:1 | 30 | 77 |
| 4 | (R,R)-2 | 10 mol % | 47 | 8 | 5.9:1 | 24 | 79 |

Isolated yield.
Slow addition: 0.5 mmol 3, 5 eq H$_2$O$_2$, 0.5 eq AcOH, addition rate 5 mL/min, added in ~80 min When reducing the catalyst loading from 15 mol % to 10 mol %, the secondary oxidation yield remains the same. This may be due to the fact that decreased loading of catalyst is compensated by increased equivalence of H$_2$O$_2$ and AcOH relative to the catalyst. Notably, 2 consistently performs better than 1, and has reached the same yield as when using 1 in 25 mol % loading (entry 4). The secondary/tertiary ratio also increased. These data indicate that by using 2 as the oxidation catalyst, the catalyst loading can be lowered to 10 mol % or less while obtaining the same secondary oxidation yield and improved selectivity.

Synthesis and Characterization of Catalyst Fe(tri-CF$_3$-PDP) (2)

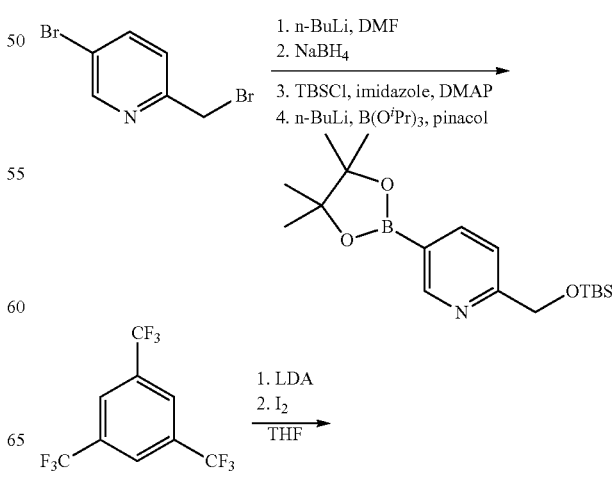

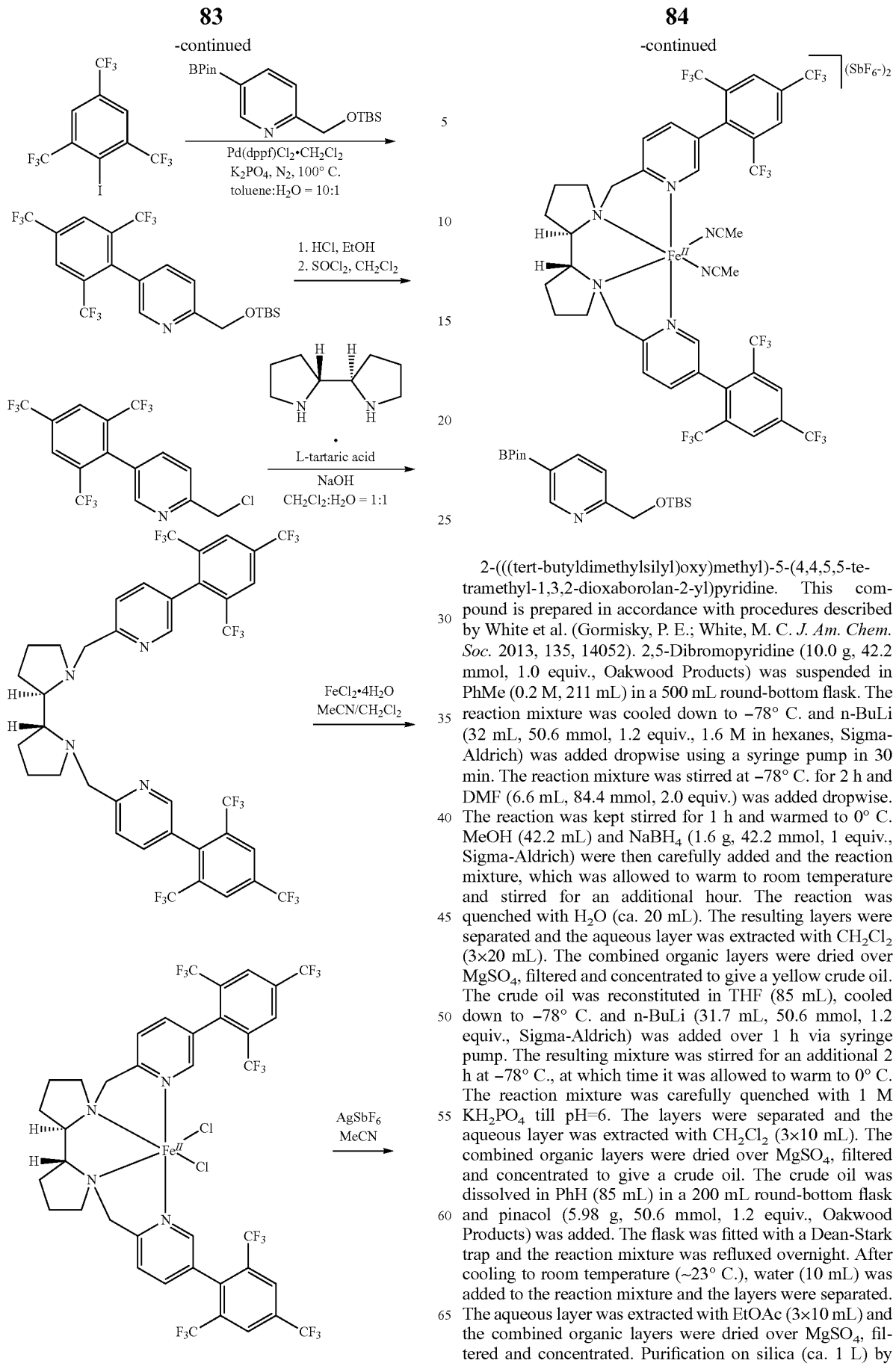

2-(((tert-butyldimethylsilyl)oxy)methyl)-5-(4,4,5,5-tetramethyl-1,3,2-dioxaborolan-2-yl)pyridine. This compound is prepared in accordance with procedures described by White et al. (Gormisky, P. E.; White, M. C. *J. Am. Chem. Soc.* 2013, 135, 14052). 2,5-Dibromopyridine (10.0 g, 42.2 mmol, 1.0 equiv., Oakwood Products) was suspended in PhMe (0.2 M, 211 mL) in a 500 mL round-bottom flask. The reaction mixture was cooled down to −78° C. and n-BuLi (32 mL, 50.6 mmol, 1.2 equiv., 1.6 M in hexanes, Sigma-Aldrich) was added dropwise using a syringe pump in 30 min. The reaction mixture was stirred at −78° C. for 2 h and DMF (6.6 mL, 84.4 mmol, 2.0 equiv.) was added dropwise. The reaction was kept stirred for 1 h and warmed to 0° C. MeOH (42.2 mL) and $NaBH_4$ (1.6 g, 42.2 mmol, 1 equiv., Sigma-Aldrich) were then carefully added and the reaction mixture, which was allowed to warm to room temperature and stirred for an additional hour. The reaction was quenched with $H_2O$ (ca. 20 mL). The resulting layers were separated and the aqueous layer was extracted with $CH_2Cl_2$ (3×20 mL). The combined organic layers were dried over $MgSO_4$, filtered and concentrated to give a yellow crude oil. The crude oil was reconstituted in THF (85 mL), cooled down to −78° C. and n-BuLi (31.7 mL, 50.6 mmol, 1.2 equiv., Sigma-Aldrich) was added over 1 h via syringe pump. The resulting mixture was stirred for an additional 2 h at −78° C., at which time it was allowed to warm to 0° C. The reaction mixture was carefully quenched with 1 M $KH_2PO_4$ till pH=6. The layers were separated and the aqueous layer was extracted with $CH_2Cl_2$ (3×10 mL). The combined organic layers were dried over $MgSO_4$, filtered and concentrated to give a crude oil. The crude oil was dissolved in PhH (85 mL) in a 200 mL round-bottom flask and pinacol (5.98 g, 50.6 mmol, 1.2 equiv., Oakwood Products) was added. The flask was fitted with a Dean-Stark trap and the reaction mixture was refluxed overnight. After cooling to room temperature (~23° C.), water (10 mL) was added to the reaction mixture and the layers were separated. The aqueous layer was extracted with EtOAc (3×10 mL) and the combined organic layers were dried over $MgSO_4$, filtered and concentrated. Purification on silica (ca. 1 L) by flash chromatography eluting with 12.5% to 50% EtOAc/hexanes afforded the title compound (5.48 g, 15.6 mmol, 37% yield over 4 steps) as yellow oil. $^1$H NMR (400 MHz, CDCl$_3$) δ 8.83 (s, 1H), 8.08 (dd, J=7.8, 1.7 Hz, 1H), 7.50 (d, J=7.8 Hz, 1H), 1.35 (s, 12H), 0.95 (s, 9H), 0.11 (s, 6H). The spectral data match those reported in the literature.

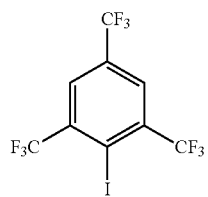

2-iodo-1,3,5-tris(trifluoromethyl)benzene. A 300 mL round-bottom flask fitted with a rubber septum was charged with a stir bar and Et$_2$O (120 mL). The solvent was cooled down to −78° C. and i-Pr$_2$NH (2.6 mL, 18.4 mmol, 2.1 equiv.) was added. n-BuLi (11.0 mL, 17.5 mmol, 2.0 equiv., 1.6 M in hexanes, Sigma-Aldrich) was then added dropwise. The reaction was stirred under −78° C. for 15 min and was allowed to warm to 0° C. The reaction mixture was kept stirred for 5 min, at which time 1,3,5-tris(trifluoromethyl)benzene (2.47 g, 8.76 mmol, 1.0 equiv., TCI) dissolved in Et$_2$O (4.8 mL) was added dropwise. The black mixture was stirred at 0° C. for 1.25 h, and quenched with iodine (4.45 g, 17.5 mmol, 2 equiv., Sigma-Aldrich). The mixture was transferred into a 500 mL separatory funnel, and washed with saturated Na$_2$S2O$_3$ (4×100 mL), brine (2×50 mL) and 1 M HCl (3×75 mL). The aqueous layers before the HCl wash was extracted with Et$_2$O (60 mL). The organic layers were combined, dried over MgSO$_4$, filtered and concentrated under reduced pressure in ice bath. Purification by flash chromatography on silica (ca. 150 mL) eluting with pentane afforded a purple solution. The solution was washed with saturated Na$_2$S203 (50 mL) and concentrated under reduced pressure in ice bath nearly to dryness, and then dried under a stream of N$_2$ for 30 min to afford a white crystal. $^1$H NMR (400 MHz, CDCl$_3$) δ 8.04 (s, 2H); $^{13}$C NMR (125 MHz, Chloroform-d) δ 138.35 (q, J=31.4 Hz), 131.56 (q, J=34.8 Hz), 127.39 (dq, J=12.7, 3.2 Hz), 122.73 (q, J=273.0 Hz), 122.22 (q, J=275.1 Hz), 94.89 (s).

Ligands with other substitution patterns on the phenyl ring can be prepared by using iodobenzenes with other trifluoromethyl substitution patterns. For example, the ligand can be prepared using 2-iodo-1,3,4-tris(trifluoromethyl)benzene as a starting material to provide the ligand of other complexes of Formula (I).

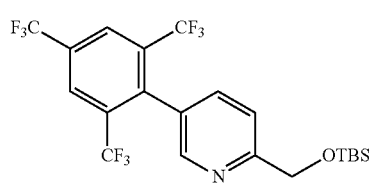

2-(((tert-butyldimethylsilyl)oxy)methyl)-5-(2,4,6-tris(trifluoromethyl)phenyl)pyridine. A 50 mL round-bottom flask was charged with a stir bar and Pd(dppf)Cl$_2$CH$_2$Cl$_2$ (216 mg, 0.265 mmol, 0.03 equiv., Sigma-Aldrich), 2-iodo-1,3,5-tris(trifluoromethyl)benzene (3.60 g, 8.82 mmol, 1.0 equiv.) and K$_3$PO$_4$ (3.75 g, 17.65 mmol, 2 equiv., Strem). The flask was evacuated and refilled with N$_2$ (×3). Toluene (16 mL) and water (1.6 mL) was added, followed by 2-(((tert-butyldimethylsilyl)oxy)methyl)-5-(4,4,5,5-tetramethyl-1,3,2-dioxaborolan-2-yl)pyridine (4.62 g, 13.23 mmol, 1.5 equiv.). The rubber septum was quickly replaced with a yellow polyethylene cap and secured with electrical tape. The reaction was heated at 100° C. in oil bath for 24 h, and then allowed to cool down to room temperature. Water (10 mL) was added to quench the reaction. The layers were separated and the aqueous layer was extracted with CH$_2$Cl$_2$ (3×10 mL). The combined organic layers were dried over MgSO$_4$, filtered and concentrated. Purification by flash chromatography on silica (ca. 150 mL) eluting with 5% EtOAc/hexanes afforded the title compound (3.72 g, 7.39 mmol, 84% yield) as a white powder. $^1$H NMR (500 MHz, CDCl$_3$) δ 8.38 (s, 1H), 8.24 (s, 2H), 7.61 (s, 2H), 4.92 (s, 2H), 0.99 (s, 9H), 0.16 (s, 6H). HRMS (ESI) m/z calc'd for C$_{21}$H$_{23}$F$_9$NOSi [M+H]$^+$: 504.1405, found 504.1409.

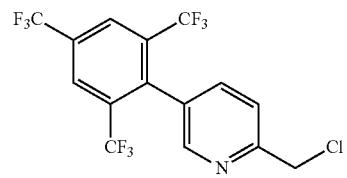 [SMILES: FC(F)(F)c1cc(C(F)(F)F)c(-c2ccc(CCl)nc2)c(C(F)(F)F)c1]

2-(chloromethyl)-5-(2,4,6-tris(trifluoromethyl)phenyl)pyridine. This reaction was performed open to air. According to the procedure of White et al. (Gormisky, P. E.; White, M. C. J. Am. Chem. Soc. 2013, 135, 14052), a 50 mL round-bottom flask was charged with a stir bar and 2-(((tert-butyldimethylsilyl)oxy)methyl)-5-(2,4,6-tris(trifluoromethyl)phenyl)pyridine (3.72 g, 7.39 mmol, 1.0 equiv.). EtOH (7.6 mL) was added to dissolve the substrate, followed by addition of HCl (3 M, 7.6 mL). The reaction was stirred for 3 h when all precipitate dissolved back into solution. CH$_2$Cl$_2$ was added to dilute the reaction mixture and saturated NaHCO$_3$ was added to quench the reaction to neutral pH. The layers were separated and the aqueous layer was extracted with CH$_2$Cl$_2$ (3×5 mL). The organic layers were combined, dried over MgSO$_4$, filtered and concentrated. The crude solid obtained was placed under high vacuum to remove the EtOH residue for 30 min and then reconstituted in CH$_2$Cl$_2$ (37 mL). SOCl$_2$ (5.4 mL, 73.9 mmol, 10 equiv., Sigma-Aldrich) was added dropwise. The reaction was then capped and stirred overnight. Saturated NaHCO$_3$ was carefully added to quench the reaction and the layers were separated. The aqueous layer was extracted with CH$_2$Cl$_2$ (3×10 mL). The organic layers were combined, dried over MgSO₄, filtered and concentrated. Purification by flash chromatography on silica (ca. 75 mL) eluting with 2% to 5% EtOAc/hexanes afforded the title compound (2.55 g, 6.28 mmol, 85% yield) as a white solid. ¹H NMR (400 MHz, CDCl₃) δ 8.45 (s, 1H), 8.25 (s, 2H), 7.65 (d, J=8.7 Hz, 2H), 7.60 (d, J=8.0 Hz, 2H), 4.77 (s, 2H). HRMS (ESI) m/z calc'd for $C_{15}H_8ClF_9N$ [M+H]⁺: 408.0202, found 408.0204.

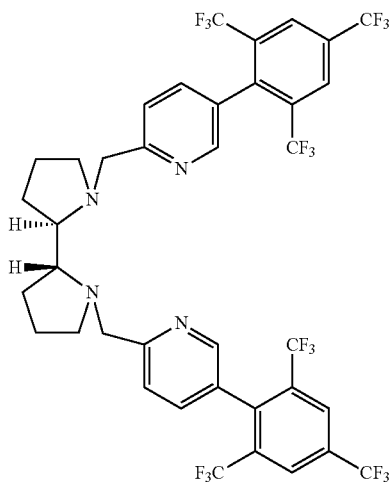 [SMILES: FC(F)(F)c1cc(C(F)(F)F)c(-c2ccc(CN3CCC[C@@H]3[C@H]3CCCN3Cc3ccc(-c4c(C(F)(F)F)cc(C(F)(F)F)cc4C(F)(F)F)cn3)nc2)c(C(F)(F)F)c1]

(2R,2'R)-1,1'-bis((5-(2,4,6-tris(trifluoromethyl)phenyl)pyridin-2-yl)methyl)-2,2'-bipyrrolidine [(R,R)-(tri-CF₃-PDP)]. This reaction was performed open to air. According to the procedure of White et al. (Gormisky, P. E.; White, M. C. J. Am. Chem. Soc. 2013, 135, 14052), a 50 mL round-bottom flask was charged with a stir bar, (S,S)-2,2'-bipyrrolidine D-tartrate (377 mg, 1.30 mmol, 1.0 equiv.), 2-(chloromethyl)-5-(2,4,6-tris(trifluoromethyl)phenyl)pyridine (1.16 g, 2.86 mmol, 2.2 equiv.) and NaOH (333 mg, 8.32 mmol, 6.4 equiv., Fisher). The mixture was dissolved in 1:1 CH₂Cl₂:H₂O (5.2 mL) and stirred vigorously for 24 h at room temperature. The reaction was diluted with 1 M NaOH and CH₂Cl₂. The layers were separated and the aqueous layer was extracted with CH₂Cl₂ (5×5 mL). The combined organic layers were dried over K₂CO₃, filtered and concentrated. Purification by flash chromatography on silica (ca. 150 mL) eluting with 5% to 10% MeOH/CH₂Cl₂ with 1% NH₄OH afforded the crude ligand after concentration, which was partitioned between 1 M NaOH and CH₂Cl₂ in order to remove the NH₃ and water residue. The aqueous layer was extracted with CH₂Cl₂ (5×10 mL). The organic layers were combined, dried over K₂CO₃, filtered and concentrated to afford the title compound (966 mg, 1.09 mmol, 84% yield) as a white powder. ¹H NMR (500 MHz, CDCl₃) δ 8.40 (s, 2H), 8.24 (s, 4H), 7.53 (s, 4H), 3.94 (ABq, J=14.5 Hz, Δv=286.8 Hz, 4H), 3.05 (dt, J=9.2, 4.4 Hz, 2H), 2.76 (dt, J=6.3 Hz, 3H), 2.30 (q, J=8.6 Hz, 2H), 1.87-1.69 (m, 7H). (S,S)-(tri-CF₃-PDP) was also prepared in the same manner.

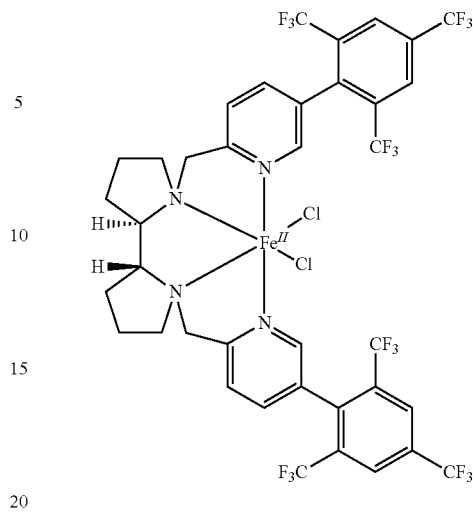

(R,R)—Fe(tri-CF₃-PDP) Cl₂. This reaction was performed open to air. According to the procedure of White et al. (Gormisky, P. E.; White, M. C. J. Am. Chem. Soc. 2013, 135, 14052), a 100 mL round bottom flask was charged with a stir bar and (R,R)-(tri-CF₃-PDP) (961.4 mg, 1.09 mmol, 1.0 equiv.) and CH₂Cl₂ (3.3 mL). The reaction was stirred until the ligand fully dissolved. MeCN (3.3 mL) was then added, followed by FeCl₂.4 H₂O (216.5 mg, 1.09 mmol, 1.0 equiv., Sigma-Aldrich, stored and weighed out in the glove box). The solution turned red immediately after the addition of the iron salt. The reaction was stirred for 24 h, at which time Et₂O (100 mL) was added to precipitate out the title compound. The orange solution was decanted out via pipette, and the precipitate was washed with Et₂O (3×10 mL). The precipitate was then dried under a stream of N₂ overnight to afford the title compound (999 mg, 0.99 mmol, 91% yield) as an orange-red crystal. HRMS (ESI) m/z calc'd for $C_{38}H_{28}ClF_{18}FeN_4$ [M–Cl]⁺: 973.1064, found 973.1079. (S,S)—Fe(tri-CF₃-PDP)Cl₂ was also prepared in the same manner.

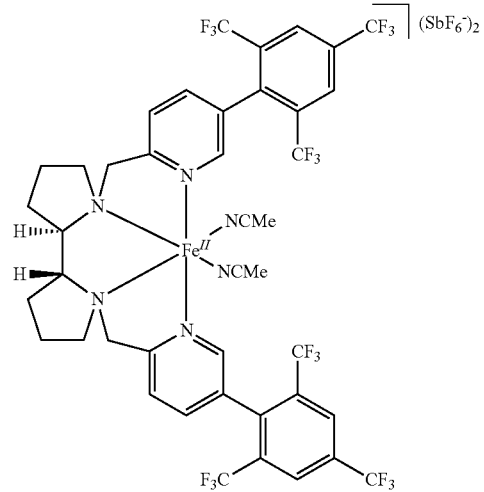

[(R,R)—Fe(tri-CF₃-PDP)(MeCN)₂](SbF₆)₂ (2). According to the procedure of White et al. (Gormisky, P. E.; White, M. C. J. Am. Chem. Soc. 2013, 135, 14052), a 25 mL round bottom flask was charged with a stir bar, (R,R)—Fe(tri-CF₃-

PDP)Cl$_2$ (527.9 mg, 0.523 mmol, 1.0 equiv.) and MeCN (6.5 mL). The flask was wrapped with aluminum foil to exclude light. AgSbF$_6$ (359.4 mg, 1.046 mmol, 2.0 equiv., Strem, stored and weighed out in the glove box with precautions taken to exclude light, air and moisture) was added in one portion resulting immediate precipitation of AgCl. The reaction was stirred vigorously for 24 h, at which time the solution was filtered through Celite® and concentrated to near dryness. The catalyst was reconstituted in MeCN, filtered through a 0.2 μm Acrodisc® LC PVDF (HPLC certified) into a 20 mL scintillation vial and concentrated early to dryness. The filtration procedure was repeated (×2) to ensure complete removal of silver salts. The resulting solid was dried under a stream of N$_2$ overnight to afford the title compound (762 mg, 0.51 mmol, 98% yield) as a red crystal.

[(S,S)—Fe(tri-CF$_3$-PDP)(MeCN)$_2$](SbF$_6$)$_2$ was also prepared in the same manner. The X-ray quality crystals of which were prepared in accordance with procedures described by White et al. (Gormisky, P. E.; White, M. C. *J. Am. Chem. Soc.* 2013, 135, 14052). In a ½ dram vial charged with 30 mg of the complex was added minimum MeCN to fully dissolve the solid. A drop of PhH was then added. The vial was loosely capped and placed into a 20 mL scintillation vial filled with ca. 7 mL Et$_2$O. The 20 mL vial was tightly capped and sit still on bench. After 1 day, dark red crystals formed after Et$_2$O slowly diffused into the smaller vial.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A composition comprising a complex of Formula (I):

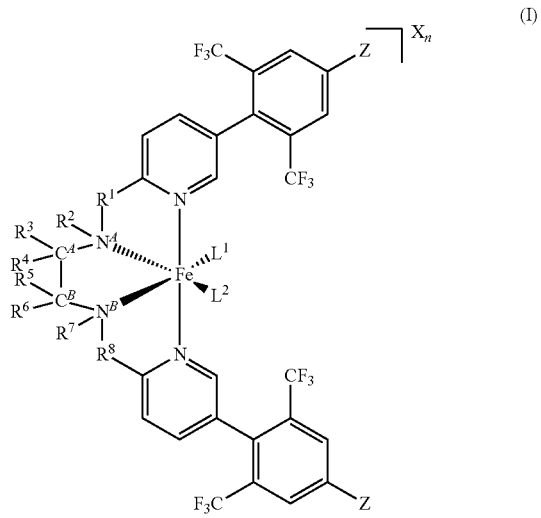

(I)

where X is a counterion;
n is 2 or 3;
L$^1$ and L$^2$ are ligands;
each Z is independently H or CF$_3$;
R$^1$, R$^2$, R$^7$ and R$^8$ are each independently an alkyl group, or a heteroalkyl group;
R$^3$, R$^4$, R$^5$ and R$^6$ are each independently hydrogen, halo, alkyl, or heteroalkyl;
C$^A$ and C$^B$ are carbon atoms and N$^A$ and N$^B$ are nitrogen atoms, where the superscript on the atoms denotes their separate locations;
C$^A$ and N$^A$, in combination with one pair of groups selected from the group consisting of R$^1$ and R$^3$, R$^1$ and R$^4$, R$^2$ and R$^3$, and R$^2$ and R$^4$, form a pyrrolidine ring; and
C$^B$ and N$^B$, in combination with one pair of groups selected from the group consisting of R$^8$ and R$^6$, R$^8$ and R$^5$, R$^7$ and R$^6$, and R$^7$ and R$^5$, form a pyrrolidine ring; and
wherein C$^A$ and C$^B$, together with at least one pair of groups selected from the group consisting of R$^3$ and R$^5$, R$^4$ and R$^6$, R$^4$ and R$^5$, and R$^3$ and R$^6$, optionally form a cyclopentanyl ring.

2. The composition of claim 1 wherein the complex of Formula (I) is an (S,S) enantiomer.

3. The composition of claim 1 wherein the complex of Formula (I) is an (R,R) enantiomer.

4. The composition of claim 1 wherein X is Cl$^-$, Br$^-$, AcO$^-$, TfO$^-$, CF$_3$CO$_2^-$, BF$_4^-$, ClO$_4^-$, ReO$_4^-$, AsF$_6^-$, or SbF$_6^-$.

5. The composition of claim 1 wherein L$^1$ and L$^2$ are independently acetone, acetonitrile, or a μ-oxo bridge.

6. The composition of claim 1 wherein R$^1$, R$^2$, R$^7$ and R$^8$ are each independently an alkyl group, and R$^3$, R$^4$, R$^5$ and R$^6$ are each independently hydrogen or alkyl.

7. The composition of claim 1 in combination with an oxidant.

8. The composition of claim 7 wherein the oxidant is hydrogen peroxide, ozone, a peracid, an alkyl hydroperoxide, or a periodinane.

9. The composition of claim 1 wherein the complex of Formula (I) is a complex of Formula (II):

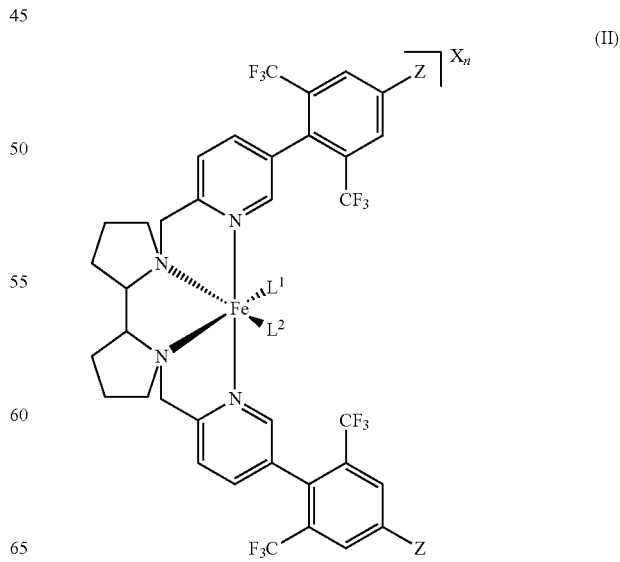

(II)

wherein X is a counterion selected from the group consisting of Cl⁻, Br⁻, AcO⁻, TfO⁻, $CF_3CO_2^-$, $BF_4^-$, $ClO_4^-$, $ReO_4^-$, $AsF_6^-$, and $SbF_6^-$;

n is 2 or 3;

each Z is independently H or $CF_3$; and $L^1$ and $L^2$ are ligands, wherein the ligands are each independently acetone, acetonitrile, or a μ-oxo bridge; or $L^1$ and $L^2$ together are a carboxylate group.

10. The composition of claim 9 wherein the complex of Formula (II) is the (S,S) enantiomer or the (R,R) enantiomer.

11. The complex (R,R)-Fe(CF3-PDP):

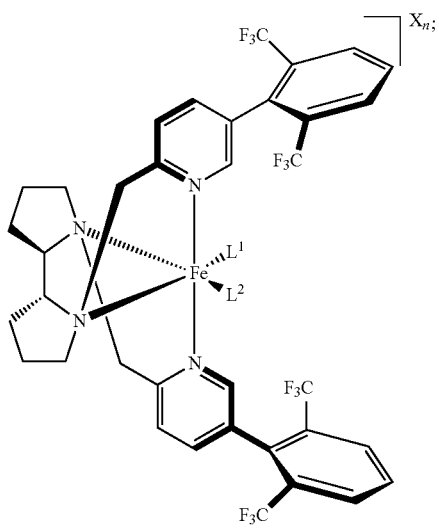

or its (S,S) enantiomer;

wherein X is a counterion selected from the group consisting of Cl⁻, Br⁻, AcO⁻, TfO⁻, $CF_3CO_2^-$, $BF_4^-$, $ClO_4^-$, $ReO_4^-$, $AsF_6^-$, and $SbF_6^-$; n is 2 or 3; and $L^1$ and $L^2$ are acetonitrile.

12. The complex (R,R)-Fe(tri-CF3-PDP):

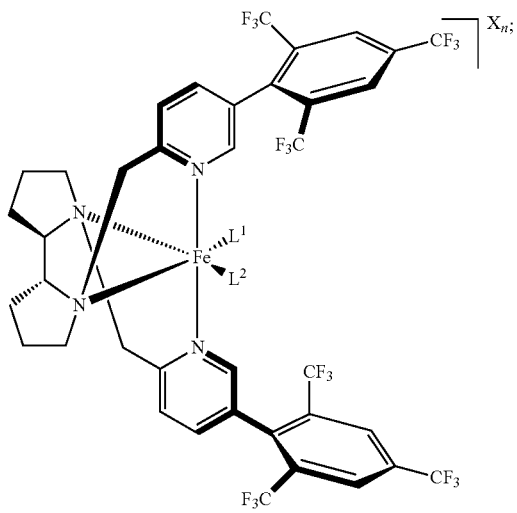

or its (S,S) enantiomer;

wherein X is a counterion selected from the group consisting of Cl⁻, Br⁻, AcO⁻, TfO⁻, $CF_3CO_2^-$, $BF_4^-$, $ClO_4^-$, $ReO_4^-$, $AsF_6^-$, and $SbF_6^-$; n is 2 or 3; and $L^1$ and $L^2$ are acetonitrile.

13. A method of oxidizing an organic substrate comprising contacting a substrate and an oxidant in a first reaction mixture, wherein the first reaction mixture comprises a composition of claim 1, thereby oxidizing the organic substrate to provide an oxidized product.

14. The method of claim 13 wherein the oxidant is hydrogen peroxide, ozone, a peracid, an alkyl hydroperoxide, or a periodinane.

15. The method of claim 13 wherein the first reaction mixture further comprises a solvent comprising acetonitrile.

16. The method of claim 13 wherein providing the oxidized product comprises providing a mono-oxidized product in a yield of at least about 40%.

17. A method of selectively oxidizing an sp³-hybridized C—H bond in a molecule comprising:

contacting a substrate having an sp³-hybridized C—H bond and an oxidant in a first reaction mixture in the presence of a composition of claim 1, thereby selectively oxidizing an sp³-hybridized C—H bond in the molecule to provide an oxidized product.

* * * * *